(12) United States Patent
Illig et al.

(10) Patent No.: US 7,645,755 B2
(45) Date of Patent: Jan. 12, 2010

(54) INHIBITORS OF C-FMS KINASE

(75) Inventors: Carl R. Illig, Phoenixville, PA (US);
Shelley K. Ballentine, Lansdale, PA (US); Jinsheng Chen, Exton, PA (US); Sanath K. Meegalla, Boothwyn, PA (US); M. Jonathan Rudolph, Doylestown, PA (US); Mark J. Wall, Harleysville, PA (US); Kenneth J. Wilson, Media, PA (US); Renee L. Desjarlais, Saint Davids, PA (US); Carl L. Manthey, Downingtown, PA (US); Christopher Flores, Lansdale, PA (US); Christopher J. Molloy, Yardley, PA (US)

(73) Assignee: Janssen Pharmaceutical N.V., Beerse (BE)

( * ) Notice: Subject to any disclaimer, the term of this patent is extended or adjusted under 35 U.S.C. 154(b) by 349 days.

(21) Appl. No.: 11/408,096

(22) Filed: Apr. 20, 2006

(65) Prior Publication Data

US 2006/0189623 A1    Aug. 24, 2006

Related U.S. Application Data

(63) Continuation-in-part of application No. 11/254,276, filed on Oct. 20, 2005.

(60) Provisional application No. 60/670,172, filed on Apr. 11, 2005, provisional application No. 60/621,211, filed on Oct. 22, 2004.

(51) Int. Cl.
*A61K 31/5377* (2006.01)
*A61K 31/454* (2006.01)
*C07D 413/14* (2006.01)
*C07D 401/02* (2006.01)

(52) U.S. Cl. ............ 514/235.8; 514/326; 544/129; 546/210

(58) Field of Classification Search ............ 514/252.13, 514/318, 326, 397, 235.8; 544/374, 379, 544/129; 546/193, 194, 209, 210; 548/311.1
See application file for complete search history.

(56) References Cited

U.S. PATENT DOCUMENTS

| | | | |
|---|---|---|---|
| 5,190,541 | A | 3/1993 | Abele et al. |
| 5,944,718 | A | 8/1999 | Austin et al. |
| 6,100,254 | A | 8/2000 | Budde et al. |
| 6,235,746 | B1 | 5/2001 | Davis et al. |
| 6,346,625 | B1 | 2/2002 | Karabelaset et al. |
| 6,383,790 | B1 | 5/2002 | Shokat |
| 6,596,746 | B1 | 7/2003 | Das et al. |
| 6,692,491 | B1 | 2/2004 | Phan |
| 7,157,456 | B2 | 1/2007 | Straub et al. |
| 2003/0153610 | A1 | 8/2003 | Straub et al. |
| 2005/0004112 | A1* | 1/2005 | Player et al. .............. 514/227.5 |
| 2006/0100619 | A1 | 5/2006 | McClurken et al. |
| 2006/0122181 | A1 | 6/2006 | Ikemoto et al. |
| 2006/0148812 | A1* | 7/2006 | Illig et al. .............. 514/252.13 |
| 2006/0258724 | A1 | 11/2006 | Straub et al. |

FOREIGN PATENT DOCUMENTS

| | | |
|---|---|---|
| WO | WO 98/28264 | 7/1998 |
| WO | WO 00/27820 A1 | 5/2000 |
| WO | WO 01/47897 A1 | 7/2001 |
| WO | WO 01/47919 A1 | 7/2001 |
| WO | WO 02/068406 A2 | 9/2002 |
| WO | WO 2004/085388 | 10/2004 |

OTHER PUBLICATIONS

Vippagunta et al., Crystalline solids, 2001, Advanced Drug Delivery Reviews, 48, pp. 3 and 18.*
Gray, M., et al. "Practical Methylation of Aryl Halides by Suzuki-Miyaura Coupling" Tetrahedron Letters, 41:6237-40 (2000).
Katritsky, et al., "para-Formylation of Nitroarenes via *Vicarious nucleophilic* Substitution of Hydrogen with Tris)benzotriazol-1-yl)methane" Tetrahedron Letters 37:347-50 (1996).
Lewis, et al. "Diacetoxypiperidinium Analogs of Acetylcholine", Junal of Medicinal Chemistry, 1973, vol. 16, No. 2 pp. 156-159.

(Continued)

*Primary Examiner*—Kamal A Saeed
*Assistant Examiner*—Kristin Bianchi
(74) *Attorney, Agent, or Firm*—Mary A. Appollina

(57) ABSTRACT

The invention is directed to compounds of Formula I:

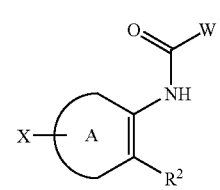

wherein A, X, $R^2$ and W are set forth in the specification, as well as solvates, hydrates, tautomers and pharmaceutically acceptable salts thereof, that inhibit protein tyrosine kinases, especially c-fms kinase. Methods of treating autoimmune diseases; and diseases with an inflammatory component; treating metastasis from ovarian cancer, uterine cancer, breast cancer, colon cancer, stomach cancer, hairy cell leukemia and non-small lung carcinoma; and treating pain, including skeletal pain caused by tumor metastasis or osteoarthritis, or visceral, inflammatory, and neurogenic pain; as well as osteoporosis, Paget's disease, and other diseases in which bone resorption mediates morbidity including arthritis, prosthesis failure, osteolytic sarcoma, myeloma, and tumor metastasis to bone with the compounds of Formula I, are also provided.

7 Claims, No Drawings

OTHER PUBLICATIONS

Miyaura, N., Palladium-Catalyzed Cross-Coupling Reactions of Organoboron Compound, Chem. Rev. 95-2457 (1995).

Muci, et al., "Practical Palladium Catalysts for C-N and C-O Bond Formation", Top. Curr., Chem. 219-131-209 (2001.

Olah, et al., "Formylating Agents", Chem. Rev. 87: 1987.

Regan. J., "Structure-Activity Relationships of the pe8α MAAAP Kinase Inhibitor 1-(5-tert-Butyl-2-p-tolyl-2H-prazol-3-yl)-3-[4-(2-morpholin-4-yl-ethoxynaphthalen-1-yl]urea (BIRB 796)", Med. Chem. 46:4676-86 (2003) Med. Chem. 46:2837 (2003).

Stille, J.K. Angew, "The Palladium-Catalyzed Cross-Coupling Reactions of Organotin Reagents with Organic Electrophiles", Chem. Int. Ed. Engl. 25:508024 (1986).

Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).

Bodansky, M. et al., "The Practice of Peptide Synthesis", Springer-Verlag, NY (1984).

Canibano, V. et al., "Mild Regioselective Halogenation of Activated Pyridines with N-Bromusuccinimide", Synthesis, No. 14, 2175 (2001).

Iddon. B. et al., "Polyhalogenoaromatic Compounds. Part 42. C N.m.r. Spectra of Polyhalogeno-pyridines and pyrimidines", J. Chem. Soc. Perkin Trans. 1., 1370, (1980).

Kamwakami J., et al. "A Convenient Synthesis of 4(5)-Alkylacyl-1H-imidazoles from 4(5)-Imidazolecarboxaldehyde" Synthesis, No. 5, pp. 677-680 (2003).

Kolder, C.R., et al, "Synthesis and Reactivity of 5-Chloro-2,4-Dihydrosypyridine", x Recl. Trav. Chim. Pays-Bas; 285 (1953).

Lyon, R., et al., "Synthesis and Evaluation of Phenyl-and Benzoylpiperazines as Potential Serotonergic Agents", J. Med. Chem., 29: 630-4 (1986).

Modern Amination Methods: Ricci, A., Ed., Wiley-VCH: Weinheim, 2000.

Murata, K. et al., "Synthesis of Alkenylboronates via Palladium-Catalyzed Borylation of Alkenyl Triflates (or Iodindes) with Pinacolborane" Synthesis, 2000, No. 6, pp. 778-780.

Wustrow, et al, "Coupling of Arylboronic Acids with a Partially Reduced Pyridine Derivative" Synthesis, 993 (1991).

Loader, C., et al., "Pyrrole chemistry. XXIII. The cyanation of substituted pyrroles with chlorosulfonyl isocyanate (CSI). New syntheses of pyrrole-3-carbonitriles.", Can. J. Chem, 59, 2673 (1981).

Major, R., et al. "1-Alkoxy-4-phenyl-4-propionoxypiperdines and Their 3-Methyl Homologs as New Analgesics", vol. 26, pp. 1867-1847, (1961).

Nicolai, E., et al., "New Process for the Synthesis of Imidazo[4-5-b]pyridine Derivatives as Potent Orally Active Thromboxane $A_2$ Receptor Antagonists", J. Heterocyclic Chemistry, 31, (73) (1994).

Jonas, Nilsson W. et al., "Solid-Phase Synthesis of Libraries Generated from a 4-Phenyl-2-carboxy-piperazine Scaffold", J. Comb. Chem., 2001, 3, 546-553.

Moffett, Robert Bruce et al., "Antiulcer Agents. p-Aminobenzamido Aromatic Compounds", Journal of Medicinal Chemistry, 1971, vol. 14, No. 10, pp. 963-968.

Chemcats RN 712290-43, Jan. 1, 2004.

Chemcats RN 701272-70-0, Jan. 1, 2004.

Chemcats RN 443895-82-7 Apr. 24, 2003.

Chemcats RN 93730-20-2, Nov. 28, 1988.

* cited by examiner

INHIBITORS OF C-FMS KINASE

RELATIONSHIP TO OTHER APPLICATIONS

This application is a continuation-in-part of U.S. Ser. No. 11/254,276 filed Oct. 20, 2005; which in turn claimed benefit under 35 U.S.C. § 119(e) to Provisional Applications No. 60/670,172, filed Apr. 11, 2005 and No. 60/621,211, filed Oct. 22, 2004.

BACKGROUND OF THE INVENTION

The invention relates to novel compounds that function as protein tyrosine kinase inhibitors. More particularly, the invention relates to novel compounds that function as inhibitors of c-fms kinase.

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. The invention is directed to the novel compounds of Formula I:

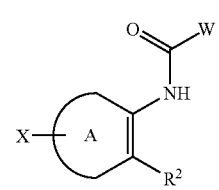

or a solvate, hydrate, tautomer or pharmaceutically acceptable salt thereof, wherein:

A is
  phenyl or pyridyl, either of which may be substituted with one of chloro, fluoro, methyl, —N$_3$, —NH$_2$, —NH(alkyl), —N(alkyl)$_2$, —S(alkyl), —O(alkyl), or 4-aminophenyl;

W is
  pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —Cl, —CN, —NO$_2$, —OMe, or —CF$_3$ substitution, connected to any other carbon;

R$^2$ is
  cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and C$_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;

X is

[chemical structures showing various ring systems with labels $R^3-Q_b$, $Q_a-E$, $D^1$, $D^2$, $D^3$, $D^4$, $D^5$, $Z$, $H_3C$, $R_a$, $O_2S-N$, $R_b$]

Z is
  CH or N;
$D^1$ and $D^2$ are
  each hydrogen or taken together form a double bond to an oxygen;
$D^3$ and $D^4$ are
  each hydrogen or taken together form a double bond to an oxygen;
$D^5$ is
  hydrogen or —$CH_3$, wherein said —$CH_3$ may be relatively oriented syn or anti;
$R_a$ and $R_b$ are independently
  hydrogen, cycloalkyl, haloalkyl, aryl, aralkyl, heteroaryl, or heteroaralkyl;
E is
  N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
$Q_a$ is
  absent, —$CH_2$—, —$CH_2CH_2$—, or C(O);
$Q_b$ is
  absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;
$R^3$ is
  hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxyeth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;

$R^4$ is
  hydrogen, —OH, alkoxy, carboxy, carboxamido, or carbamoyl.

The compounds of Formula I are especially potent inhibitors of the c-fms protein tyrosine kinase.

The invention also relates to methods of inhibiting protein tyrosine kinase activity in a mammal by administration of a therapeutically effective amount of at least one compound of Formula I.

DETAILED DESCRIPTION OF THE INVENTION

The invention is directed to the novel compounds of Formula I:

[chemical structure showing Formula I with X, A, $R^2$, NH, W, O substituents]

or a solvate, hydrate, tautomer or pharmaceutically acceptable salt thereof, wherein:
A is
  phenyl or pyridyl, either of which may be substituted with one of chloro, fluoro, methyl, —$N_3$, —$NH_2$, —NH(alkyl), —N(alkyl)$_2$, —S(alkyl), —O(alkyl), or 4-aminophenyl;
W is
  pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —Cl, —CN, —$NO_2$, —OMe, or —$CF_3$ substitution, connected to any other carbon;
$R^2$ is
  cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;

X is

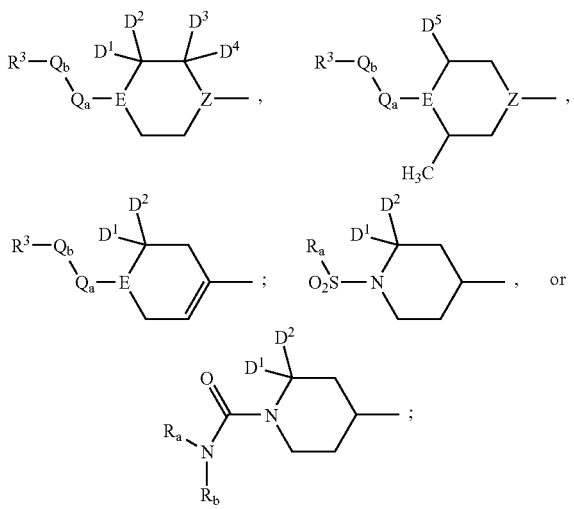

Z is
CH or N;
$D^1$ and $D^2$ are
each hydrogen or taken together form a double bond to an oxygen;
$D^3$ and $D^4$ are
each hydrogen or taken together form a double bond to an oxygen;
$D^5$ is
hydrogen or —$CH_3$, wherein said —$CH_3$ may be relatively oriented syn or anti;
$R_a$ and $R_b$ are independently
hydrogen, cycloalkyl, haloalkyl, aryl, aralkyl, heteroaryl, or heteroaralkyl;
E is
N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
$Q_a$ is
absent, —$CH_2$—, —$CH_2CH_2$—, or C(O);
$Q_b$ is
absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;
$R^3$ is
hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxy eth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;
$R^4$ is
hydrogen, —OH, alkoxy, carboxy, carboxamido, or carbamoyl.

Embodiments of the present invention include a compound of Formula I wherein:
a) A is
phenyl or pyridyl, either of which may be substituted with one of chloro, fluoro, methyl, —$N_3$, —$NH_2$, —NH(alkyl), —N(alkyl)$_2$, —S(alkyl), —O(alkyl), or 4-aminophenyl;
b) A is
phenyl;
c) W is
pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —Cl, —CN, —$NO_2$, —OMe, or —$CF_3$ substitution, connected to any other carbon;
d) W is
furan-2-yl, 1H-pyrrol-2-yl, or 1H-imidazol-2-yl, any of which may be substituted at the 4 or 5 carbons with —CN;
e) W is
3H-2-imidazolyl-4-carbonitrile or 5-cyano-1H-pyrrol-2-yl;
f) W is
3H-2-imidazolyl-4-carbonitrile;
g) $R^2$ is
cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;
h) $R^2$ is
cycloalkyl (including cyclohexenyl, cyclopentenyl), which may substituted with one or two $C_{(1-3)}$alkyl (including 4,4-dimethyl cyclohexenyl, 4-methyl cyclohexenyl);
i) $R^2$ is
cyclohexenyl, which may substituted with one or two $C_{(1-3)}$alkyl:
j) $R^2$ is
cyclohexenyl, 4,4-dimethyl cyclohexenyl, or 4-methyl cyclohexenyl;
k) $R^2$ is
cyclohexenyl;

l) X is

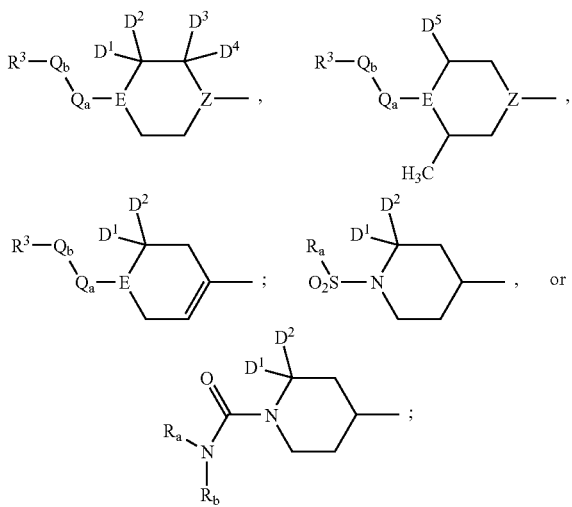

m) X is

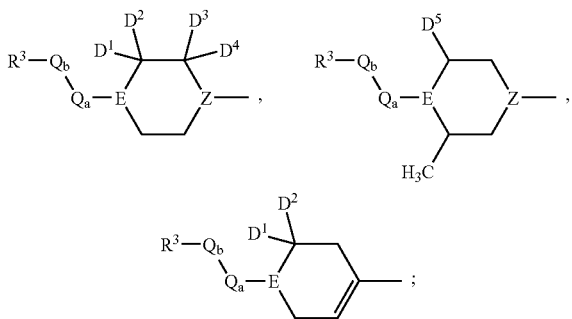

n) X is

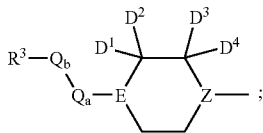

o) Z is
   CH or N;
p) Z is
   CH;
q) $D^1$ and $D^2$ are
   each hydrogen or taken together form a double bond to an oxygen;
r) $D^1$ and $D^2$ are
   each hydrogen;
s) $D^3$ and $D^4$ are
   each hydrogen or taken together form a double bond to an oxygen;
t) $D^3$ and $D^4$ are
   each hydrogen;
u) $D^5$ is
   hydrogen or —$CH_3$, wherein said —$CH_3$ may be relatively oriented syn or anti;

v) $R_a$ and $R_b$ are independently
   hydrogen, cycloalkyl, haloalkyl, aryl, aralkyl, heteroaryl, or heteroaralkyl;
w) E is
   N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
x) E is
   N, with the proviso that E may not be N if the following three conditions are simultaneously met: $Q_a$ is absent, $Q_b$ is absent, and $R^3$ is an amino group or cyclic amino radical wherein the point of attachment to E is N;
y) $Q_a$ is
   absent, —$CH_2$—, —$CH_2CH_2$—, or C(O);
z) $Q_a$ is
   absent, —$CH_2CH_2$—, or C(O);
aa) $Q_a$ is
   absent, or C(O);
bb) $Q_a$ is
   C(O);
cc) $Q_b$ is
   absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;
dd) $Q_b$ is
   absent, —$CH_2CH_2$—, or C(O), with the proviso that $Q_b$ may not be C(O) if $Q_a$ is C(O);
ee) $Q_b$ is
   absent, or C(O), with the proviso that $Q_b$ may not be C(O) if $Q_a$ is C(O);
ff) $R^3$ is
   hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxy eth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;
gg) $R^3$ is
   hydrogen, phenyl, 2-hydroxy ethylamino, 1-hydroxyeth-2-yl(methyl)amino, methylamino, 2-amino isopropyl, 1,3-dihydroxy isopropyl, 1,2-dihydroxy ethyl, methoxy, dimethylamino, 1-hydroxy eth-2-yl, —COOH, —$CONH_2$, —CN, —$SO_2$—, —$SO_2CH_3$), —$NH_2$, piperidinyl, morpholinyl, imidazolyl, pyridyl, pyridyl N-oxide), or 1 methyl imidazolyl;

hh) $R^3$ is
  alkylamino (including methylamino), dialkylamino (including dimethylamino), or —SO$_2$-alkyl-$R^4$ (including —SO$_2$CH$_3$);
ii) $R^3$ is
  methylamino, dimethylamino, or —SO$_2$CH$_3$;
jj) $R^3$ is
  dimethylamino;
kk) $R^4$ is
  hydrogen, —OH, alkoxy, carboxy, carboxamido, or carbamoyl; and
ll) $R^4$ is
  hydrogen;
and all combinations of a) to ll), inclusive, herein above.

Preferred compounds of Formula I are those wherein W is substituted with one —CN.

Other preferred compounds of Formula I are those wherein:
A is
  pyridyl, which may be substituted with one of chloro, fluoro, methyl, —N$_3$, —NH$_2$, —NH(alkyl), —N(alkyl)$_2$, —S(alkyl), —O(alkyl), or 4-aminophenyl;
W is
  imidazolyl, (including 1H-imidazol-2-yl), which may contain one —CN; and
$R^2$ is
  cycloalkyl.

Still other preferred compounds of Formula I are those wherein:
A is
  phenyl which may be substituted with one of chloro, fluoro, or methyl;
X is

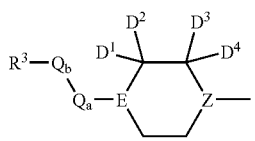

and is attached to the phenyl A ring para to the nitrogen substituent, as depicted in formula II;

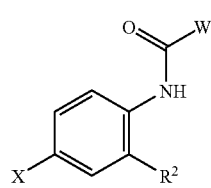

$D^3$ and $D^4$ are hydrogen;
E is
  N or SO$_2$, with the proviso that E may not be N if the following three conditions are simultaneously met: $Q_a$ is absent, $Q_b$ is absent, and $R^3$ is an amino group or cyclic amino radical wherein the point of attachment to E is N; and
$R^3$ is
  hydrogen, piperidinyl, alkylamino, dialkylamino, hydroxyalkylamino, (hydroxyalkyl)$_2$amino, imidazolyl, 1-methyl imidazolyl, pyridyl, pyridyl N-oxide, hydroxyalkyl, —COOH, —CONH$_2$, —CN, —SO$_2$CH$_3$, —NH$_2$, morpholinyl; $R^3$ may also be absent, with the proviso that $R^3$ is not absent when E is nitrogen.

More preferred compounds of Formula I are those wherein:
A is
  phenyl;
W is
  furan-2-yl, 1H-pyrrol-2-yl, or 1H-imidazol-2-yl, any of which may be substituted at the 4 or 5 carbons with —CN;
$R^2$ is
  cycloalkyl, dihydrosulfonopyranyl, phenyl, furanyl, tetrahydropyridyl, or dihydropyranyl, any of which may be independently substituted with one or two of each of the substituents selected from the group consisting of chloro, fluoro, and C$_{(1-3)}$alkyl, with the proviso that tetrahydropyridyl must be connected to the ring A through a carbon-carbon bond.

Even more preferred compounds of Formula I are those wherein:
W is
  3H-2-imidazolyl-4-carbonitrile or 5-cyano-1H-pyrrol-2-yl;
$R^2$ is
  cyclohexenyl, or cyclopentenyl, either of which may be substituted with chloro, fluoro or one two C$_{(1-3)}$alkyl groups;
E is
  N, with the proviso that E may not be N if the following three conditions are simultaneously met: $Q_a$ is absent, $Q_b$ is absent, and $R^3$ is an amino group or cyclic amino radical wherein the point of attachment to E is N;
Z is CH.

Especially preferred compounds of Formula I are those wherein:
W is
  imidazolyl, (including 1H-imidazol-2-yl), 1,2,4 triazolyl, or furanyl (including furan-2-yl), any of which may be connected through any carbon atom, wherein the imidazolyl, 1,2,4 triazolyl, or furanyl may contain one —Cl or —CN, connected to any other carbon;
$R^2$ is
  cycloalkyl (including C$_{(1-3)}$alkyl substituted cycloalkyl, further including C$_{(1-3)}$alkyl substituted cyclopentenyl, and C$_{(1-3)}$alkyl substituted cyclohexenyl, further including 4-methyl cyclohexenyl), C$_{(1-3)}$dialkyl substituted cycloalkyl (including 4,4-dimethyl cyclohexenyl), thiophenyl (including C$_{(1-3)}$alkyl substituted thiophenyl, further including 2-methyl thiophenyl and 3-methyl thiophenyl), C$_{(1-3)}$alkyl substituted phenyl (including methyl phenyl), dihydropyranyl, and 1,1-dioxo-tetrahydrothiopyranyl;
X is

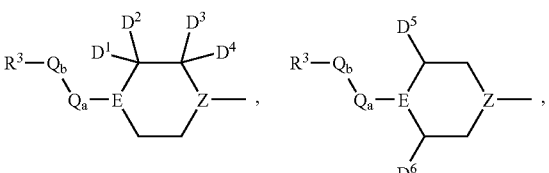

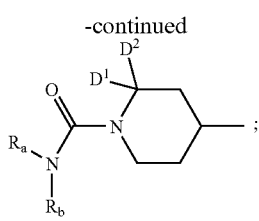

E is
N or SO$_2$, with the proviso that E may not be N if the following three conditions are simultaneously met: Q$_a$ is absent, Q$_b$ is absent, and R$^3$ is an amino group or cyclic amino radical wherein the point of attachment to E is N; and R$^3$ is
hydrogen, phenyl, hydroxyalkylamino (including 2-hydroxy ethylamino), hydroxyalkyl(alkyl)amino (including 1-hydroxyeth-2-yl (methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxy eth-2-yl), —COOH, —CONH$_2$, —CN, —SO$_2$CH$_3$, —NH$_2$, or a 5 or six membered ring selected from the group consisting of: piperidinyl, morpholinyl, imidazolyl, and pyridyl, wherein the 5 or 6 membered ring may be optionally substituted with methyl, halogen, alkylamino, or alkoxy (including 1 methyl imidazolyl), R$^3$ may also be absent, with the proviso that R$^3$ is not absent when E is nitrogen.

Most preferred compounds of Formula I are those wherein:
W is
3H-2-imidazolyl-4-carbonitrile;
Q$_a$ is CO;
R$^3$ is
hydrogen, piperidinyl, hydroxyalkylamino, (hydroxyalkyl)$_2$amino, alkylamino, dialkylamino, imidazolyl, 1-methyl imidazolyl, pyridyl, pyridyl N-oxide, hydroxyalkyl, —COOH, —CONH$_2$, —CN, —SO$_2$CH$_3$, —NH$_2$, morpholinyl.

The compounds of Formula I are especially potent inhibitors of the c-fms protein tyrosine kinase.

The invention also relates to methods of inhibiting protein tyrosine kinase activity in a mammal by administration of a therapeutically effective amount of at least one compound of Formula I.

Examples of compounds of Formula I are:
5-cyano-furan-2-carboxylic acid [4-(4-methyl-piperazin-1-yl)-2-(3-methyl-thiophen-2-yl)-phenyl]-amide, or
5-cyano-furan-2-carboxylic acid [4-(4-methyl-piperazin-1-yl)-2-(2-methyl-thiophen-3-yl)-phenyl]-amide, and solvates, hydrates, tautomers and pharmaceutically acceptable salts thereof.

More preferred examples of compounds of Formula I are:
4-cyano-1H-imidazole-2-carboxylic acid [4-(1-acetyl-piperidin-4-yl)-2-(1,2,5,6-tetrahydro-pyridin-3-yl)-phenyl]-amide,
4-cyano-1H-imidazole-2-carboxylic acid [2-cyclohex-1-enyl-4-(1,1-dioxo-hexahydro-1λ$^6$-thiopyran-4-yl)-phenyl]-amide,
5-cyano-furan-2-carboxylic acid [2-cyclohex-1-enyl-4-(4-methyl-piperazin-1-yl)-phenyl]-amide,
5-cyano-furan-2-carboxylic acid [2-(3,6-dihydro-2H-pyran-4-yl)-4-(4-methyl-piperazin-1-yl)-phenyl]-amide,
4-cyano-1H-imidazole-2-carboxylic acid [2-(1,1-dioxo-1,2,3,6-tetrahydro-1λ$^6$-thiopyran-4-yl)-4-piperidin-4-yl-phenyl]-amide,
4-cyano-1H-imidazole-2-carboxylic acid [4-(1-acetyl-piperidin-4-yl)-2-(1,1-dioxo-1,2,3,6-tetrahydro-1λ$^6$-thiopyran-4-yl)-phenyl]-amide,
5-cyano-furan-2-carboxylic acid [2'-methyl-5-(4-methyl-piperazin-1-yl)-biphenyl-2-yl]-amide, or
5-cyano-furan-2-carboxylic acid [2'-fluoro-5-(4-methyl-piperazin-1-yl)-biphenyl-2-yl]-amide, and solvates, hydrates, tautomers and pharmaceutically acceptable salts thereof.

Even more preferred examples of compounds of Formula I are:
(4-{4-[(4-cyano-1H-imidazole-2-carbonyl)-amino]-3-cyclohex-1-enyl-phenyl}-piperidin-1-yl)-acetic acid,
4-cyano-1H-imidazole-2-carboxylic acid [4-(1-carbamoylmethyl-piperidin-4-yl)-2-cyclohex-1-enyl-phenyl]-amide,
4-cyano-1H-imidazole-2-carboxylic acid [2-(4-methyl-cyclohex-1-enyl)-4-piperidin-4-yl-phenyl]-amide,
4-cyano-1H-imidazole-2-carboxylic acid {2-cyclohex-1-enyl-4-[1-(2-hydroxy-ethyl)-piperidin-4-yl]-phenyl}-amide,
4-cyano-1H-imidazole-2-carboxylic acid [2-(4-methyl-cyclohex-1-enyl)-4-(1-pyridin-2-ylmethyl-piperidin-4-yl)-phenyl]-amide,
4-cyano-1H-imidazole-2-carboxylic acid {2-cyclohex-1-enyl-4-[1-(2-hydroxy-1-hydroxymethyl-ethyl)-piperidin-4-yl]-phenyl}-amide,
4-cyano-1H-imidazole-2-carboxylic acid {4-[1-(2-cyano-ethyl)-piperidin-4-yl ]-2-cyclohex-1-enyl-phenyl}-amide,
4-cyano-1H-imidazole-2-carboxylic acid {2-cyclohex-1-enyl-4-[1-(2-morpholin-4-yl-ethyl)-piperidin-4-yl]-phenyl}-amide,
4-cyano-1H-imidazole-2-carboxylic acid (2-cyclohex-1-enyl-4-piperidin-4-yl-phenyl)-amide,
4-cyano-1H-imidazole-2-carboxylic acid {2-cyclohex-1-enyl-4-[1-(2-methanesulfonyl-ethyl)-piperidin-4-yl]-phenyl}-amide,
4-cyano-1H-imidazole-2-carboxylic acid [2-cyclohex-1-enyl-4-(1-pyridin-2-ylmethyl-piperidin-4-yl)-phenyl]-amide,
4-cyano-1H-imidazole-2-carboxylic acid {2-cyclopent-1-enyl-4-[1-(1-methyl-1H-imidazol-2-ylmethyl)-piperidin-4-yl]-phenyl}-amide,
4-cyano-1H-imidazole-2-carboxylic acid (2-cyclopent-1-enyl-4-piperidin-4-yl-phenyl)-amide,
4-cyano-1H-pyrrole-2-carboxylic acid (2-cyclohex-1-enyl-4-piperidin-4-yl-phenyl)-amide,
4-cyano-1H-imidazole-2-carboxylic acid [2-cyclohex-1-enyl-4-(3,4,5,6-tetrahydro-2H-[1,2']bipyridinyl-4-yl)-phenyl]-amide, or
4-cyano-1H-pyrrole-2-carboxylic acid [4-(1-acetyl-piperidin-4-yl)-2-cyclohex-1-enyl-phenyl]-amide, and solvates, hydrates, tautomers and pharmaceutically acceptable salts thereof.

Most preferred examples of compounds of Formula I are:
4-cyano-1H-imidazole-2-carboxylic acid {2-cyclohex-1-enyl-4-[1-(1-oxy-pyridine-3-carbonyl)-piperidin-4-yl]-phenyl}-amide,
4-cyano-1H-imidazole-2-carboxylic acid {2-cyclohex-1-enyl-4-[1-(1-oxy-pyridine-4-carbonyl)-piperidin-4-yl]-phenyl}-amide, 4-cyano-1H-imidazole-2-carboxylic acid {2-cyclohex-1-enyl-4-[1-(3-morpholin-4-yl-propionyl)-piperidin-4-yl]-phenyl}-amide,
4-{4-[(4-cyano-1H-imidazole-2-carbonyl)-amino]-3-cyclohex-1-enyl-phenyl}-piperidine-1-carboxylic acid amide,
4-cyano-1H-imidazole-2-carboxylic acid {2-cyclohex-1-enyl-4-[1-(pyridine-3-carbonyl)-piperidin-4-yl]-phenyl}-amide,
4-{4-[(4-cyano-1H-imidazole-2-carbonyl)-amino]-3-cyclohex-1-enyl-phenyl}-piperidine-1-carboxylic acid (2-hydroxy-ethyl)-amide,
4-cyano-1H-imidazole-2-carboxylic acid {2-cyclohex-1-enyl-4-[1-(2-3H-imidazol-4-yl-acetyl)-piperidin-4-yl]-phenyl}-amide,
4-cyano-1H-imidazole-2-carboxylic acid {2-cyclohex-1-enyl-4-[1-(2-pyridin-4-yl-acetyl)-piperidin-4-yl]-phenyl}-amide,
4-cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide,
4-cyano-1H-imidazole-2-carboxylic acid {2-cyclohex-1-enyl-4-[1-(2-pyridin-3-yl-acetyl)-piperidin-4-yl]-phenyl}-amide,
4-cyano-1H-imidazole-2-carboxylic acid {2-cyclohex-1-enyl-4-[1-(2-methanesulfonyl-acetyl)-piperidin-4-yl]-phenyl}-amide,
4-cyano-1H-imidazole-2-carboxylic acid {2-cyclohex-1-enyl-4-[1-(2-pyridin-2-yl-acetyl)-piperidin-4-yl]-phenyl}-amide, or
4-cyano-1H-imidazole-2-carboxylic acid [4-(1-acetyl-piperidin-4-yl)-2-cyclohex-1-enyl-phenyl]-amide.

and solvates, hydrates, tautomers and pharmaceutically acceptable salts thereof.

Another most preferred compound of Formula I is:
4-cyano-1H-imidazole-2-carboxylic acid [2-cyclohex-1-enyl-4-(1-{2-[(2-hydroxy-ethyl)-methyl-amino]-acetyl}-piperidin-4-yl)-phenyl ]-amide, and solvates, hydrates, tautomers and pharmaceutically acceptable salts thereof.

An additional most preferred compound of Formula I is:
4-cyano-1H-imidazole-2-carboxylic acid {2-cyclohex-1-enyl-4-[1-(2-dimethylamino-acetyl)-piperidin-4-yl]-phenyl}-amide, and solvates, hydrates, tautomers and pharmaceutically acceptable salts thereof.

One more most preferred compound of Formula I is:
4-cyano-1H-imidazole-2-carboxylic acid {2-cyclohex-1-enyl-4-[1-(2-morpholin-4-yl-acetyl)-piperidin-4-yl]-phenyl}-amide, and solvates, hydrates, tautomers and pharmaceutically acceptable salts thereof.

Still other preferred compounds of formula I are:
4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt,
4H-[1,2,4]-triazole-3-carboxylic acid (2-cyclohex-1-enyl-4-piperidin-4-yl-phenyl)-amide bis trifluoroacetic acid salt,
5-Chloro-4H-[1,2,4]-triazole-3-carboxylic acid (2-cyclohex-1-enyl-4-piperidin-4-yl-phenyl)-amide trifluoroacetic acid salt,
5-Cyano-1H-imidazole-2-carboxylic acid [2-cyclohex-1-enyl-4-(cis-2,6-dimethyl-piperidin-4-yl)-phenyl]-amide bis trifluoroacetic acid salt,
5-cyano-1H-imidazole-2-carboxylic acid [2-cyclohex-1-enyl-4-(trans-2,6-dimethyl-piperidin-4-yl)-phenyl]-amide bis trifluoroacetic acid salt,
5-Cyano-1H-imidazole-2-carboxylic acid {2-cyclohex-1-enyl-4-[1-(R)-(+)-(2,3-dihydroxy-propionyl)-piperidin-4-yl]-phenyl}-amide,
5-Cyano-1H-imidazole-2-carboxylic acid [2-cyclohex-1-enyl-4-(1-methoxy-piperidin-4-yl)-phenyl]-amide trifluoroacetic acid salt,
4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt,
5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt, and
5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide, and solvates, hydrates, tautomers and pharmaceutically acceptable salts thereof.

Additional preferred compounds of Formula I are:
4-Cyano-1H-imidazole-2-carboxylic acid {2-cyclohex-1-enyl-4-[1-(2-methylamino-acetyl)-piperidin-4-yl]-phenyl}-amide,
4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4']bipyridinyl-5-yl]-amide trifluoroacetic acid salt,
4-Cyano-1H-imidazole-2-carboxylic acid [6-(4,4-dimethyl-cyclohex-1-enyl)-1'-(2-methanesulfonyl-ethyl)-1',2',3',4',5',6'-hexhydro-[2,4']bipyridinyl-5-yl]-amide trifluoroacetic acid salt,
5-Cyano-1H-imidazole-2-carboxylic acid [4-(3,6-dihydro-2H-pyran-4-yl)-2-(4,4-dimethyl-cyclohex-1-enyl)-phenyl]-amide;
4-Cyano-1H-imidazole-2-carboxylic acid {2-cyclohept-1-enyl-4-[1-(2-dimethylamino-acetyl)-piperidin-4-yl]-phenyl}-amide trifluoroacetic acid salt;
4-Cyano-1H-imidazole-2-carboxylic acid [4-[1-(2-dimethylamino-acetyl)-piperidin-4-yl]-2-(4,4-dimethyl-cyclohex-1-enyl)-phenyl]-amide trifluoroacetic acid salt;
4-Cyano-1H-pyrrole-2-carboxylic acid {2-cyclohex-1-enyl-4-[1-(2-dimethylamino-acetyl)-piperidin-4-yl]-phenyl}-amide trifluoroacetic acid salt;
4-Cyano-1-imidazole-2-carboxylic acid {2-(4,4-dimethyl-cyclohex-1-enyl)-4-[1-(2-methanesulfonyl-ethyl)-piperidin-4-yl]-phenyl}-amide trifluoroacetic acid salt;

and solvates, hydrates, tautomers and pharmaceutically acceptable salts thereof.

The invention also relates to methods of inhibiting protein tyrosine kinase activity in a mammal by administration of a therapeutically effective amount of at least one compound of Formula I. A preferred tyrosine kinase is c-fms.

The invention is considered to include the enantiomeric, diastereomeric and tautomeric forms of all compounds of Formula I as well as their racemic mixtures. In addition, some of the compounds represented by Formulae I may be prodrugs, i.e., derivatives of an acting drug that possess superior delivery capabilities and therapeutic value as compared to the acting drug. Prodrugs are transformed into active drugs by in vivo enzymatic or chemical processes.

I. Definitions

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "hydroxyalkyl" refers to both linear and branched chain radicals of up to 6 carbon atoms, in which one hydrogen atom has been replaced with an OH group.

The term "hydroxyalkylamino" refers to an hydroxyalkyl group in which one hydrogen atom from the carbon chain has been replaced with an amino group, wherein the nitrogen is the point of attachment to the rest of the molecule.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl, cyclopentenyl, cyclohexenyl, and 4,4-dimethyl cyclohexenyl.

The term "dihydrosulfonopyranyl" refers to the following radical:

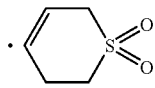

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain, wherein an alkyl group is the point of attachment to the rest of the molecule.

The term "alkylamino" refers to an amino with one alkyl substituent, wherein the amino group is the point of attachment to the rest of the molecule.

The term "dialkylamino" refers to an amino with two alkyl substituents, wherein the amino group is the point of attachment to the rest of the molecule.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napththalene.

The term "aralkyl" refers to a $C_{1-6}$ alkyl group containing an aryl substituent. Examples include benzyl, phenylethyl or 2-naphthylmethyl.

The term "sulfonyl" refers to the group —$S(O)_2R_a$, where $R_a$ is hydrogen, alkyl, cycloalkyl, haloalkyl, aryl, aralkyl, heteroaryl and heteroaralkyl. A "sulfonylating agent" adds the —$S(O)_2R_a$ group to a molecule.

II. Therapeutic Uses

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. The compounds of the present invention are also inhibitors of FLT3 tyrosine kinase activity. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, acute myeloid leukemia, acute lymphocytic leukemia, ovarian cancer, uterine cancer, breast cancer, colon cancer, stomach cancer, hairy cell leukemia and non-small lung carcinoma. The invention also provides methods of treating certain precancerous lesions including myelofibrosis. In one embodiment of the invention, an effective amount of at least one compound of Formula I is administered in combination with an effective amount of a chemotherapeutic agent.

The invention further provides methods of treating and of preventing metastasis arising from cancers that include, but are not limited to, ovarian cancer, uterine cancer, breast cancer, colon cancer, stomach cancer, hairy cell leukemia and non-small lung carcinoma.

The invention further provides methods for the treatment osteoporosis, Paget's disease, and other diseases in which bone resorption mediates morbidity including arthritis, prosthesis failure, osteolytic sarcoma, myeloma, and tumor metastasis to bone as occurs frequently in cancers including, but not limited to, breast cancer, prostate cancer, and colon cancer.

The invention also provides methods of treating pain, in particular skeletal pain caused by tumor metastasis or osteoarthritis, as well as visceral, inflammatory, and neurogenic pain.

The invention also provides methods of treating cardiovascular, inflammatory, and autoimmune diseases in mammals, including humans, by administration of a therapeutically effective amount of a pharmaceutically acceptable form of at least one of the compounds of Formula I. Examples of diseases with an inflammatory component include glomerulonephritis, inflammatory bowel disease, prosthesis failure, sarcoidosis, congestive obstructive pulmonary disease, asthma, pancreatitis, HIV infection, psoriasis, diabetes, tumor related angiogenesis, age-related macular degeneration, diabetic retinopathy, restenosis, schizophrenia or Alzheimer's dementia. These may be effectively treated with compounds of this invention. Other diseases that may be effectively treated include, but are not limited to atherosclerosis and cardiac hypertrophy. Autoimmune diseases such as systemic lupus erythematosus, rheumatoid arthritis, Sjogren's syndrom, multiple sclerosis, or uveitis, can also be treated with compounds of this invention.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

III. Methods of Preparation

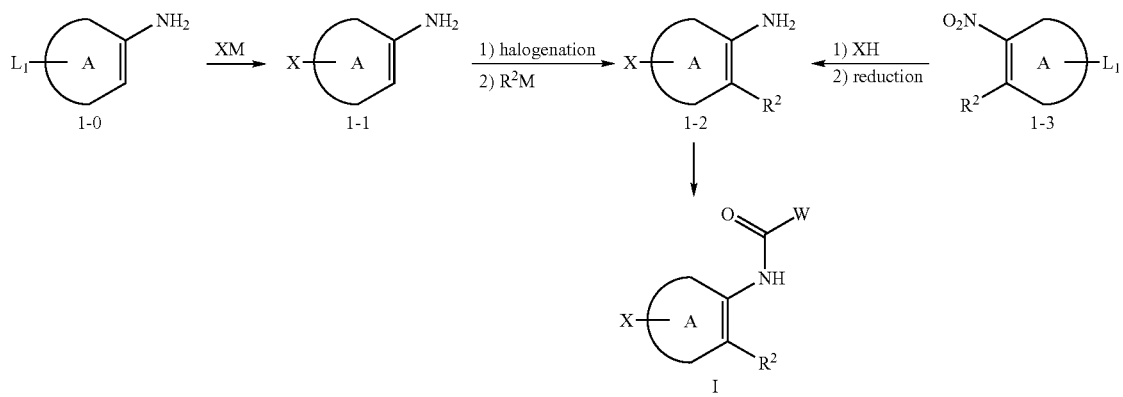

Scheme I illustrates general methodology for the preparation of compounds of Formula I.

Compounds of Formula 1-2 can be obtained by ortho-halogenation, preferably bromination, of amino compounds of Formula 1-1 followed by metal-catalyzed coupling reactions with boronic acids or boronate esters (Suzuki reactions, where $R^2M$ is $R^2B(OH)_2$ or a boronic ester) or tin reagents (Stille reactions, where $R^2M$ is $R^2Sn(alkyl)_3$) (for reviews, see N. Miyaura, A. Suzuki, Chem. Rev., 95:2457 (1995), J. K. Stille, Angew. Chem, Int. Ed. Engl., 25: 508024 (1986) and A. Suzuki in Metal-Catalyzed Coupling Reactions, F. Deiderich, P. Stang, Eds., Wiley-VCH, Weinheim (1988)). Compounds of formula 1-1 may be commercially available, or the above palladium mediated cross-coupling reactions described above may be used to generate compounds of Formula 1-1 from starting material 1-0.

Preferred conditions for the bromination of 1-1 are N-bromosuccinimide (NBS) in a suitable solvent such as N,N-dimethylformamide (DMF), dichloromethane (DCM) or acetonitrile. Metal-catalyzed couplings, preferably Suzuki reactions, can be performed according to standard methodology, preferably in the presence of a palladium catalyst such as tetrakis(triphenylphosphine)palladium(0) (Pd(PPh$_3$)$_4$), an aqueous base such aq. Na$_2$CO$_3$, and a suitable solvent such as toluene, ethanol, dimethoxyethane (DME), or DMF.

Compounds of Formula I can be prepared by reaction of compounds of Formula 1-2 with carboxylic acids WCOOH according to standard procedures for amide bond formation (for a review, see: M. Bodansky and A. Bodansky, The Practice of Peptide Synthesis, Springer-Verlag, NY (1984)) or by reaction with acid chlorides WCOCl or activated esters WCO$_2$Rq (where Rq is a leaving group such as pentafluorophenyl or N-succinimide). The preferred reaction conditions for coupling with WCOOH are: when W is a furan, oxalyl chloride in DCM with DMF as a catalyst to form the acid chloride WCOCl and then coupling in the presence of a trialkylamine such as DIEA; when W is a pyrrole, 1-(3-dimethylaminopropyl)-3-ethylcarbodiimide hydrochloride (EDCI) and 1-hydroxybenzotriazole-6-sulfonamidomethyl hydrochloride (HOBt); and when W is an imidazole, the preferred conditions are bromotripyrrolidinophosphonium hexafluorophosphate (PyBrOP) and diisopropylethylamine (DIEA) in DCM.

It is understood that the optional substitution present on ring A in Formula I may be present in the starting materials 1-1 or 1-3 and, in such cases, would be carried through the synthesis outlined in Scheme 1. Alternatively various substituents on compounds of Formula I may be introduced in a number of ways described below to provide the optional substitution listed for Formula I. The leaving group "L$_1$" present on ring A in Formula 1-0 or 1-3, can be substituted before or at any step during Scheme 1. When such leaving groups (preferably fluoro or chloro) are activated by the nitro group of Formula 1-3 for nucleophilic attack, they can undergo direct nucleophilic aromatic substitution by ammonia and azide anion or by amines, alcohols, thiols and other nucleophiles in the presence of a suitable base such as K$_2$CO$_3$, N,N-diisopropylethylamine (DIEA) or NEt$_3$. When the leaving group is suitable for metal-catalyzed couplings (preferably bromo or trifluoromethanesulfonyloxy), a number of cross-coupling reactions (such as Suzuki or Stille reactions as discussed above for the introduction of R$^2$) may be performed. Other metal-catalyzed coupling reactions that can be employed include aromatic and heteroaromatic amination and amidation (for reviews, see: S. L. Buchwald, et al, *Top. Curr. Chem.*, 219:131-209 (2001) and J. F. Hartwig in "*Organopalladium Chemistry for Organic Synthesis*," Wiley Interscience, NY (2002). Additional metal catalyzed cross coupling reactions with 2,4,6-trimethyl-cyclotriboroxane may be employed if L$_1$ is bromo, iodo, or chloro activated by nitro to generate optional methyl substitution (see M. Gray, et al, Tetrahedron Lett., 41: 6237-40 (2000))

In some cases, the initial substituents can be further derivatized as described below to provide the final substitution of Formula I.

An alternative method for the introduction of nitrogen-containing heterocyclic substituents onto ring A is to form the heterocycle from an amino group on ring A. The amino group may be originally present in the starting material in a protected or unprotected form or may result from the reduction of a nitro group which also can be either originally present in the starting material or attached by a nitration reaction. In addition, the amino group may be formed by reduction of an azide group which can be present in the starting material or may result from nucleophilic aromatic substitution of an activated halide by azide anion as mentioned above. The amino group may also result from nucleophilic aromatic substitution of an activated halide (in, for example a nitrohalo compound) by ammonia or by the anion of a protected ammonia equivalent, for example, t-butyl carbamate. If introduced in protected form, the amine can be deprotected according to standard literature methods. (For examples of amine protecting groups and deprotection methods see: Theodora W. Greene and Peter G. M. Wuts, John Wiley and Sons, Inc., NY (1991).) The ring-forming reaction involves treatment of the aniline amino group with a suitable optionally substituted di-electrophile, preferably a dihalide or dicarbonyl compound, which results in two substitutions on the amino group to form an optionally substituted heterocycle. In the case of dihalides, any of a number of suitable bases can be added as an acid scavenger such as potassium carbonate, sodium hydroxide, or, a trialkylamine such as triethylamine. Thus, treatment with a bis(2-haloethyl)amine such as bis(2-chloroethyl)amine or bis(2-bromoethyl)amine would afford a piperazine ring (see, for example, *J. Med. Chem.*, 29: 640-4 (1986) and *J. Med. Chem.*, 46: 2837 (2003)). Optional substitution on the amine nitrogen of the reagent would incorporate optional substitution on the terminal amine of the piperazine. For example, treatment with N,N-bis(2-chloroethyl)aniline would give an N-phenylpiperazino group. Treatment with a bis(2-haloethyl)ether or bis(2-haloethyl)thioether would afford a morpholine or thiomorpholine ring, respectively.

Another alternative method to direct substitution to introduce heterocyclic substituents onto ring A is to form the heterocycle from an aldehyde (i.e. from a formyl group on ring A). The formyl group may be originally present in the starting material in a protected or unprotected form or may result from or any of a number of formylation reactions known in the literature including a Vilsmeier-Haack reaction (for a review of formylation chemistry, see: G. A. Olah, et al, Chem Rev., 87: (1987)) or by para-formylation of nitroaromatics (see: A. Katritsky and L. Xie, *Tetrahedron Lett.*, 37:347-50 (1996)).

Finally it is understood that compounds of Formula I may be further derivatized. Protecting groups on compounds of Formula I can be removed according to standard synthetic methodologies (Theodora W. Greene and Peter G. M. Wuts, John Wiley and Sons, Inc., NY (1991)) and can be then subjected to further derivatization. Examples of further derivatization of compounds of I include, but are not limited to: when compounds of Formula I contain a primary or secondary amine, the amine may be reacted with aldehydes or ketones in the presence of a reducing agent such as sodium triacetoxyborohydride (see Abdel-Magid *J. Org. Chem.* 61, pp. 3849-3862, (1996)) to reductively alkylate; with acid chlorides or carboxylic acids and an amide bond forming reagent as described above to form amides; with sulfonyl chlorides to form sulfonamides; with isocyanates to form ureas; with aryl- or heteroaryl-halides in the presence of a palladium catalyst as described above (see Buchwald and Hartwig references above) to form aryl and heteroarylamines. In addition, when compounds of Formulae I contain an aryl halide or heteroaryl halide, these compounds may be subjected to metal-catalyzed reactions with boronic acids (for example, Suzuki or Stille couplings as described above), or, amines or alcohols (Buchwald- or Hartwig-type couplings, see Buchwald and Hartwig references above). When compounds of Formulae I contain a cyano group, this group may be hydrolyzed to amides or acids under acid or basic conditions. Basic amines may be oxidized to N-oxides and conversely N-oxides may be reduced to basic amines. When compounds of Formula I contain a sulfide, either acyclic or cyclic, the sulfide can be further oxidized to the corresponding sulfoxides or sulfones. Sulfoxides can be obtained by oxidation using an appropriate oxidant such as one equivalent of (meta-chloroperbenzoicacid) MCPBA or by treatment with NaIO$_4$ (see, for example, J. Regan, et al, *J. Med. Chem.*, 46: 4676-86 (2003)) and sulfones can be obtained using two equivalents of MCPBA or by treatment with 4-methylmorpholine N-oxide and catalytic osmium tetroxide (see, for example, PCT application WO 01/47919).

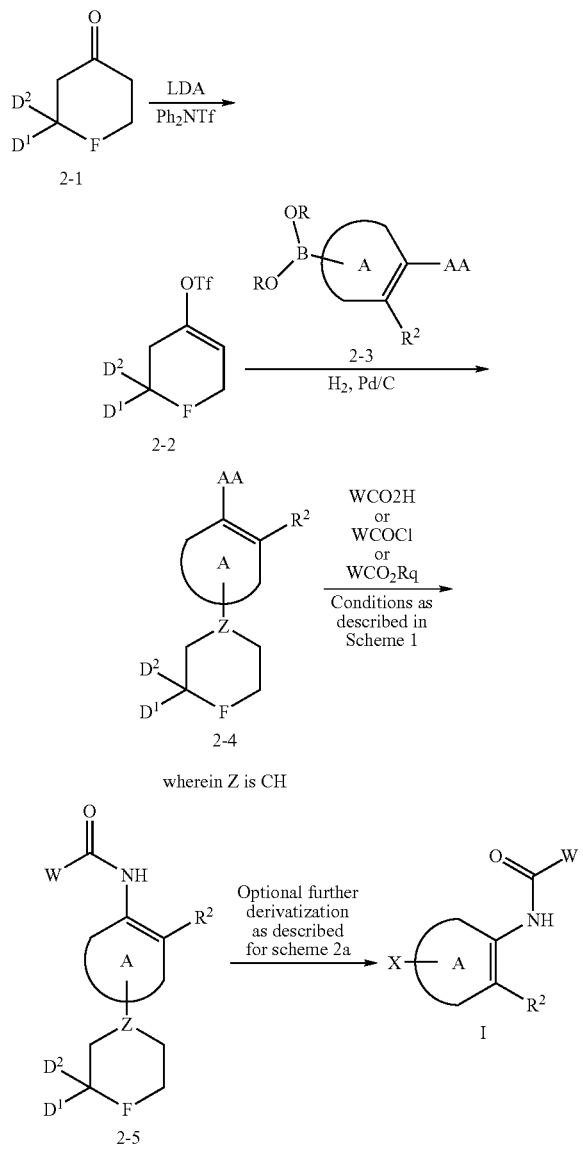

Scheme 2a illustrates a route to compounds of Formula I. F represents —NQ$_a$Q$_b$R$^3$—, —O—, S, SO, or SO$_2$, and AA represents —NH$_2$ or —NO$_2$. D$^1$ and D$^2$ are shown for illustrative purposes only; it is recognized by those skilled in art that D$^5$ D$^6$ D$^7$ D$^8$ may also be present. Ketones of formula 2-1 can be converted to a vinyl triflate of formula 2-2 by treatment with a non-nucleophilic base such as LDA and then trapping of the resulting enolate with a triflating reagent such as trifluoromethanesulfonic anhydride or preferably N-phenyltrifluoromethanesulfonimide. Suzuki coupling of boronic acids or boronate esters of formula 2-3 to vinyl triflates of formula 2-2 can provide compounds of formula 2-4 where Z=C (*Synthesis*, 993 (1991)).

For compounds of formula 2-4 treatment with Pd/C can reduce both the olefin (and the nitro if AA=NO$_2$) to give Z=CH, AA=NH$_2$. Compounds of formula 2-4 where F represents —SO$_2$ can be prepared from compounds of formula 2-4 where AA=—NO$_2$ and F is a sulfide (F=—S—) by oxidation with MCPBA or other methods described in Scheme 1. The nitro group may then be reduced with Pd/C to reduce both the nitro and the olefin.

Compounds of formula 2-4 (AA=NH$_2$) are then converted to compounds of Formula 2-5 (which also represent compounds of Formulae I if no further modifications are required) as described in Scheme 1.

Compounds of formula 2-5 may be further modified to provide additional compounds of Formula I. For example, in cases where F is —NQ$_a$Q$_b$R$^3$—, Q$_a$Q$_b$=a direct bond, and R$_3$ represents a BOC protecting group (CO$_2$tBu), the BOC group may be removed according to standard methodology such as trifluoroactic acid (TFA) in DCM (Greene and Wuts, ibid.) to provide a secondary amine that can then be further derivatized to provide compounds of Formula I. Further derivatization includes, but is not limited to: reactions with aldehydes or ketones in the presence of a reducing agent such as sodium triacetoxyborohydride to provide compounds of Formula II where F=—NCH$_2$R$^3$ (A. F. Abdel-Magid, ibid.); with acid chlorides or with carboxylic acids and an amide bond forming reagent (as described in Scheme 1) to provide compounds of formula II where F=—NCOR$^3$; with sulfonyl chlorides (as described in Scheme 1) to provide compounds of Formula I where F=—NSO$_2$R$_a$; with isocyanates(as described in Scheme 1) to provide compounds of Formula II where F=—NCONR$_a$R$_b$; or subjected to metal-catalyzed substitution reactions as outlined in Scheme I to provide compounds of Formula I where F=—NR$^3$. (S. L. Buchwald, et al, ibid.; J. H. Hartwig, ibid.) For the above example, R$_a$ and R$_b$ are independently hydrogen, alkyl, cycloalkyl, haloalkyl, aryl, aralkyl, heteroaryl and heteroaralkyl.

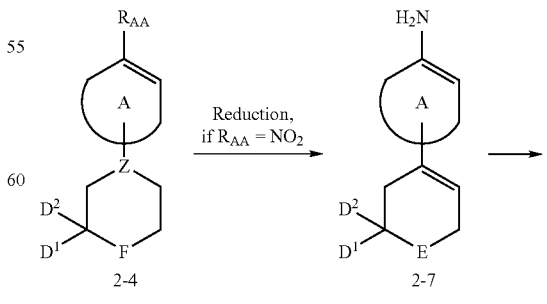

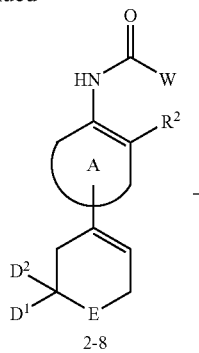

2-8

Scheme 2b illustrates a modification of Scheme 2a to synthesize partially unsaturated compounds of Formula I. E represents $-NQ_aQ_bR^3-$, $-O-(D^1=D^2=H)$, $-S-(D^1=D^2=H)$, $-SO-(D^1=D^2=H)$, or $-SO_2-(D^1=D^2=H)$, and $R_{AA}$ represents $-NH_2$ or $-NO_2$. Compounds of formula 2-4 are prepared as shown in Scheme 2. If $R_{AA}=-NO_2$, the nitro group must be reduced by a method that does not reduce olefins, such as iron and ammonium chloride. If $R_{AA}$ of formula 2-4 is an amino group then no step is necessary and compounds of formula 2-4 are also compounds of formula 2-7. To prepared compounds of formula 2-7 where $E=-SO_2-$ or $-SO-$, the oxidation of the sulfide must be performed on compound 2-4 where $R_{AA}=-NO_2$ as described above, followed by nitro reduction.

III. Methods of Preparation

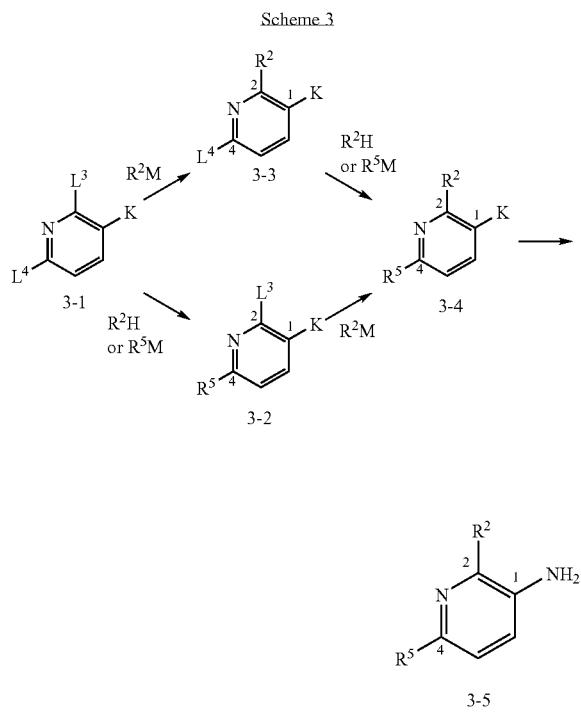

Scheme 3 illustrates the preparation of intermediates for the synthesis of compounds of Formula I, where ring A is pyridyl, and $R^5$ is the optional substitution on ring A or one of the heterocyclic substituents as defined in Formula I. $K=NH_2$ or other functional groups such as $NO_2$, COOH or COOR which can eventually be converted to amino group by known literature methods such as reductions for $NO_2$ (as discussed for Scheme 1) or Curtius rearrangement for COOH (for a review, see *Organic Reactions*, 3: 337 (1947)). $L^3$ and $L^4$ are halogens. (K=COOH can also be formed from K=COOR by simple base- or acid-catalyzed hydrolysis.)

In general, the selectivity and order in introducing $R^2$ and $R^5$ can be achieved by the relative reactivity of the halogens $L^3$ and $L^4$ chosen in compound (3-1), the intrinsic selectivity of the heterocycle and/or the reaction conditions employed. An example of using the relative reactivity of the halogens $L^3$ and $L_4$ in selectively introducing $R^2$ and $R^5$ would include the situation where, in compounds of Formula 3-1 where $L^3$ is a fluoro group and $L^4$ is a bromo group, selective displacement of the fluoro group by a nucleophile can be achieved followed by substitution of the remaining bromo group by metal-catalyzed substitution chemistry (such as Suzuki or Stille cross-coupling reactions as further outlined below). Similarly in compounds of Formula 3-1 where one of $L^3$ and $L^4$ is an iodo group and the other is a bromo or chloro group, selective metal-catalyzed substitution chemistry (such as Suzuki or Stille cross-coupling reactions or Buchwald/Hartwig aminations as further discussed below) on the iodo group can be achieved followed by replacement of the remaining bromo or chloro group by another metal-catalyzed substitution reaction.

As illustrated in Scheme 3, leaving group $L^3$ in Formula 3-1 can be first substituted to obtain compounds of Formula 3-3 or leaving group $L^4$ can be first substituted to obtain compound of Formula 3-2. Compounds 3-2 or 3-3 can then be reacted to displace $L^3$ or $L^4$ to furnish the compound of Formula 3-4.

Thus, a direct nucleophilic displacement or metal-catalyzed amination of compound of Formula 3-1 with a secondary amine, ammonia or a protected amine such as tert-butyl carbamate (for review, see Modern Amination Methods: Ricci, A., Ed.; Wiley-VCH: Weinheim, 2000), can be used to introduce $R^5$ in Formulae 3-2 or 3-3 where $R^5$ is a primary or secondary amine, amino group ($NH_2$), and amine equivalent or a protected amino group. Metal-catalyzed coupling of compound 3-1 with boronic acids or boronates esters (Suzuki reaction, M=boronic acid group or boronate ester group) or with organotin compounds (Stille reaction, M=SnR_3, where R=alkyl and the other substituents as defined above, as described in Scheme I can provide compounds of Formulae 3-2 or 3-3.

Compound 3-2 can be further converted to compound 3-4 by a metal-catalyzed Suzuki or Stille coupling as described above. $L^4$ in compound 3-3 also subsequently can be substituted with $R^5$ to obtain compounds of Formula 3-4, again, by a direct nucleophilic substitution or metal-catalyzed reaction with a nucleophile or by the same metal-catalyzed cross-coupling reaction as described above. When $R^5$ in the formulae (3-2, 3-3 or 3-4) is a protected amine and K not an amino group, it can be deprotected to unmask the amino functionality. This amino functionality can then be further derivatized as described in Scheme 1. When the K group in Formula 3-4 is not an amino group (such as functionality described above), it can be converted to an amino group according to known literature methods (see, for example Comprehensive Organic Transformations: Larock, R. S.; Wiley and Sons Inc., USA, 1999) and the resulting amine 3-5 can be employed in amide bond formation reactions as described in Scheme (1) to obtain the compounds in Formula I. When K in Formula 3-4 is an amino group it can be directly used in amide coupling as described above.

Scheme 4a

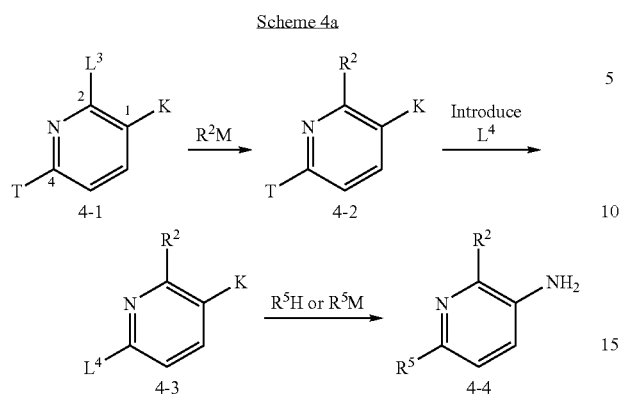

Scheme 4b

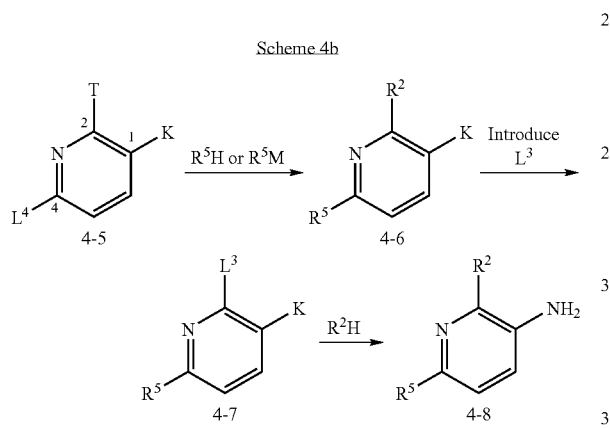

Schemes 4a and 4b illustrate the preparation of intermediates to be further modified according to Scheme 3 starting from a monohalo-substituted compound of Formulae 4-1 and 4-5 by introducing the second leaving group after the replacement of the first one has been completed. These can also be used for the synthesis of compounds of Formula I where ring A is a pyridine and $R^5$ is either the optional substitution on Ring A or one of the heterocyclic substituents. As in Scheme 3, the remaining positions on the pyridine ring can be substituted as described in Formula I. K=$NH_2$ or other functional groups such as $NO_2$, COOH or COOR which can eventually be converted to amino group by known literature methods such as reductions or Curtius rearrangement as described in Scheme 3. $L^3$ and $L^4$ are halogens. In these compounds, T is either H or is a functional group such as OH that can be converted to leaving groups $L^3$ or $L^4$ such as halogen, triflate or mesylate by known literature methods (see, for example, Nicolai, E., et al., *J. Heterocyclic Chemistry*, 31, (73), (1994)). Displacement of $L^3$ in compound of Formula 4-1 or $L^4$ in Formula 4-5 by methods described in Scheme 3, can yield compounds of Formulae 4-2 and 4-6. At this point, the substituent T of compounds 4-2 or 4-6 can be converted to a leaving group $L^4$ or $L^3$ (preferably a halogen) by standard methods to provide compounds of Formulae 4-3 and 4-5. For example, when T=OH, the preferred reagents to effect this transformation are thionyl chloride, $PCl_5$, $POCl_3$ or $PBr_3$ (see, for examples, Kolder, den Hertog., *Recl. Trav. Chim. Pays-Bas*; 285, (1953), and Iddon, B, et. al., *J. Chem. Soc. Perkin Trans. 1.*, 1370, (1980)). When T=H, it can be directly halogenated (preferably brominated) to provide compounds of Formulae 4-3 or 4-7 (see, for example, Canibano, V. et al., *Synthesis*, 14, 2175, (2001)). The preferred conditions for bromination are NBS in a suitable solvent such as DCM or acetonitrile.

The compounds of Formulae 4-3 or 4-7 can be converted to compounds of Formulae 4-4 or 4-8 by introduction of the remaining groups $R^2$ or $R^5$, respectively, by the methods described above and then on to compounds of Formula I, by the methods described in Scheme 3 for conversion of compounds of Formulae 3-4 and 3-5 to compounds of Formula I.

EXAMPLE 1

5-Cyano-furan-2-carboxylic acid

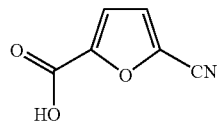

To a flask with a stir bar and Vigreaux column under Ar was added 2-formyl-5-furancarboxylic acid (2.8 g, 20 mmol), hydroxylamine hydrochloride (2.7 g, 40 mmol), and dry pyridine (50 mL). The mixture was heated to 85° C., acetic anhydride (40 mL) was added and the mixture was stirred for 3 h. After cooling to 60° C., water (250 mL) was added and the mixture was stirred at RT for 70 h. The mixture was acidified to pH 2 with concentrated hydrochloric acid and extracted with 3:1 dichloromethane-isopropanol (8×100 mL). The combined organic layers were washed with water (100 mL), brine (100 mL), dried over anh sodium sulfate and concentrated in vacuo to afford the title compound as a tan solid (1.26 g, 46%). $^1$H-NMR (CD$_3$OD; 400 MHz): δ 14.05 (br s, 1H), 7.74 (d, 1H, J=3.8 Hz), 7.42 (d, 1H, J=3.8 Hz).

EXAMPLE 2

4-Cyano-1H-pyrrole-2-carboxylic acid

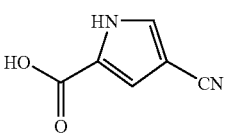

The title compound was prepared by the literature procedure (Loader and Anderson, *Canadian J. Chem.* 59: 2673 (1981)). $^1$H-NMR (CDCl$_3$; 400 MHz): δ 12.70 (br s, 1H), 7.78 (s, 1H), 7.13 (s, 1H).

EXAMPLE 3

4-Cyano-1-(2-trimethylsilanyl-ethoxymethyl)-1H-imidazole-2-carboxylate potassium salt

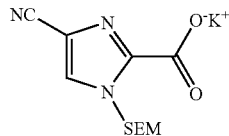

a) 1-(2-Trimethylsilanyl-ethoxymethyl)-1H-imidazole-4-carbonitrile

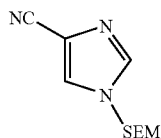

A flask charged with imidazole-4-carbonitrile (0.5 g, 5.2 mmol) (*Synthesis*, 677, 2003), 2-(trimethylsilyl)ethoxymethyl chloride (SEMCl) (0.95 mL, 5.3 mmol), $K_2CO_3$ (1.40 g, 10.4 mmol), and acetone (5 mL) was stirred for 10 h at RT. The mixture was diluted with EtOAc (20 mL) and washed with water (20 mL) and brine (20 mL) and the organic layer dried over $MgSO_4$. The crude product was eluted from a 20-g SPE cartridge (silica) with 30% EtOAc/hexane to give 0.80 g (70%) of the title compound as a colorless oil. Mass spectrum (CI (CH4), m/z) Calcd. for $C_{10}H_{17}N_3OSi$, 224.1 (M+H), found 224.1.

b) 2-Bromo-1-(2-trimethylsilanyl-ethoxymethyl)-1H-imidazole-4carbonitrile

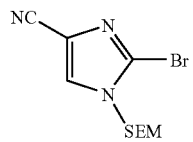

To a solution of 1-(2-trimethylsilanyl-ethoxymethyl)-1H-imidazole-4-carbonitrile (0.70 g, 3.1 mmol) (as prepared in the previous step) in $CCl_4$ (10 mL) was added NBS (0.61 g, 3.4 mmol) and AIBN (cat), and the mixture heated at 60° C. for 4 h. The reaction was diluted with EtOAc (30 mL) and washed with $NaHCO_3$ (2×30 mL) and brine (30 mL) and the organic layer was dried over $Na_2SO_4$ and then concentrated. The title compound was eluted from a 20-g SPE cartridge (silica) with 30% EtOAc/hexane to give 0.73 g (77%) of a yellow solid. Mass spectrum (CI (CH4), m/z) Calcd. for $C_{10}H_{16}BrN_3OSi$, 302.0/304.0 (M+H), found 302.1/304.1.

c) 4-Cyano-1-(2-trimethylsilanyl-ethoxymethyl)-1H-imidazole-2-carboxylic acid ethyl ester

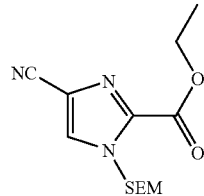

To a solution of 2-bromo-1-(2-trimethylsilanyl-ethoxymethyl)-1H-imidazole-4-carbonitrile (0.55 g, 1.8 mmol) (as prepared in the previous step) in THF (6 mL) at −40° C. was added drop wise a solution of 2M i-PrMgCl in THF (1 mL). The reaction was allowed to stir for 10 min at −40° C. and then cooled to −78° C., and ethyl cyanoformate (0.3 g, 3.0 mmol) was added. The reaction allowed to attain RT and stirred for 1 h. The reaction was quenched with satd aq $NH_4Cl$, diluted with EtOAc (20 mL) and washed with brine (2×20 mL), and the organic layer was dried over $Na_2SO_4$ and then concentrated. The title compound was eluted from a 20-g SPE cartridge (silica) with 30% EtOAc/hexane to give 0.4 g (74%) of a colorless oil. Mass spectrum (ESI, m/z): Calcd. for $C_{13}H_{21}N_3O_3Si$, 296.1 (M+H), found 296.1.

d) 4-Cyano-1-(2-trimethylsilanyl-ethoxymethyl)-1H-imidazole-2-carboxylate potassium salt To a solution of 4-cyano-1-(2-trimethylsilanyl-ethoxymethyl)-1H-imidazole-2-carboxylic acid ethyl ester (0.4 g, 1.3 mmol) (as prepared in the previous step) in ethanol (3 mL) was added a solution of 6M KOH (0.2 mL) and the reaction was stirred for 10 min and then concentrated to give 0.40 g (100%) of the title compound as a yellow solid. $^1$H-NMR (400 MHz, $CD_3OD$) δ 7.98 (s, 1H), 5.92 (s, 2H), 3.62 (m, 2H), 0.94 (m, 2H), 0.00 (s, 9H). Mass spectrum (ESI-neg, m/z) Calcd. for $C_{11}H_{17}N_3O_3Si$, 266.1 (M-H), found 266.0.

EXAMPLE 4

5-Cyano-furan-2-carboxylic acid [4-(4-methyl-piperazin-1-yl)-2-(3-methyl-thiophen-2-yl)-phenyl]-amide

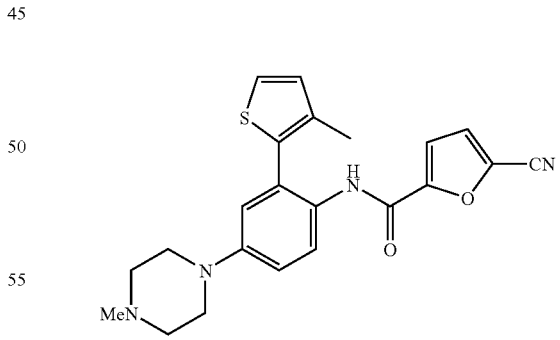

a) 1-(3-Bromo-4-nitro-phenyl)-4-methyl-piperazine

2-Bromo-4-fluoronitrobenzene (949 mg, 4.31 mmol) was added in two portions to neat N-methypiperazine (8 mL) at 0° C. and allowed to warm to room temperature. The reaction was heated to 60° C. for 1 h, and then it was diluted with 50 mL of EtOAc and poured into $H_2O$ (50 mL). The layers were separated and the organic layer was washed with satd aq $NaHCO_3$, dried ($Na_2SO_4$), and concentrated in vacuo to afford 580 mg (45%) of the title compound as a yellow solid: Mass spectrum (ESI, m/z): Calcd. for $C_{11}H_{14}BrN_3O_2$, 300.0 (M+H), found 300.1.

b) 4,4,5,5-Tetramethyl-2-(3-methyl-thiophen-2-yl)-[1,3,2]dioxaborolane

To a stirred solution of 2-bromo-3-methythiophene (337 mg, 1.9 mmol) in 8 mL of THF at −40° C. was added n-BuLi (0.8 mL, 2.5 M/hexanes), and the reaction was allowed to stir for 30 min. At this time 2-isopropoxy-4,4,5,5-tetramethyl-[1,3,2]dioxaborolane (775 μL, 3.8 mmol) was added, and the reaction was allowed to warm to ambient temperature, and stirring was continued for 1 h. The reaction was then cooled to 0° C. and quenched with satd aq $NaHCO_3$ (10 mL). The mixture was poured into EtOAc (100 mL), washed with $H_2O$ (2×50 mL), dried ($Na_2SO_4$) and concentrated in vacuo. Purification of the residue by silica gel preparative thin layer chromatography (20% EtOAc-hexanes) afforded 224 mg (53%) of the title compound as an oil. $^1$H-NMR ($CDCl_3$; 400 MHz): δ 1.36 (s, 12H), 2.5 (s, 3H), 6.99 (d, 1H, J=4.8 Hz), 7.50 (d, 1H, J=4.8 Hz).

c) 1-Methyl-4-[3-(3-methyl-thiophen-2-yl)-4-nitro-phenyl]-piperazine

To a flask containing 1-(3-bromo-4-nitro-phenyl)-4-methyl-piperazine (68 mg, 0.2 mmol, as prepared in Example 4, step (a)), 4,4,5,5-tetramethyl-2-(3-methyl-thiophen-2-yl)-[1,3,2]dioxaborolane (61 mg, 0.27 mmol, as prepared in the previous step) and $Pd(PPh_3)_4$ (14 mg, 6 mol %) was charged toluene (3 mL), ethanol (3 mL) and 2M $Na_2CO_3$ (4 mL). The resultant mixture was heated at 80° C. for 2 h and then poured into EtOAc (25 mL). The organic layer was separated, dried ($Na_2SO_4$) and concentrated in vacuo. Purification by silica gel preparative thin layer chromatography (EtOAc) afforded 40 mg (63%) of the title compound as a light yellow solid. Mass spectrum (ESI, m/z): Calcd. for $C_{16}H_{19}N_3O_2S$, 318.1 (M+H), found 318.2.

d) 5-Cyano-furan-2-carboxylic acid [4-(4-methyl-piperazin-1-yl)-2-(3-methyl-thiophen-2-yl)-phenyl]-amide 1-Methyl-4-[3-(3-methyl-thiophen-2-yl)-4-nitro-phenyl]-piperazine (60 mg, 0.18 mmol, as prepared in the previous step) was stirred with 40 mg 5% Pd—C in MeOH (5 mL) under $H_2$ (1 atm) for 2 h. The reaction was filtered through Celite and concentrated in vacuo to afford 40 mg (72%) of 4-(4-methyl-piperazin-1-yl)-2-(3-methyl-thiophen-2-yl)-phenylamine as a brown solid, which was used immediately without further purification. Using a procedure similar to Example 9, step (c), 4-(4-methyl-piperazin-1-yl)-2-(3-methyl-thiophen-2-yl)-phenylamine (40 mg, 0.13 mmol) was allowed to react with 5-cyano-furan-2-carbonyl chloride (30 mg, 0.19 mmol, as prepared in Example 9, step (c)) in the presence of DIEA (61 μL, 0.34 mmol) to afford 18.9 mg (36%) of the title compound as a yellow solid. $^1$H-NMR ($CDCl_3$; 400 MHz): δ 2.13 (s, 3H), 2.38 (s, 3H), 2.59-2.62 (m, 4H), 3.24-3.27 (m, 4H), 6.92 (d, 1H, J=2.8 Hz), 7.06 (d, 1H, J=5.1Hz), 7.15 (d, 1H, J=3.7 Hz), 7.19 (d, 1H, J=3.7 Hz), 7.02 (dd, 1H, J=2.8, 9.0 Hz), 7.42 (d, 1H, J=5.1 Hz), 8.11 (s, 1H), 8.34 (d, 1H, J=9.0 Hz); Mass spectrum (ESI, m/z): Calcd. for $C_{22}H_{22}N_4O_2S$, 407.1 (M+H), found 407.1.

EXAMPLE 5

5-Cyano-furan-2-carboxylic acid [4-(4-methyl-piperazin-1-yl)-2-(4-methyl-thiophen-3-yl)-phenyl]-amide

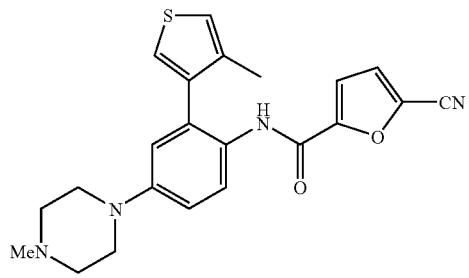

a) 4,4,5,5-Tetramethyl-2-(2-methyl-thiophen-3-yl)-[1,3,2]dioxaborolane

Using a procedure similar to Example 4, step (b), 3-bromo-4-methylthiophene (571 mg, 3.2 mmol) was treated with n-BuLi (1.41 mL, 2.5M/hexanes) and then allowed to react with 2-isopropoxy-4,4,5,5-tetramethyl-[1,3,2]dioxaborolane (775 μL, 3.8 mmol) to afford 189 mg (26%) of the title compound as a colorless oil. $^1$H-NMR ($CDCl_3$; 400 MHz): δ 1.32 (s, 12H), 2.42 (s, 3H), 6.90-6.91 (m, 1H), 7.84 (d, 1H, J=2.9 Hz).

b) 1-Methyl-4-[3-(4-methyl-thiophen-3-yl)-4-nitro-phenyl]-piperazine

Using a procedure similar to Example 4, step (c), 1-(3-bromo-4-nitro-phenyl)-4-methyl-piperazine (162 mg, 0.54 mmol), 4,4,5,5-tetramethyl-2-(2-methyl-thiophen-3-yl)-[1,3,2]dioxaborolane (145 mg, 0.64 mmol) and $Pd(PPh_3)_4$ (37 mg, 6 mol %) were allowed to react to afford 108 mg (71%) of the title compound as a yellow solid. $^1$H-NMR ($CDCl_3$; 400 MHz): δ 2.02 (s, 3H), 2.37 (s, 3H), 2.55-2.57 (m, 4H), 3.42-3.45 (m, 4H), 6.66 (d, 1H, J=2.8 Hz), 6.87 (s, 1H), 6.99-7.00 (m, 1H), 7.09 (d, 1H, J=3.2 Hz), 8.13 (d, 1H, J=9.2 Hz).

c) 4(4-Methyl-piperazin-1-yl)-2-(4methyl-thiophen-3-yl)-phenylamine

Using a procedure similar to Example 4, step (d), 1-methyl-4-[3-(4-methyl-thiophen-3-yl)-4-nitro-phenyl]-piperazine (100 mg, 0.32 mmol) was stirred with 80 mg 5% Pd—C under $H_2$ to afford 82 mg (89%) of the title compound as a dark oil, which was used immediately without further purification spectrum (ESI, m/z): Calcd. for $C_{16}H_{21}N_3S$, 288.15 (M+H), found 288.1.

d) 5-Cyano-furan-2-carboxylic acid [4-(4-methyl-piperazin-1-yl)-2-(4-methyl-thiophen-3-yl)-phenyl]-amide Using a procedure similar to Example 9, step (c), 5-cyano-furan-2-carbonyl chloride (64 mg, 0.41 mmol, as prepared in Example 9, step (c)) was allowed to react with 4-(4-methyl-piperazin-1-yl)-2-(4-methyl-thiophen-3-yl)-phenylamine (80 mg, 0.27 mmol, as prepared in the previous step) in the presence of DIEA (0.10 mL, 0.59 mmol) to afford 25.8 mg (24%) of the title compound as a yellow solid. $^1$H-NMR ($CDCl_3$; 400 MHz): δ 2.09 (s, 3H), 2.37 (s, 3H), 2.59-2.60 (m, 4H), 3.24-3.26 (m, 4H), 6.83 (d, 1H, J=2.9 Hz), 6.98-7.06 (m, 2H), 7.14-7.21 (m, 3H), 7.96 (s, 1H), 8.32 (d, 1H, J=9.0 Hz). Mass spectrum (ESI, m/z): Calcd. for $C_{22}H_{22}N_4O_2S$, 407.1 (M+H), found 407.1.

EXAMPLE 6

4-Cyano-1H-imidazole-2-carboxylic acid {2-cyclohex-1-enyl-4-[1-(2-hydroxy-1-hydroxymethyl-ethyl)-piperidin-4-yl]-phenyl}-amide trifluoroacetic acid salt

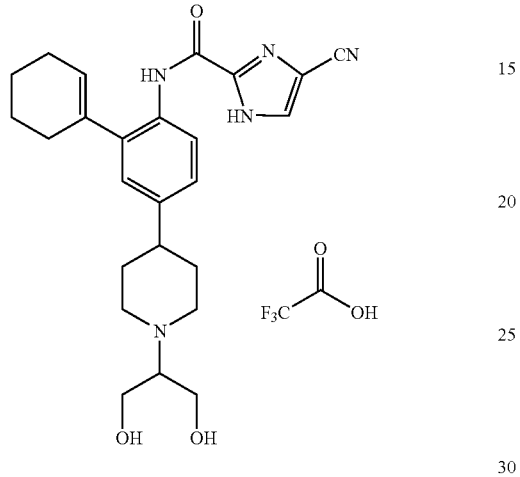

a) 4-Cyano-1H-imidazole-2-carboxylic acid {2-cyclohex-1-enyl-4-[1-(2,2-dimethyl-[1,3]dioxan-5-yl)-piperidin-4-yl]-phenyl}-amide To a slurry of 4-cyano-1H-imidazole-2-carboxylic acid (2-cyclohex-1-enyl-4-piperidin-4-yl-phenyl)-amide trifluoroacetic acid salt (81 mg, 0.16 mmol, as prepared in Example 14, step (b)) in $CH_2Cl_2$ (3 mL) was added $NEt_3$ (33 μL, 0.24 mmol). The solution was then treated with 2,2-dimethyl-[1,3]dioxan-5-one (31 mg, 0.24 mmol) and the reaction was allowed to stir for 3 h. At this time $NaBH(OAc)_3$ (51 mg, 0.24 mmol) was added in one portion, and the reaction was allowed to stir for an additional 4 h. The reaction was diluted with $H_2O$ (10 mL) and extracted with EtOAc (2×25 mL). The organic extracts were dried ($Na_2SO_4$) and concentrated in vacuo. Purification by silica gel preparative thin layer chromatography (10% MeOH—$CHCl_3$) afforded 22 mg (28%) of the title compound as an off-white semi-solid. Mass spectrum (ESI, m/z): Calcd. for $C_{28}H_{35}N_5O_3$, 490.2 (M+H), found 490.6.

b) 4-Cyano-1H-imidazole-2-carboxylic acid {2-cyclohex-1-enyl-4-[1-(2-hydroxy-1-hydroxymethyl-ethyl)-piperidin-4-yl]-phenyl}-amide trifluoro-acetic acid To a solution of 4-cyano-1H-imidazole-2-carboxylic acid {2-cyclohex-1-enyl-4-[1-(2,2-dimethyl-[1,3]dioxan-5-yl)-piperidin-4-yl]-phenyl}-amide (22 mg, 0.04 mmol, as prepared in the previous step) in THF—$H_2O$ (1 mL, 4:1 v/v) was added TFA (0.4 mL), and the reaction was allowed to stir for 1 h. Removal of the solvent under vacuum afforded 14 mg (60%) of the title compound as an amber foam. $^1$H-NMR ($CD_3OD$, 400 MHz): δ 1.78-1.90 (m, 4H), 2.03-2.16 (m, 3H), 2.29 (br s, 4H), 2.88-2.96 (m, 1H), 3.37-3.40 (m, 1H), 3.46-3.53 (m, 2H), 3.74-3.78 (m, 3H), 5.83 (s, 1H), 7.13 (d, 1H, J=2.0 Hz), 7.22 (dd, 1H, J=2.0, 8.4 Hz), 8.03 (s, 1H), 8.17 (d, 1H, J=8.4 Hz); Mass spectrum (ESI, m/z): Calcd. for $C_{25}H_{31}N_5O_3$, 450.2 (M+H), found 450.2.

EXAMPLE 7

4-Cyano-1H-imidazole-2-carboxylic acid {2-cyclohex-1-enyl-4-[1-(2-morpholin-4-yl-acetyl)-piperidin-4-yl]-phenyl}-amide

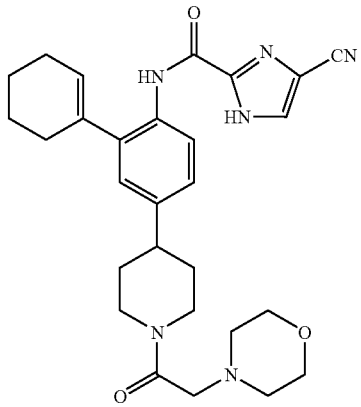

To a solution of morpholin-4-yl-acetic acid ethyl ester (117 mg, 0.67 mmol) in ethanol (4 mL) was added 6N KOH (110 μL, 0.67 mmol) via syringe and stirring was continued for 3 h. Concentration in vacuo afforded 122 mg (100%) of morpholin-4-yl-acetic acid potassium salt. To a mixture of morpholin-4-yl-acetic acid potassium salt (29 mg, 0.15 mmol), 4-cyano-1H-imidazole-2-carboxylic acid (2-cyclohex-1-enyl-4-piperidin-4-yl-phenyl)-amide trifluoroacetic acid salt (65.1 mg, 0.13 mmol, as prepared in Example 14, step (b)) and PyBroP (93 mg, 0.19 mmol) in $CH_2Cl_2$ (4 mL) was added DIEA (51 μL, 0.29 mmol) and the reaction was allowed to stir overnight. The reaction was diluted with $CH_2Cl_2$ (50 mL), washed with $H_2O$ (2×25 mL), dried ($Na_2SO_4$) and concentrated in vacuo. Purification of the crude product by silica gel preparative TLC afforded 8.1 mg (12%) of the title compound as a white solid. $^1$H-NMR ($CDCl_3$; 400 MHz): δ 1.68-2.04 (m, 5H), 2.20-2.29 (m, 4H), 2.53-2.78 (m, 5H), 3.09-3.23 (m, 6H), 3.35-3.40 (m, 1H), 3.72 (br s, 4H), 4.16-4.22 (m, 1H), 4.73-4.77 (m, 1H), 5.82 (s, 1H), 7.00 (s, 1H), 7.12 (dd, 1H, J=0.6, 8.0 Hz), 7.73 (s, 1H), 8.27 (d, 1H, J=8.1Hz), 9.48 (s, 1H); Mass spectrum (ESI, m/z): Calcd. for $C_{28}H_{34}N_6O_3$, 503.27 (M+H), found 503.1.

EXAMPLE 8

4-Cyano-1H-imidazole-2-carboxylic acid {2-cyclo-hex-1-enyl-4-[1-(3-morpholin-4-yl-propionyl)-piperidin-4-yl]-phenyl}-amide

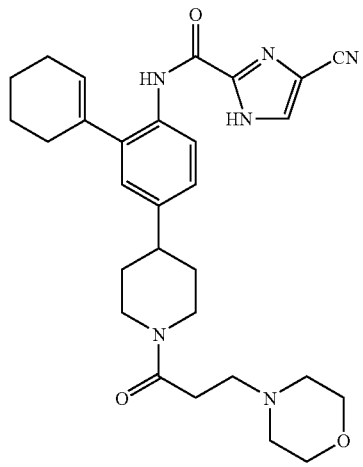

To a flask containing 3-morpholin-4-yl-propionic acid potassium salt (94 mg, 0.47 mmol, prepared from 3-morpholin-4-yl-propionic acid ethyl ester exactly as described in Example 7, 4-cyano-1H-imidazole-2-carboxylic acid (2-cyclohex-1-enyl-4-piperidin-4-yl-phenyl)-amide trifluoroacetic acid salt (179 mg, 0.36 mmol, as prepared in Example 14 (b)), EDCI (83 mg, 0.43 mmol), and HOBT (68 mg, 0.5 mmol) was added DMF (4 mL). To the stirred slurry was added DIEA (157 µL, 0.9 mmol) and the reaction was allowed to stir overnight. The reaction was diluted with $H_2O$ (10 mL) and extracted with EtOAc (2×25 mL). The combined organic extracts were dried ($Na_2SO_4$), concentrated in vacuo and the crude product was purified by silica gel preparative TLC to afford 10.4 mg (6%) of the title compound as a white solid.
$^1$H-NMR (CDCl$_3$; 400 MHz): δ 1.49-1.93 (m, 5H), 2.22-2.31 (m, 3H), 2.52 (br s, 4H), 2.58-2.63 (m, 3H), 2.74-2.76 (m, 4H), 3.10-3.17 (m, 2H), 3.72 (br s, 4H), 3.97-4.02 (m, 2H), 4.76-4.81 (m, 2H), 5.81-5.82 (m, 1H), 6.81-6.82 (m, 1H), 6.99-7.00 (m, 1H), 7.09-7.13 (m, 1H), 7.70 (s, 1H), 8.26 (d, 1H, J=8.2 Hz), 9.51 (s, 1H); Mass spectrum (ESI, m/z): Calcd. for $C_{29}H_{36}N_6O_3$, 517.28 M+H), found 517.3.

EXAMPLE 9

5-Cyano-furan-2-carboxylic acid [2'-methyl-5-(4-methyl-piperazin-1-yl)-biphenyl-2-yl]-amide

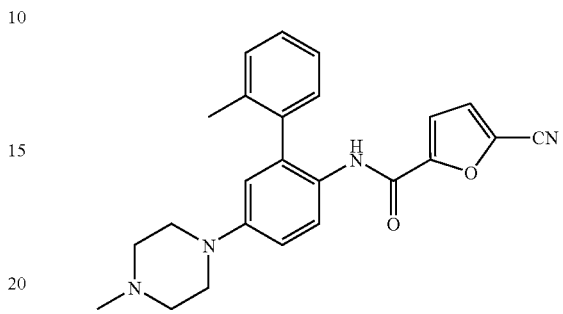

a) 1-(3-Bromo-4-nitro-phenyl)-4-methyl-piperazine

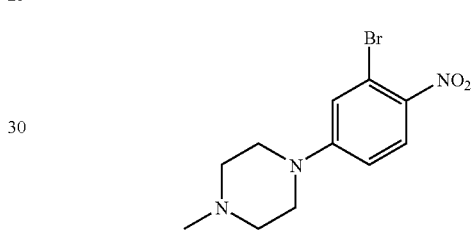

To a cooled (0° C.) solution of 1.00 g (4.55 mmol) of 2-bromo-4-fluoronitrobenzene (Oakwood) in 12 mL of EtOH was added 1.52 mL (13.7 mmol) of piperidine. The solution was stirred at 0° C. for 0.5 h and then at 60° C. for 4 h. The mixture was concentrated in vacuo, dissolved in EtOAc (60 mL), washed with water (3×100 mL) and brine (100 mL), and dried ($Na_2SO_4$). Concentration in vacuo and chromatography on a 50-g silica SPE column with 1-3% MeOH-dichloromethane afforded 1.06 g (77%) of the title compound as a tannish yellow solid. Mass spectrum (ESI, m/z): Calcd. for $C_{11}H_{14}BrN_3O_2$, 300.0 (M+H, $^{79}$Br), found 300.1.

b) 1-Methyl-4-(2'-methyl-6-nitro-biphenyl-3-yl)-piperazine

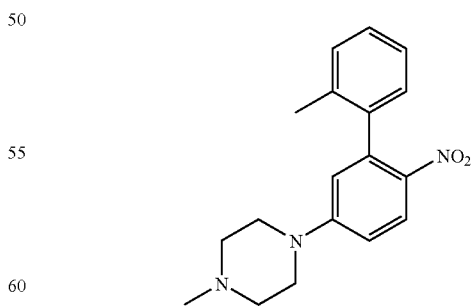

A mixture of 200mg (0.666 mmol) 1-(3-bromo-4-nitrophenyl)-4-methyl-piperazine (as prepared in the previous step), 136 mg (0.999 mmol) and 77.0 mg (0.0666 mmol) of tetrakis(triphenylphosphine)palladium (0) under Ar was added 4.0 mL of degassed dimethoxyethane (DME) and 400

μL (0.799 mmol) of 2.0 M aq Na₂CO₃. The mixture was heated with stirring under Ar at 80° C. for 14 h. The cooled (RT) mixture was concentrated and chromatographed on a 10-g silica SPE column with 1-5% MeOH in dichloromethane-hexane (1:1). The product fractions were treated with 80 mg of decolorizing carbon, filtered, concentrated, and then rechromatographed on a similar column with 1-3% EtOH-dichloromethane to afford 265 mg of the title compound as a yellow resin (75% purity by ¹H-NMR as a mixture with triphenylphosphine) that was used in the following reaction without further purification: Mass spectrum (ESI, m/z): Calcd. for $C_{11}H_{21}N_3O_3$, 312.2 (M+H), found 312.2.

c) 5-Cyano-furan-2-carboxylic acid [2'-methyl-5-(4-methyl-piperazin-1-yl)-biphenyl-2-yl]-amide

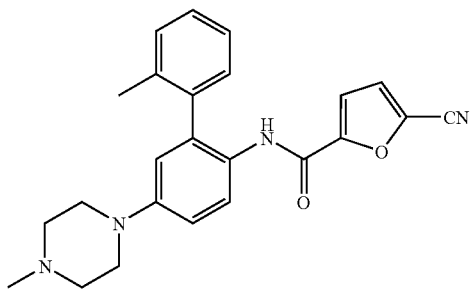

A mixture of 140 mg (0.337 mmol based on 75% purity) of 1-methyl-4-(2'-methyl-6-nitro-biphenyl-3-yl)-piperazine (as prepared in the previous step) and 70 mg of 10% palladium on carbon (Degussa type E101-NE/W, Aldrich, 50% by weight water) in 5 mL of THF was stirred vigorously under a balloon of hydrogen for 1 h. The mixture was filtered (Celite), washed with dichloromethane (2×2 mL), and the solution of the resulting aniline was placed under Ar and used immediately in the following reaction.

Simultaneously to the above reduction, 55.4 mg (0.404 mmol) of 5-cyanofuran-2-carboxylic acid (as prepared in Example 1) in 2.5 mL of anh dichloromethane under a CaSO₄ drying tube was treated with 52.9 μL (0.606 mmol) of oxalyl chloride followed by 10 μL of anh DMF. The solution was stirred for 25 min and quickly concentrated in vacuo at 20-25° C. The resulting 5-cyano-furan-2-carbonyl chloride was placed under high vacuum for 2-3 min and then immediately placed under Ar, cooled to 0° C. in an ice bath, and treated with the aniline solution produced above followed by 141 μL (0.808 mmol) of N,N-diisopropylethylamine (DIEA). After stirring for 30 min at RT, the mixture was concentrated in vacuo, and the resulting residue was chromatographed on a 20-g silica SPE column with 2-10% EtOH-dichloromethane to give a yellow resin (which was crystallized from EtOAc-hexane) to afford 17.2 mg (13%) of the pure title compound as a yellow solid along with 70.3 mg of impure title compound. The impure fraction was dissolved in 50 mL of EtOAc, washed with satd aq NaHCO₃-1 M K₂CO₃ (1:1, 2×20 mL) and brine (20 mL), dried (Na₂SO₄) and concentrated to afford 43.4 mg (32%) additional title compound as a crystalline yellow solid (total yield 45%). ¹H-NMR (CDCl₃; 400 MHz): δ 8.32 (d, 1H, J=9.0 Hz), 7.73 (br s, 1H), 7.34-7.54 (m, 3H), 7.25 (d, 1H, J=7.7 Hz), 7.12, 7.14 (AB q, 2H, J=3.7 Hz), 7.01 (dd, 1H, J=9.0, 2.8 Hz), 3.25-3.27 (m, 4H), 2.59-2.62 (m, 4H), 2.38 (s, 3H), and 2.15 (s, 3H). Mass spectrum (ESI, m/z): Calcd. for $C_{21}H_{24}N_4O_3$, 401.2 (M+H), found 401.1.

EXAMPLE 10

5-Cyano-furan-2-carboxylic acid [2'-fluoro-5-(4-methyl-piperazin-1-yl)-biphenyl-2-yl]-amide

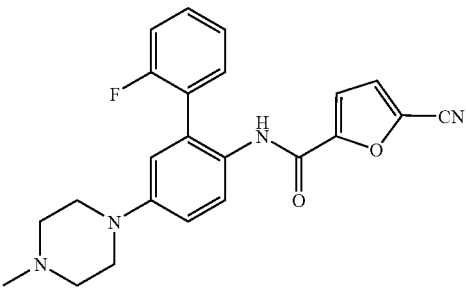

a) 1-(2'-Fluoro-6-nitro-biphenyl-3-yl)-4-methyl-piperazine

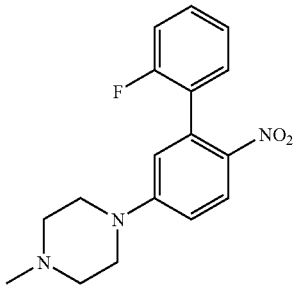

The procedure of Example 9, step (b) was followed using 75.0 mg (0.250 mmol) 1-(3-bromo-4-nitro-phenyl)-4-methyl-piperazine (as prepared in Example 9, step (a)), 136 mg (0.999 mmol) 2-fluorophenylboronic acid, 26.8 mg (0.0232 mmol) of tetrakis(triphenylphosphine)palladium (0) and 400 μL (0.799 mmol) of 2.0 M aq Na₂CO₃ in DME except the mnixture was heated for 22 h. Chromatography on a 5-g silica SPE column with 1-5% MeOH in dichloromethane-hexane (1:1) afforded 95.0 mg of the title compound (76% purity by ¹H-NMR as a mixture with triphenylphosphine) as a yellow resin that was used in the following reaction without further purification. Mass spectrum (ESI, m/z): Calcd. for $C_{17}H_{18}FN_3O_3$, 316.1 (M+H), found 316.2.

b) 5-Cyano-furan-2-carboxylic acid [2'-fluoro-5-(4-methyl-piperazin-1-yl)-biphenyl-2-yl]-amide

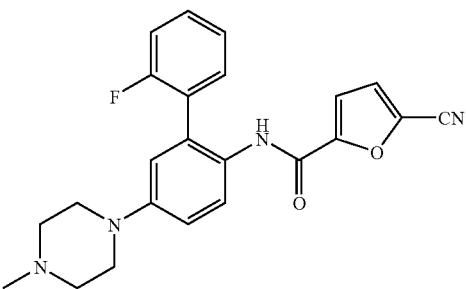

The procedure of Example 9, step (c) was followed using 93.2 mg (0.225 mmol based on 76% purity) of 1-(2'-fluoro-6-nitro-biphenyl-3-yl)-4-methyl-piperazine (as prepared in the previous step), 46 mg of 10% palladium on carbon, 37.0 mg (0.270 mmol) of 5-cyanofuran-2-carboxylic acid (as prepared in Example 1), 35.3 μL (0.405 mmol) of oxalyl chloride, 5.0 μL of anh DMF, and 94.1 μL (0.540 mmol) of DIEA. Chromatography on a 5-g silica SPE column with 1-4% MeOH-dichloromethane afforded 69.8 mg (77%) of the title compound as a yellow resin. $^1$H-NMR (CDCl$_3$; 400 MHz): δ 8.04 (d, 1H, J=9.0 Hz), 7.93 (br s, 1H), 7.434-7.48 (m, 1H), 7.37 (td, 1H, J=7.5, 1.8 Hz), 7.22-7.31 (m, 2H), 7.13, 7.18 (AB q, 2H, J=3.7 Hz), 7.02 (dd, 1H, J=9.0, 2.9 Hz), 6.88 (d, 1H, J=2.9 Hz), 3.24-3.27 (m, 4H), 2.57-2.60 (m, 4H), and 2.36 (s, 3H). Mass spectrum (ESI, m/z): Calcd. for C$_{23}$H$_{21}$FN$_4$O$_2$, 405.2 (M+H), found 405.2.

EXAMPLE 11

5-Cyano-furan-2-carboxylic acid [2-cyclohex-1-enyl-4-(4-methyl-piperazin-1-yl)-phenyl]-amide

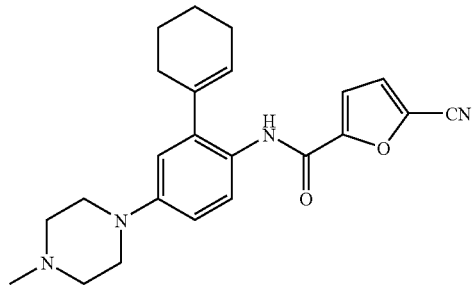

a) 1-(3-Cyclohex-1-enyl-4-nitro-phenyl)-4-methyl-piperazine

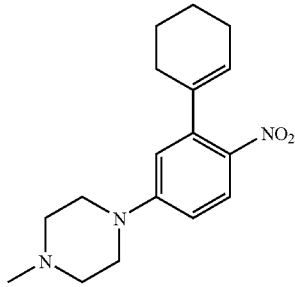

A mixture of 102 mg (0.340 mmol) 1-(3-bromo-4-nitro-phenyl)-4-methyl-piperazine (as prepared in Example 9, step (a)), 59.7 mg (0.474 mmol) cyclohexen-1-ylboronic acid, 43.8 mg (0.0379 mmol) of tetrakis(triphenylphosphine)palladium (0) under Ar was treated with 206 μL (0.412 mmol) of 2.0 M degassed aq Na$_2$CO$_3$, 0.6 mL degassed anh toluene and 0.2 mL degassed anh EtOH and the mixture was heated at 100° C. for 21 h. After cooling to RT, the mixture was poured into EtOAc (10 mL), washed with brine (10 mL), dried (Na$_2$SO$_4$) and concentrated in vacuo. Chromatography on a 5-g silica SPE column with 1-3% EtOH in dichloromethane afforded 126 mg of the title compound (74% purity by RP-HPLC (C18 column) as a mixture with triphenylphosphine) as a yellow oil that was used in the following reaction without further purification. Mass spectrum (ESI, m/z): Calcd. for C$_{17}$H$_{23}$N$_3$O$_3$, 302.2 (M+H), found 302.2.

b) 5-Cyano-furan-2-carboxylic acid [2-cyclohex-1-enyl-4-(4-methyl-piperazin-1-yl)-phenyl]-amide

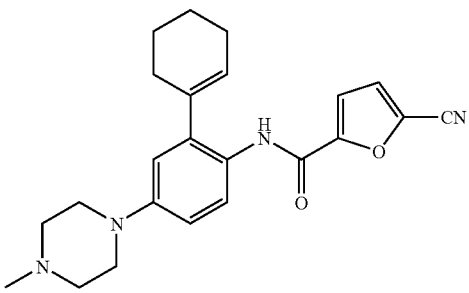

To 122 mg (0.299 mmol based on 74% purity) of 1-(3-cyclohex-1-enyl-4-nitro-phenyl)-4-methyl-piperazine (as prepared in the previous step) in 5.0 mL of EtOH-water (2:1) was added 83.8 mg (1.50 mmol) of iron powder and 160 mg (2.99 mmol) of NH$_4$Cl and the mixture refluxed under Ar for 12 h. An additional 83.8 mg (1.50 mmol) of iron powder was added, and the mixture was refluxed for 1 h. The mixture was poured into EtOAc (12 mL), filtered (Celite), washed with EtOAc (2×4 mL), concentrated in vacuo and dissolved in anh THF (4.0 mL). The resulting aniline solution was placed under Ar and used immediately in the following reaction.

61.6 mg (0.449 mmol) of 5-cyanofuran-2-carboxylic acid (as prepared in Example 1) in 2.5 mL of anh dichloromethane under a CaSO$_4$ drying tube was treated with 60.0 μL (0.688 mmol) of oxalyl chloride followed by 10 μL of anh DMF. The solution was stirred for 25 min and quickly concentrated in vacuo at 20-25° C. The residue was placed under high vacuum for 2-3 min and then immediately placed under Ar, cooled to 0° C. in an ice bath and treated with the aniline solution produced above followed by 104 μL (0.598 mmol) of DIEA. After stirring 30 min at RT, the mixture was concentrated in vacuo, dissolved in EtOAc (20 mL), washed with 1M K$_2$CO$_3$ (2×10 mL) and brine (10 mL), dried (Na$_2$SO$_4$) and concentrated in vacuo. The resulting residue was chromatographed on a 10-g silica SPE column with 1-4% MeOH-dichloromethane to give a yellow resin which was then crystallized from Et$_2$O-hexane to afford 84.7 mg (72%) of the title compound as a crystalline yellow solid. $^1$H-NMR (CDCl$_3$; 400 MHz): δ 8.57 (br s, 1H), 8.26 (d, 1H, J=9.0 Hz), 7.20, 7.23 (AB q, 2H, J=3.7 Hz), 6.86 (dd, 1H, J=9.0, 2.9 Hz), 6.74 (d, 1H, J=2.9 Hz), 5.84-5.85 (m, 1H), 3.20-3.22 (m, 4H), 2.57-2.59 (m, 4H), 2.36 (s, 3H), 2.23-2.30 (m, 4H) and 1.79-1.84 (m, 4H). Mass spectrum (ESI, m/z): Calcd. for C$_{23}$H$_{26}$N$_4$O$_2$, 391.2 (M+H), found 391.2.

EXAMPLE 12

5-Cyano-furan-2-carboxylic acid[2-(3,6-dihydro-2H-pyran-4-yl)-4-(4-methyl-piperazin-1-yl)-phenyl-amide

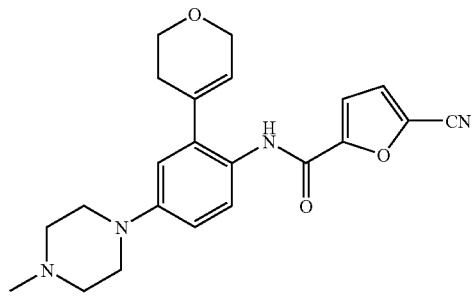

a) 1-[3-(3,6-Dihydro-2H-pyran-4-yl)-4-nitro-phenyl]-4-methyl-piperazine

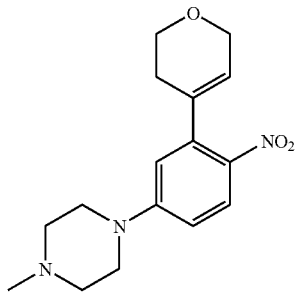

1-(3-Bromo-4-nitro-phenyl)-4-methyl-piperazine (as prepared in Example 9, step (a)) (225.1 mg, 0.79 mmol), K$_2$CO$_3$ (310.9 mg, 2.25 mmol) and 4-(4,4,5,5-tetramethyl-[1,3,2]dioxaborolan-2-yl)-3,6-dihydro-2H-pyran (Murata, M., et al, Synthesis, 778, (2000)) (157 mg, 0.75 mmol) in dioxane (5 mL) was heated at 80° C. overnight under Ar. The reaction mixture was allowed to cool to RT, concentrated, and the resulting residue was chromatographed on silica (10% EtOAc/hexane-20% MeOH/EtOAc) to obtain the title compound (82 mg, 36%). $^1$H-NMR (CDCl$_3$; 400 MHz): δ 8.04 (d, 1H, J=9.4 Hz), 6.78 (dd, 1H, J=9.4, 2.6 Hz), 6.58 (m, 1H, J=2.6 Hz), 5.58 (m, 1H), 4.34 (m, 2H), 3.95 (t, 2H, J=5.3 Hz), 3.46 (m, 4H), 2.57 (m, 4H), 2.38 (s, 3H), 2.30 (m, 2H).

b) 5-Cyano-furan-2-carboxylic acid[2-(3,6-dihydro-2H-pyran-4-yl)-4-(4-methyl-piperazin-1-yl)-phenyl-amide

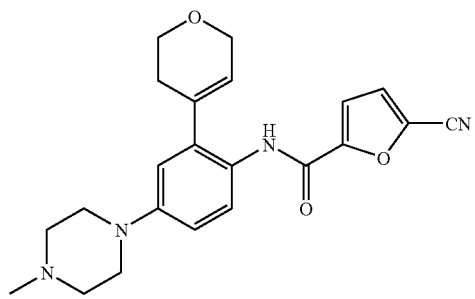

1-[3-(3,6-Dihydro-2H-pyran-4-yl)-4-nitro-phenyl]-4-methyl-piperazine (as prepared in previous step) (80 mg, 0.26 mmol) was converted to the corresponding amine using a procedure similar to Example 4, step (d), and coupled with 5-cyano-furan-2-carbonyl chloride as prepared in Example 9, step (c) (obtained from 137 mg, 1.00 mmol of 5-cyano-furan-2-carboxylic acid as prepared in Example 1) in CH$_2$Cl$_2$ (2 mL) at 0° C. The product was isolated by flash chromatography on silica (50% EtOAc/hexane-10% MeOH/EtOAc) to obtain the title compound (62.2 mg, 60%). $^1$H-NMR (CDCl$_3$; 400 MHz): 6 8.35 (br s, 1H), 8.12 (d, 1H each, J=8.76 Hz), 7.24 (d, 1H, J=5.08 Hz), 7.19 (d, 1H, J=5.08 Hz), 6.88 (dd, 1H, J=8.76, 2.7 Hz), 6.73 (d, 1H, J=2.7 Hz), 5.88 (br s, 1H), 4.34 (m, 2H), 3.94 (t, 2H, J=5.3 Hz), 3.23 (m, 4H), 2.59 (m, 4H), 2.38 (br s, 5H). LC-MS (ESI, m/z): Calcd. for C$_{22}$H$_{24}$N$_4$O$_3$, 393.1 (M+H), found 393.2.

EXAMPLE 13

4-Cyano-1H-pyrrole-2-carboxylic acid (2-cyclohex-1-enyl-4-piperidin-4-yl-phenyl)-amide trifluoroacetic acid salt

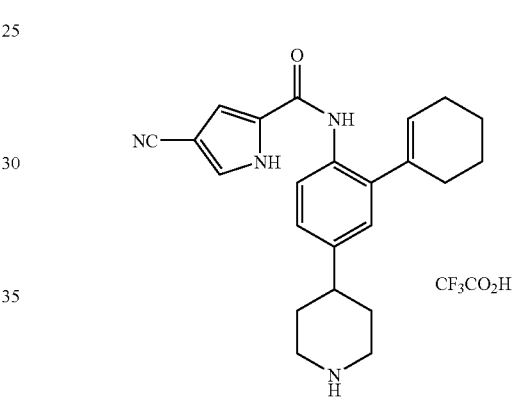

a) 4-(4-Amino-phenyl)-3,6-dihydro-2H-pyridine-1-carboxylic acid tert-butyl ester

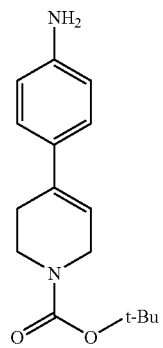

The title compound was prepared by Suzuki coupling of 4-(4,4,5,5-tetramethyl-[1,3,2]dioxaborolan-2-yl)-phenylamine with 4-trifluoromethanesulfonyloxy-3,6-dihydro-2H-pyridine-1-carboxylic acid tert-butyl ester (Synthesis, 993, (1991)) according to the procedure in Example 35, step (b). Mass spectrum (ESI, m/z): Calcd. for C$_{16}$H$_{22}$N$_2$O$_2$, 275.2 (M+H), found 275.1.

b) 4-(4-Amino-phenyl)-piperidine-1-carboxylic acid tert-butyl ester

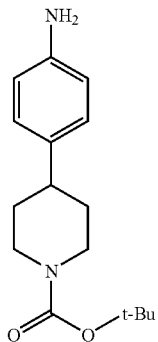

A solution of 4-(4-amino-phenyl)-3,6-dihydro-2H-pyridine-1-carboxylic acid tert-butyl ester (0.35 g, 1.2 mmol) (as prepared in the previous step) in methanol was hydrogenated over 10% Pd/C at 20 psi for 1 h. The solution was filtered and concentrated to give 0.35 g (100%) of the title compound as a yellow solid: Mass spectrum (ESI, m/z): Calcd. for $C_{16}H_{24}N_2O_2$, 277.2 (M+H), found 277.1.

c) 4-(4-Amino-3-bromo-phenyl)-piperidine-1-carboxylic acid tert-butyl ester

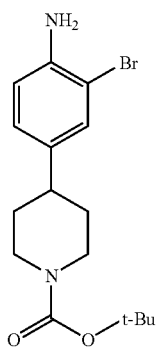

To a solution of 4-(4-amino-phenyl)-piperidine-1-carboxylic acid tert-butyl ester (0.20 g, 0.71 mmol) (as prepared in the previous step) in DCM (3 mL) was added N-bromosuccinimide (NBS) (0.13 g, 0.71 mmol), and the reaction stirred at RT for 10 h. The reaction was diluted with EtOAc (10 mL) and washed with NaHCO$_3$ (2×10 mL) and brine (10 mL). Concentration of the organic layer gave 0.26 g (100%) of the title compound as a yellow foam. Mass spectrum (ESI, m/z): Calcd. for $C_{16}H_{23}BrN_2O_2$, 355.1 (M+H), found 355.1.

d) 4-(4-Amino-3-cyclohex-1-enyl-phenyl)-piperidine-1-carboxylic acid tert-butyl ester

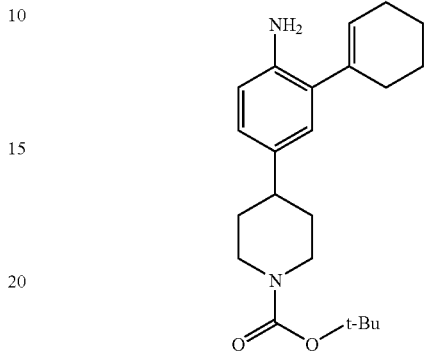

A flask was charged with 4-(4-amino-3-bromo-phenyl)-piperidine-1-carboxylic acid tert-butyl ester (0.13 g, 0.36 mmol) (as prepared in the previous step), cyclohex-1-enyl boronic acid (0.060 g, 0.48 mmol), Pd(PPh$_3$)$_4$ (0.04 g, 10 mol %), aqueous 2M Na$_2$CO$_3$ (1.5 mL), ethanol (1.5 mL), and toluene (3 mL), and heated at 80° C. for 3 h. The reaction was diluted EtOAc (10 mL), washed with NaHCO$_3$ (2×10 mL) and brine (10 mL), and the organic layer was dried over Na$_2$SO$_4$ and then concentrated. The title compound was eluted from a 20-g SPE cartridge (silica) with 30% EtOAc/hexane to give 0.10 g (85%) of the title compound as a yellow oil. Mass spectrum (ESI, m/z): Calcd. for $C_{22}H_{32}N_2O_2$, 357.2 (M+H), found 357.1.

e) 4-Cyano-1H-pyrrole-2-carboxylic acid (2-cyclohex-1-enyl-4-piperidin-4-yl-phenyl)-amide trifluoroacetic acid salt A flask was charged with 4-(4-amino-3-cyclohex-1-enyl-phenyl)-piperidine-1-carboxylic acid tert-butyl ester (0.050 g, 0.14 mmol) (as prepared in the previous step), 4-cyano-1H-pyrrole-2-carboxylic acid (0.019 g, 0.14 mmol)(as prepared in Example 2), EDCI (0.040 g, 0.21 mmol), HOBt (0.019 g, 0.14 mmol), DIEA (0.073 mL, 0.42 mmol), and DCM (0.5 mL) and stirred at 25° C. for 10 h. The reaction was loaded directly on a 10-g solid phase extraction (SPE) cartridge (silica) and the resulting intermediate was eluted with 30% EtOAc/hexane. This compound was stirred at RT for 1 h in 50% TFA/DCM (2 mL) and then concentrated and purified by RP-HPLC (C18), eluting with 30-50% CH$_3$CN in 0.1% TFA/H$_2$O over 12 min to give the title compound (0.052 g, 77%). $^1$H-NMR (400 MHz, CD$_3$OD): δ 7.59 (s, 1H), 7.50 (d, 1H), 7.22 (d, 1H), 7.16 (m, 2H), 5.74 (m, 1H), 3.54. (m, 2H), 3.16 (m, 2H), 2.94 (m, 1H), 2.29 (m, 2H), 2.15 (m, 4H), 1.92 (m, 2H), 1.72 (m, 4H). Mass spectrum (ESI, m/z): Calcd. for $C_{23}H_{26}N_4O$, 375.2 (M+H), found 375.1.

EXAMPLE 14

4-Cyano-1H-imidazole-2-carboxylic acid (2-cyclohex-1-enyl-4-piperidin-4-yl-phenyl)-amide trifluoroacetic acid salt

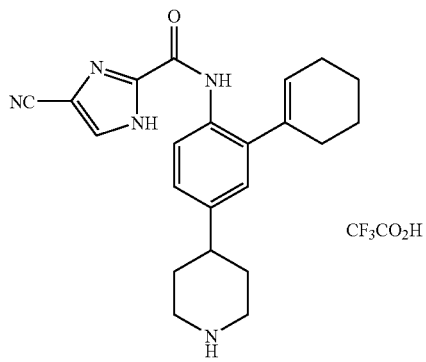

a) 4-(4-{[4-Cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester

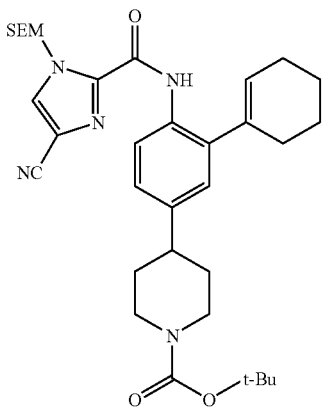

To a solution of 4-cyano-1-(2-trimethylsilanyl-ethoxymethyl)-1H-imidazole-2-carboxylate potassium salt (3.34 g, 10.9 mmol) (as prepared in Example 3, step (d)) in 20 mL DCM was added DIEA (3.8 mL, 21.8 mmol) and PyBroP (5.6 g, 12.0 mmol), and the reaction stirred at 25° C. for 15 min. A solution of 4-(4-amino-3-cyclohex-1-enyl-phenyl)-piperidine-1-carboxylic acid tert-butyl ester (3.9 g, 10.9 mmol) (as prepared in Example 13, step (d)) in 10 mL DCM was added and the reaction stirred for 8 h at 25° C. The reaction was diluted EtOAc (60 mL) and washed with NaHCO$_3$ (2×60 mL) and brine (100 mL) and the organic layer was dried over Na$_2$SO$_4$ and then concentrated. The title compound was purified by flash chomatography (silica gel, 2% EtOAc/DCM) to give 5.5 g (85%) of the title compound as a yellow oil. Mass spectrum (ESI, m/z): Calcd. for C$_{33}$H$_{47}$N$_5$O$_4$Si, 606.2 (M+H), found 606.2.

b) 4-Cyano-1H-imidazole-2-carboxylic acid (2-cyclohex-1-enyl-4-piperidin-4-yl-phenyl)-amide trifluoroacetic acid salt To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (1.5 g, 2.5 mmol) (as prepared in the previous step) in 10 mL of DCM and 0.3 mL EtOH was added 3 mL of TFA and the solution stirred for 3 h at 25° C. The reaction was diluted with 5 mL of EtOH and then concentrated. The residue was crystallized from methanol and ethyl ether to give 0.85 g (70%) of the title compound as a white solid. $^1$H-NMR (400 MHz, CD$_3$OD) δ 8.18 (d, 1H), 8.04 (s, 1H), 7.22 (dd, 1H), 7.12 (d, 1H), 5.76 (m, 1H), 3.54. (m, 2H), 3.16 (m, 2H), 2.92 (m, 1H), 2.30 (m, 4H), 2.10 (m, 2H), 1.75 (m, 6H). Mass spectrum (ESI, m/z): Calcd. for C$_{22}$H$_{25}$N$_5$O, 376.2 (M+H), found 376.2.

EXAMPLE 15

4-Cyano-1H-pyrrole-2-carboxylic acid [4-(1-acetyl-piperidin-4-yl)-2-cyclohex-1-enyl-phenyl]-amide

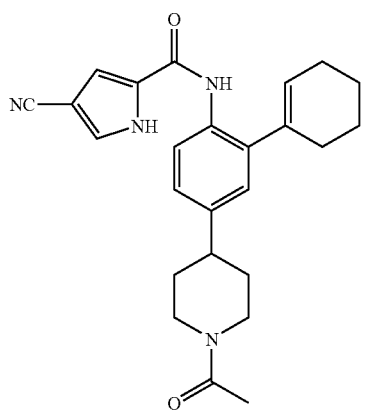

The title compound was prepared from 4-cyano-1H-pyrrole-2-carboxylic acid (2-cyclohex-1-enyl-4-piperidin-4-yl-phenyl)-amide trifluoroacetic acid salt (as prepared in Example 13, step (e)) according to the procedure in Example 37. $^1$H-NMR (400 MHz, CDCl$_3$) δ 10.82 (s, 1H), 8.28 (d, 1H), 8.18 (s, 1H), 7.48 (d, 1H), 7.16 (dd, 1H), 7.02 (s, 1H), 6.72 (s, 1H), 5.88 (m, 1H), 4.82 (m, 1H), 3.98. (m, 1H), 3.20 (m, 1H), 2.70 (m, 2H), 2.29 (m, 4H), 2.18 (s, 3H), 1.80 (m, 8H). Mass spectrum (ESI, m/z): Calcd. for C$_{25}$H$_{28}$N$_4$O$_2$, 417.2 (M+H), found 417.1.

EXAMPLE 16

4-Cyano-1H-imidazole-2-carboxylic acid [4-(1-acetyl-piperidin-4-yl)-2-cyclohex-1-enyl-phenyl]-amide

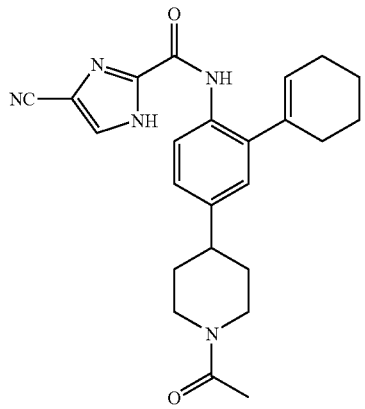

The title compound was prepared from 4-cyano-1H-imidazole-2-carboxylic acid (2-cyclohex-1-enyl-4-piperidin-4- yl-phenyl)-amide trifluoroacetic acid salt (as prepared in Example 13, step (b)) according to the procedure in Example 37: $^1$H-NMR (400 MHz, CDCl$_3$) δ 13.12 (br s, 1H), 9.58 (s, 1H), 8.34 (d, 1H), 7.76 (s, 1H), 7.21 (dd, 1H), 7.05 (d, 1H), 5.86 (s, 1H), 4.84 (m, 2H), 4.00 (m, 1H), 3.22 (m, 1H), 2.72 (m, 2H), 2.30 (m, 4H), 2.21 (s, 3H), 1.80 (m, 8H). Mass spectrum (ESI, m/z): Calcd. for C$_{24}$H$_{27}$N$_5$O$_2$, 418.2 (M+H), found 418.1.

EXAMPLE 17

4-Cyano-1H-imidazole-2-carboxylic acid [2-(4-methyl-cyclohex-1-enyl)-4-piperidin-4-yl-phenyl]-amide trifluoroacetic acid salt

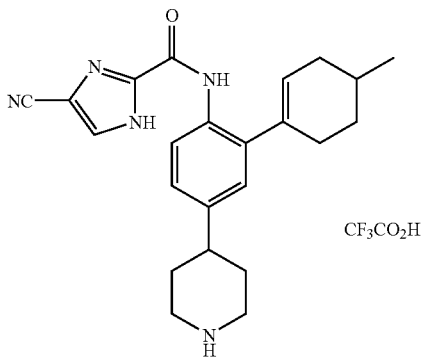

The title compound was prepared from 4-cyano-1-(2-trimethylsilanyl-ethoxymethyl)-1H-imidazole-2-carboxylate potassium salt (as prepared in Example 3, step (d)) and 4-[4-amino-3-(4-methyl-cyclohex-1-enyl)-phenyl]-piperidine-1-carboxylic acid tert-butyl ester (prepared according to the procedure in Example 13, step (d), substituting 4-methyl-1-cyclohex-1-enyl boronic acid for cyclohex-1-enyl boronic acid) according to the procedure for Example 14: $^1$H-NMR (400 MHz, CD$_3$OD): δ 8.18 (d, 1H), 8.04 (s, 1H), 7.22 (dd, 1H), 7.12 (d, 1H), 5.80 (m, 1H), 3.54. (m, 2H), 3.18 (m, 2H), 2.94 (m, 1H), 2.30 (m, 3H), 2.12 (m, 2H), 1.92 (m, 5H), 1.54 (m, 1H), 1.12 (d, 3H). Mass spectrum (ESI, m/z): Calcd. for C$_{23}$H$_{27}$N$_5$O, 390.2 (M+H), found 390.2.

EXAMPLE 18

4-Cyano-1H-imidazole-2-carboxylic acid (2-cyclopent-1-enyl-4-piperidin-4-yl-phenyl)-amide trifluoroacetic acid salt

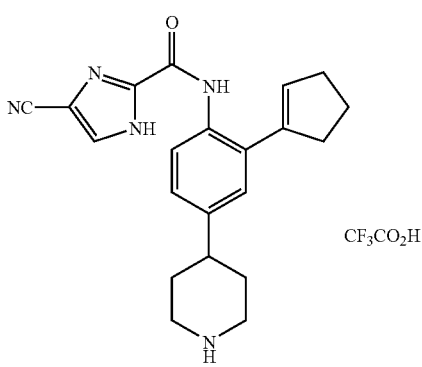

The title compound was prepared from 4-cyano-1-(2-trimethylsilanyl-ethoxymethyl)-1H-imidazole-2-carboxylate potassium salt (as prepared in Example 3, step (d)) and 4-(4-amino-3-cyclopent-1-enyl-phenyl)-piperidine-1-carboxylic acid tert-butyl ester (prepared according to the procedure in Example 13, step (d), substituting cyclopenten-1-yl boronic acid for cyclohex-1-enyl boronic acid) according to the procedure for Example 14. $^1$H-NMR (400 MHz, DMSO-d$_6$) δ 14.25 (br s, 1H), 10.00 (s, 1H), 8.36 (s, 1H), 7.72 (d, 1H), 7.18 (m, 2H), 6.06 (s, 1H), 4.12 (m, 1H), 3.42 (m, 2H), 3.18 (m, 2H), 3.00 (m, 3H), 2.80 (m, 2H), 1.92 (m, 5H). Mass spectrum (ESI, m/z): Calcd. for C$_{21}$H$_{23}$N$_5$O, 362.2 (M+H), found 362.2.

EXAMPLE 19

An alternate method for the synthesis of the intermediate described in Example 1 is described below.

5-Cyano-furan-2-carboxylic acid

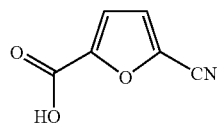

A 250-mL, three-neck, round-bottom flask equipped with a mechanical stirrer, a heating mantle, and a condenser was charged with 5-formyl-2-furancarboxylic acid (9.18 g, 65.6 mmol) and pyridine (60 mL). Hydroxylamine hydrochloride (5.01 g, 72.2 mmol) was added and the mixture was heated to 85° C. Acetic anhydride (40 mL) was added and the reaction was stirred at 85° C. for 3 h, after which time the solvent was evaporated at 40° C. under reduced pressure. The residue was dissolved in water, basified with 2.0 N NaOH solution to pH 9, and extracted with 4:1 dichloromethane/2-propanol until the pyridine was completely removed (5×200 mL). The aqueous solution was then acidified with 2.0 N HCl solution to pH 2, saturated with solid NaCl, and extracted with 4:1 dichloromethane/2-propanol (5×200 mL). The combined organic extracts were dried over Na$_2$SO$_4$ and concentrated in vacuo to dryness. The residue was crystallized from dichloromethane to give 6.80 g of the title compound as a white solid (76%). Mass spectrum (ESI-neg, m/z) Calcd. for C$_6$H$_3$NO$_3$, 136.0 (M−H), found 136.1. The $^1$H NMR spectrum was consistent with the assigned structure.

EXAMPLE 20

4-Cyano-1H-imidazole-2-carboxylic acid {2-cyclohex-1-enyl-4-[1-(2-methanesulfonyl-acetyl)-piperidin-4-yl]-phenyl}-amide

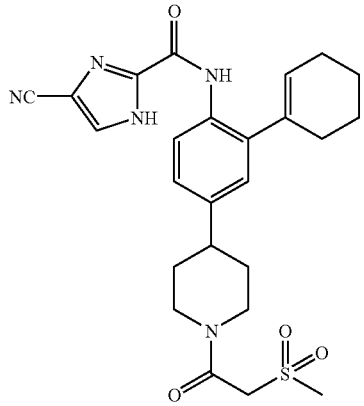

A flask was charged with methanesulfonyl-acetic acid (14 mg, 0.10 mmol), EDCI (30 mg, 0.15 mmol), HOBt (14 mg, 0.10 mmol), DIEA (36 µL, 0.20 mmol) and 0.5 mL DCM and stirred at 25° C. After 10 min, a solution containing 4-cyano-1H-imidazole-2-carboxylic acid (2-cyclohex-1-enyl-4-piperidin-4-yl-phenyl)-amide TFA salt (40 mg, 0.08 mmol) (as prepared in Example 20, step (b)) and NEt$_3$ (14 µL, 0.09 mmol) in 0.5 mL DCM was added and the reaction allowed to proceed for 10 h at 25° C. The reaction mixture was loaded on a 5-g SPE cartridge (silica) and the title compound was eluted with 10% EtOH/EtOAc to give 10 mg (25%) of a white solid. $^1$H-NMR (400 MHz, CDCl$_3$): δ 11.60 (br s, 1H), 9.52 (s, 1H), 8.30 (d, 1H), 7.74 (s, 1H), 7.60 (dd, 1H), 7.03 (d, 1H), 5.86 (m, 1H), 4.84 (m, 1H), 4.18 (s, 2H), 4.12 (m, 1H), 3.32 (m, 1H), 3.20 (s, 3H), 2.82 (m, 2H), 2.30 (m, 4H), 1.98 (m, 2H), 1.84 (m, 5H), 1.72 (m, 1H). Mass spectrum (ESI, m/z): Calcd. for C$_{25}$H$_{29}$N$_5$O$_4$S, 496.2 (M+H), found 496.2.

EXAMPLE 21

4-Cyano-1H-imidazole-2-carboxylic acid [2-cyclohex-1-enyl-4-(1-pyridin-2-ylmethyl-piperidin-4-yl)-phenyl]-amide trifluoroacetic acid salt

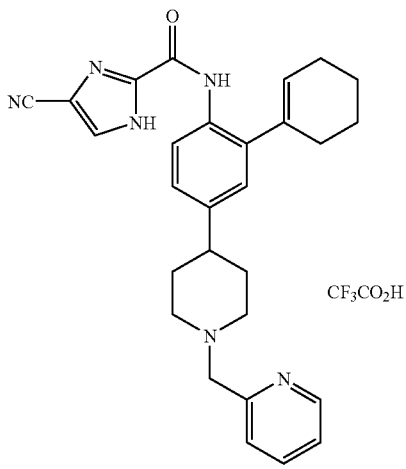

A flask was charged with 4-cyano-1H-imidazole-2-carboxylic acid (2-cyclohex-1-enyl-4-piperidin-4-yl-phenyl)-amide TFA salt (88 mg, 0.18 mmol) (as prepared in Example 14, step (b)), pyridine-2-carbaldehyde (17 µL, 0.21 mmol), NEt$_3$ (30 µL, 0.21 mmol), sodium triacetoxyborohydride (56 mg, 0.25 mmol) and 0.8 mL of 1,2-dichloroethane and stirred for 10 h at 25° C. The solvent was evaporated, and the title compound was purified by RP-HPLC (C18), eluting with 30-50% CH$_3$CN in 0.1% TFA/H$_2$O over 20 min to give 81 mg (78%) of a white solid. $^1$H-NMR (400 MHz, DMSO-d$_6$): δ 14.25 (br s, 1H), 9.90 (br s, 1H), 9.79 (s, 1H), 8.72 (s, 1H), 8.36 (s, 1H), 7.98 (m, 1H), 7.88 (dd, 1H), 7.58 (d, 1H), 7.52 (m, 1H), 7.20 (m, 1H), 7.12 (d, 1H), 5.76 (m, 1H), 4.56 (s, 2H), 3.40 (m, 2H), 3.18 (m, 2H), 2.88 (m, 1H), 2.20 (m, 4H), 2.00 (m, 4H), 1.72 (m, 4H). Mass spectrum (ESI, m/z): Calcd. for C$_{28}$H$_{30}$N$_6$O, 467.2 (M+H), found 467.2.

EXAMPLE 22

4-Cyano-1H-imidazole-2-carboxylic acid [2-(4-methyl-cyclohex-1-enyl)-4-(1-pyridin-2-ylmethyl-piperidin-4-yl)-phenyl]-amide trifluoroacetic acid salt

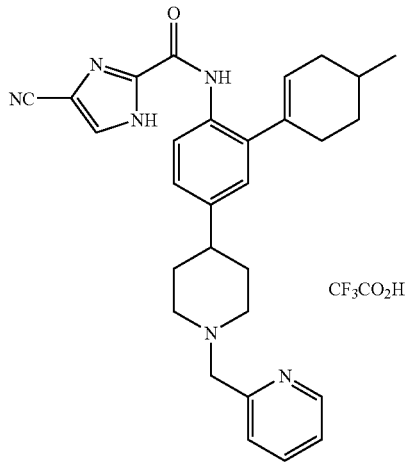

This compound was prepared according to the procedure in Example 21 from 4-cyano-1H-imidazole-2-carboxylic acid [2-(4-methyl-cyclohex-1-enyl)-4-piperidin-4-yl-phenyl]-amide (as prepared in Example 17) and pyridine-2-carbaldehyde. $^1$H-NMR (400 MHz, DMSO-d$_6$): δ 14.25 (br s, 1H), 9.90 (br s, 1H), 9.79 (s, 1H), 8.72 (s, 1H), 8.36 (s, 1H), 7.98 (m, 1H), 7.86 (dd, 1H), 7.54 (d, 1H), 7.52 (m, 1H), 7.20 (m, 1H), 7.12 (d, 1H), 5.74 (m, 1H), 4.56 (s, 2H), 3.40 (m, 2H), 3.18 (m, 2H), 2.88 (m, 1H), 2.48-2.22 (m, 3H), 2.18-2.06 (m, 4H), 1.98-1.82 (m, 3H), 1.52 (m, 1H), 1.02 (s, 3H). Mass spectrum (ESI, m/z): Calcd. for C$_{28}$H$_{32}$N$_6$O, 481.2 (M+H), found 481.2.

EXAMPLE 23

4-Cyano-1H-imidazole-2-carboxylic acid {2-cyclo-pent-1-enyl-4-[1-(1-methyl-1H-imidazol-2-ylm-ethyl)-piperidin-4-yl]-phenyl}-amide trifluoroacetic acid salt

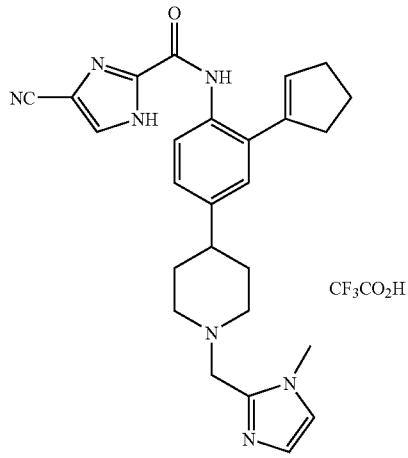

This compound was prepared from 4-cyano-1H-imidazole-2-carboxylic acid (2-cyclopent-1-enyl-4-piperidin-4-yl-phenyl)-amide TFA salt (as prepared in Example 18) and 1-methyl-1H-imidazole-2-carbaldehyde according to the procedure in Example 21. $^1$H-NMR (400 MHz, CD$_3$OD): δ 8.03 (m, 2H), 7.50 (d, 1H), 7.42 (s, 1H), 7.20 (m, 2H), 6.02 (m, 1H), 4.22 (s, 2H), 3.96 (s, 3H), 3.30 (m, 2H), 2.82-2.40 (m, 7H), 2.13-1.84 (m, 6H). Mass spectrum (ESI, m/z): Calcd. for C$_{26}$H$_{29}$N$_7$O, 456.2 (M+H), found 456.2.

EXAMPLE 24

4-{4-[(4Cyano-1H-imidazole-2-carbonyl)-amino]-3-cyclohex-1-enyl-phenyl}-piperidine-1-carboxylic acid amide

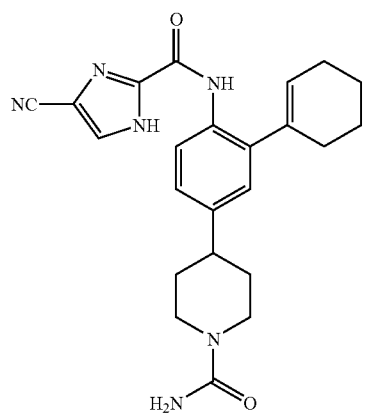

A flask was charged with 4-cyano-1H-imidazole-2-carboxylic acid (2-cyclohex-1-enyl-4-piperidin-4-yl-phenyl)-amide TFA salt (51 mg, 0.10 mmol) (as prepared in Example 14, step (b)), NEt$_3$ (22 μL, 0.15 mmol), trimethylsilyl isocyanate (16 μL, 0.11 mmol) and 1.0 mL of DCM and stirred for 10 h at 25° C. The solvent was evaporated and the title compound was purified by RP-HPLC (C18), eluting with 35-60% CH$_3$CN in 0.1% TFA/H$_2$O over 11 min to give 30 mg (70%) of a white solid. $^1$H-NMR (400 MHz, DMSO-d$_6$): δ 14.28 (br s, 1H), 9.76 (s, 1H), 8.34 (s, 1H), 7.84 (d, 1H), 7.18 (dd, 1H), 7.08 (d, 1H), 6.00 (br s, 2H), 5.72 (m, 1H), 4.18 (m, 2H), 2.80-2.60 (m, 3H), 2.24-2.10 (m, 4H), 1.80-1.60 (m, 6H), 1.50 (m, 2H). Mass spectrum (ESI, mnz): Calcd. for C$_{23}$H$_{26}$N$_6$O, 419.2 (M+H), found 419.0.

EXAMPLE 25

4-Cyano-1H-imidazole-2-carboxylic acid [2-cyclohex-1-enyl-4-(3,4,5,6-tetrahydro-2H-[1,2']bipyridinyl-4-yl)-phenyl]-amide trifluoroacetic acid salt

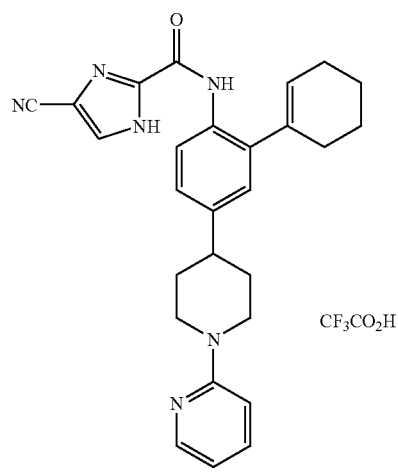

A flask was charged with 4-cyano-1H-imidazole-2-carboxylic acid (2-cyclohex-1-enyl-4-piperidin-4-yl-phenyl)-amide TFA salt (75 mg, 0.15 mmol) (as prepared in Example 14, step (b)), K$_2$CO$_3$ (84 mg, 0.60 mmol), 2-fluoropyridine (27 μL, 0.30 mmol) and 0.3 mL of N,N-dimethylacetamide and stirred for 8 h at 120° C. The reaction was diluted with 3 mL of H$_2$O and the title compound was purified by RP-HPLC (C18), eluting with 30-50% CH$_3$CN in 0.1% TFA/H$_2$O over 9 min to give 50 mg (75%) of a white solid. $^1$H-NMR (400 MHz, CD$_3$OD): δ 8.18 (d, 1H), 8.06 (m, 1H), 8.02 (s, 1H), 7.94 (dd, 1H), 7.48 (d, 2H), 7.22 (dd, 1H), 7.12 (d, 1H), 6.98 (t, 1H), 5.82 (m, 1H), 4.32 (m, 2H), 3.46 (m, 2H), 3.00 (m, 1H), 2.30 (m, 4H), 2.18 (m, 2H), 1.96-1.74 (m, 6H). Mass spectrum (ESI, m/z): Calcd. for C$_{27}$H$_{28}$N$_6$O, 453.2 (M+H), found 453.2.

EXAMPLE 26

4-Cyano-1H-imidazole-2-carboxylic acid {2-cyclohex-1-enyl-4-[1-(2-hydroxy-ethyl)-piperidin-4-yl]-phenyl}-amide trifluoroacetic acid salt

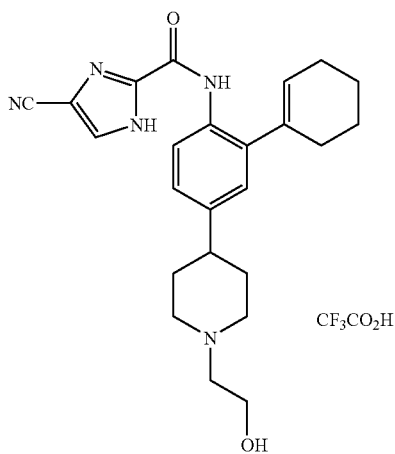

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), and hydroxy-acetaldehyde according to the procedure in Example 21. $^1$H-NMR (400 MHz, CD$_3$OD): δ 8.18 (d, 1H), 8.02 (s, 1H), 7.22 (dd, 1H), 7.14 (d, 2H), 5.82 (m, 1H), 3.94 (m, 2H), 3.74 (m, 2H), 3.30 (m, 2H), 3.18 (t, 2H), 2.92 (m, 1H), 2.30 (m, 4H), 2.20-1.98 (m, 4H), 1.96-1.74 (m, 4H). Mass spectrum (ESI, m/z): Calcd. for C$_{24}$H$_{29}$N$_5$O$_2$, 420.2 (M+H), found 420.2.

EXAMPLE 27

4-Cyano-1H-imidazole-2-carboxylic acid {4-[1-(2-cyano-ethyl)-piperidin-4-yl]-2-cyclohex-1-enyl-phenyl}-amide trifluoroacetic acid salt

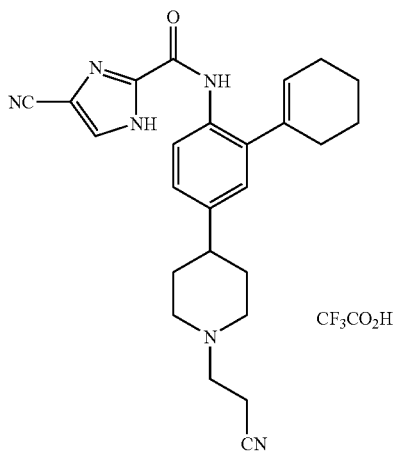

A flask was charged with 4-cyano-1H-imidazole-2-carboxylic acid (2-cyclohex-1-enyl-4-piperidin-4-yl-phenyl)-amide TFA salt (77 mg, 0.16 mmol) (as prepared in Example 14, step (b)), NEt$_3$ (24 μL, 0.16 mmol), acrylonitrile (12 μL, 0.18 mmol), 0.1 mL MeOH and 1.0 mL of 1,2-dichloroethane and stirred for 1 h at 80° C. The reaction was concentrated and the title compound was purified by RP-HPLC (C18), eluting with 30-50% CH$_3$CN in 0.1% TFA/H$_2$O over 12 min to give 83 mg (95%) of a white solid. $^1$H-NMR (400 MHz, CD$_3$OD): δ 8.18 (d, 1H), 8.06 (m, 1H), 7.22 (dd, 1H), 7.12 (d, 1H), 5.82 (m, 1H), 3.76 (m, 2H), 3.60 (m, 2H), 3.28 (t, 2H), 3.12 (t, 2H), 2.92 (m, 1H), 2.30 (m, 4H), 2.18-1.98 (m, 4H), 1.92-1.74 (m, 4H). Mass spectrum (ESI, m/z): Calcd. for C$_{25}$H$_{28}$N$_6$O, 429.2 (M+H), found 429.2.

EXAMPLE 28

4-Cyano-1H-imidazole-2-carboxylic acid [4-(1-carbamoylmethyl-piperidin-4-yl)-2-cyclohex-1-enyl-phenyl]-amide trifluoroacetic acid salt

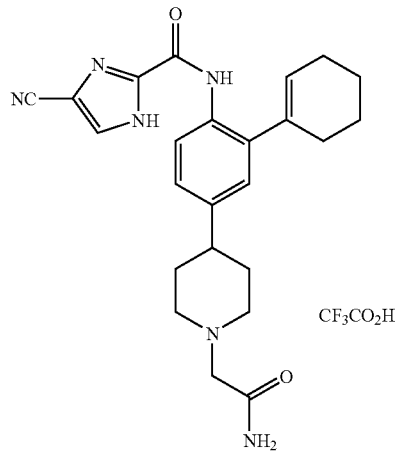

A flask was charged with 4-cyano-1H-imidazole-2-carboxylic acid (2-cyclohex-1-enyl-4-piperidin-4-yl-phenyl)-amide TFA salt (50 mg, 0.10 mmol) (as prepared in Example 14, step (b)), NEt$_3$ (32 μL, 0.23 mmol), 2-bromoacetamide (16 mg, 0.12 mmol), and 0.5 mL of DCM and stirred for 4 h at 25° C. The reaction was concentrated and the title compound was purified by RP-HPLC (C18), eluting with 30-50% CH$_3$CN in 0.1% TFA/H$_2$O over 12 min to give 42 mg (75%) of a white solid. $^1$H-NMR (400 MHz, DMSO-d$_6$): δ 14.28 (br s, 1H), 9.78 (s, 1H), 9.50 (br s, 1H), 8.34 (s, 1H), 8.00 (s, 1H), 7.88 (d, 1H), 7.72 (s, 1H), 7.18 (dd, 1H), 7.10 (d, 1H), 5.76 (m, 1H), 3.94 (s, 2H), 3.58 (m, 2H), 3.12 (m, 2H), 2.80 (m, 1H), 2.20 (m, 4H), 1.98 (m, 4H), 1.80 (m, 4H). Mass spectrum (ESI, m/z): Calcd. for C$_{24}$H$_{28}$N$_6$O$_2$, 433.2 (M+H), found 433.2.

EXAMPLE 29

4-Cyano-1H-imidazole-2-carboxylic acid {2-cyclohex-1-enyl-4-[1-(2-pyridin-2-yl-acetyl)-piperidin-4-yl]-phenyl}-amide trifluoroacetic acid salt

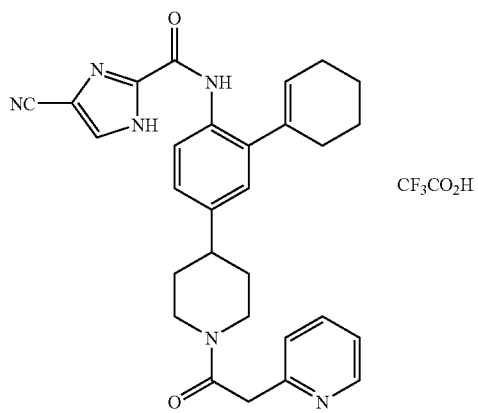

A flask was charged with 4-cyano-1H-imidazole-2-carboxylic acid (2-cyclohex-1-enyl-4-piperidin-4-yl-phenyl)-amide TFA salt (25 mg, 0.05 mmol) (as prepared in Example 14, step (b)), pyridin-2-yl-acetic acid hydrochloride (10 mg, 0.06 mmol), EDCI (12 mg, 0.06 mmol), HOBt (8.0 mg, 0.06 mmol), DIEA (36 ,uL, 0.20 mmol) and 0.2 mL DMF and stirred at 25° C. for 10 h. The reaction was diluted with 2 mL of H$_2$O and the title compound was purified by RP-HPLC (C18), eluting with 30-50% CH$_3$CN in 0.1% TFA/H$_2$O over 9 min to give 22 mg (70%) of a white solid. $^1$H-NMR (400 MHz, CD$_3$OD): δ 8.82 (d, 1H), 8.52 (t, 1H), 8.14 (d, 1H), 8.04 (s, 1H), 7.96 (m, 3H), 7.20 (dd, 1H), 7.10 (d, 1H), 5.82 (m, 1H), 4.68 (m, 1H), 4.32 (m, 2H), 4.18 (m, 1H), 3.40 (m, 1H), 2.88 (m, 2H), 2.30 (m, 4H), 2.06-1.60 (m, 8H). Mass spectrum (ESI, m/z): Calcd. for C$_{29}$H$_{30}$N$_6$O$_2$, 495.2.2 (M+H), found 495.2.

EXAMPLE 30

4-Cyano-1H-imidazole-2-carboxylic acid {2-cyclohex-1-enyl-4-[1-(2-pyridin-3-yl-acetyl)-piperidin-4-yl]-phenyl}-amide trifluoroacetic acid salt

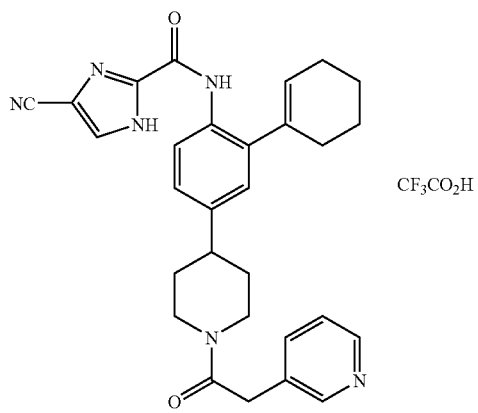

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using pyridin-3-yl-acetic acid. $^1$H-NMR (400 MHz, CD$_3$OD): δ 8.80 (m, 2H), 8.54 (d, 1H), 8.10 (d, 1H), 8.06 (t, 1H), 7.98 (s, 1H), 7.18 (dd, 1H), 7.08 (d, 1H), 5.78 (m, 1H), 4.68 (m, 1H), 4.20 (m, 1H), 4.18 (s, 2H), 3.36 (m, 1H), 2.84 (m, 2H), 2.28 (m, 4H), 2.06-1.70 (m, 7H), 1.62 (m, 1H). Mass spectrum (ESI, m/z): Calcd. for C$_{29}$H$_{30}$N$_6$O$_2$, 495.2 (M+H), found 495.2.

EXAMPLE 31

4-Cyano-1H-imidazole-2-carboxylic acid {2-cyclohex-1-enyl-4-[1-(2-pyridin-4-yl-acetyl)-piperidin-4-yl]-phenyl}-amide trifluoroacetic acid salt

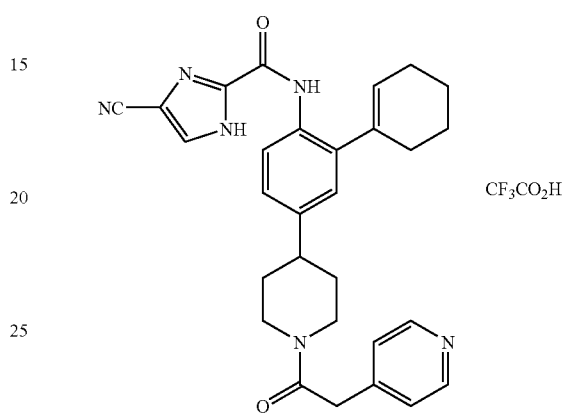

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using pyridin-4-yl-acetic acid. $^1$H-NMR (400 MHz, CD$_3$OD): δ 8.78 (d, 2H), 8.12 (d, 1H), 8.00 (m, 3H), 7.18 (dd, 1H), 7.08 (d, 1H), 5.80 (m, 1H), 4.66 (m, 1H), 4.22 (s, 2H), 4.18 (m, 1H), 3.34 (m, 1H), 2.84 (m, 2H), 2.24 (m, 4H), 2.00-1.70 (m, 7H), 1.64 (m, 1H). Mass spectrum (ESI, m/z): Calcd. for C$_{29}$H$_{30}$N$_6$O$_2$, 495.2 (M+H), found 495.2.

EXAMPLE 32

4-Cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide trifluoroacetic acid salt

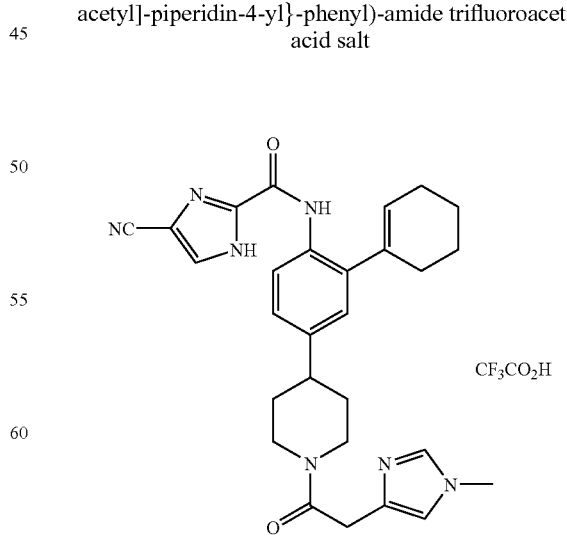

The title compound was prepared from 4-cyano-1H-imidazole-2-carboxylic acid (2-cyclohex-1-enyl-4-piperidin-4- yl-phenyl)-amide TFA salt (as prepared in Example 14, step (b)), according to the procedure in Example 29 using (1-methyl-1H-imidazol-4-yl)-acetic acid. ¹H-NMR (400 MHz, CD$_3$OD): δ 8.82 (s, 1H), 8.10 (d, 1H), 8.00 (s, 1H), 7.42 (s, 1H), 7.16 (dd, 1H), 7.06 (d, 1H), 5.80 (m, 1H), 4.66 (m, 1H), 4.12 (m, 1H), 4.04 (m, 2H), 3.92 (s, 3H), 3.28 (m, 1H), 2.82 (m, 2H), 2.26 (m, 4H), 2.00-1.70 (m, 7H), 1.64 (m, 1H). Mass spectrum (ESI, m/z): Calcd. for C$_{28}$H$_{31}$N$_7$O$_2$, 498.2 (M+H), found 498.2.

EXAMPLE 33

4-Cyano-1H-imidazole-2-carboxylic acid {2-cyclohex-1-enyl-4-[1-(2-1H-imidazol-4-yl-acetyl)-piperidin-4-yl]-phenyl}-amide trifluoroacetic acid salt

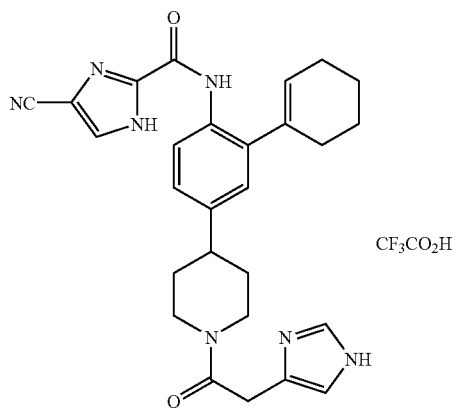

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using (1-methyl-1H-imidazol-4-yl)-acetic acid. ¹H-NMR (400 MHz, CD$_3$OD): δ 8.88 (s, 1H), 8.12 (d, 1H), 8.02 (s, 1H), 7.44 (s, 1H), 7.20 (dd, 1H), 7.10 (d, 1H), 5.82 (m, 1H), 4.70 (m, 1H), 4.18 (m, 1H), 4.06 (m, 2H), 3.36 (m, 1H), 2.84 (m, 2H), 2.30 (m, 4H), 2.00-1.70 (m, 7H), 1.64 (m, 1H). Mass spectrum (ESI, m/z): Calcd. for C$_{27}$H$_{29}$N$_7$O$_2$, 484.2 (M+H), found 484.2.

EXAMPLE 34

4-Cyano-1H-imidazole-2-carboxylic acid {2-cyclohex-1-enyl-4-[1-(2-morpholin-4-yl-ethyl)-piperidin-4-yl]-phenyl}-amide di-trifluoroacetic acid salt

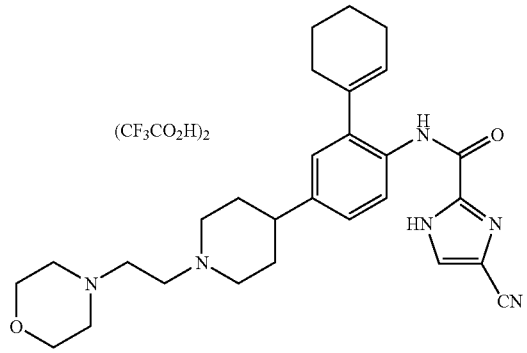

a) 4-Cyano-1-(2-trimethylsilanyl-ethoxymethyl)-1H-imidazole-2-carboxylic acid {2-cyclohex-1-enyl-4[1-(2-morpholin-4-yl-ethyl)-piperidin-4-yl]-phenyl}-amide

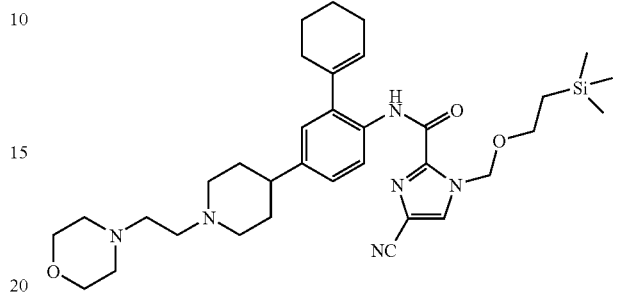

A flask was charged with 4-cyano-1-(2-trimethylsilanyl-ethoxymethyl)-1H-imidazole-2-carboxylic acid (2-cyclohex-1-enyl-4-piperidin-4-yl-phenyl)-amide TFA salt (830 mg, 1.34 mmol) (as prepared in Example 39, step (a)), K$_2$CO$_3$ (600 mg, 4.34 mmol), sodium iodide (40 mg, 0.27 mmol), 4-(2-chloro-ethyl)-morpholine hydrochloride (260 mg, 1.40 mmol), and 5.0 mL of N,N-dimethylacetamide and stirred for 8 h at 80° C. The reaction was diluted with EtOAc (50 mL) and washed with NaHCO$_3$ (2×50 mL), brine (50 mL) and concentrated. The title compound was purified by flash chomatography (silica gel, 5% MeOH/DCM) to give 650 mg (78%) of a white solid. Mass spectrum (ESI, m/z): Calcd. for C$_{34}$H$_{50}$N$_6$O$_3$Si, 619.4 (M+H), found 619.3.

b) 4-Cyano-1H-imidazole-2-carboxylic acid {2-cyclohex-1-enyl-4-[1-(2-morpholin-4-yl-ethyl)-piperidin-4-yl]-phenyl}-amide trifluoroacetic acid salt To a solution of 4-cyano-1-(2-trimethylsilanyl-ethoxymethyl)-1H-imidazole-2-carboxylic acid {2-cyclohex-1-enyl-4-[1-(2-morpholin-4-yl-ethyl)-piperidin-4-yl]-phenyl}-amide (650 mg, 1.05 mmol) (as prepared in the previous step) in 10 mL of DCM was added 0.3 mL of EtOH and 3.0 mL of TFA, and the reaction was allowed to proceed for 2 h at 25° C. The reaction was diluted with 10 mL of EtOH and concentrated. The title compound was purified by RP-HPLC (C18), eluting with 30-50% CH$_3$CN in 0.1% TFA/H$_2$O over 9 min to give 600 mg (80%) of a white solid. ¹H-NMR (400 MHz, CD$_3$OD): δ 8.18 (d, 1H), 8.04 (s, 1H), 7.24 (dd, 1H), 7.14 (d, 1H), 5.84 (m, 1H), 3.84 (m, 4H), 3.76 (m, 2H), 3.50 (m, 2H), 3.30-3.10 (m, 4H), 2.92 (m, 5H), 2.30 (m, 4H), 2.20-2.00 (m, 4H), 1.90-1.74 (m, 4H). Mass spectrum (ESI, m/z): Calcd. for C$_{28}$H$_{36}$N$_6$O$_2$, 489.2, found 489.2.

EXAMPLE 35

4-Cyano-1H-imidazole-2-carboxylic acid [2-(1,1-dioxo-1,2,3,6-tetrahydro-1λ⁶-thiopyran-4-yl)-4-piperidin-4-yl-phenyl]-amide

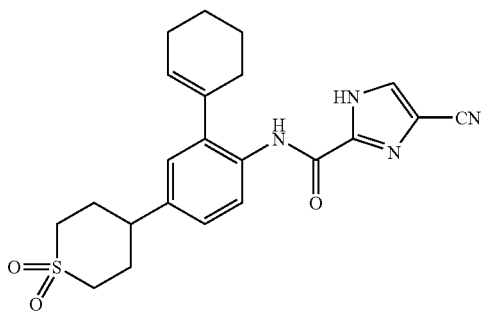

a) Trifluoromethanesulfonic acid 3,6-dihydro-2H-thiopyran-4-yl ester

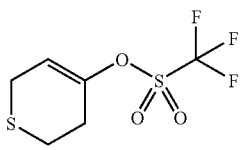

A solution of tetrahydro-thiopyran-4-one (1.00 g, 8.61 mmol) in 10 ml of THF was added to a solution of LDA (2.0 M, 4.52 ml, 9.04 mmol) in 20 ml of THF at −78° C. under Ar. The mixture was warmed to RT and stirred for 0.5 h, then cooled to −78° C. again. A solution of N-phenyltrifluoromethanesulfonimide (3.42 g, 9.47 mmol) in 10 ml of THF was added. The resulting mixture was warmed to RT and stirred for 0.5 h under Ar. Treated with 200 ml of EtOAc, the mixture was washed with H$_2$O (3×50 mL), brine (50 mL) and dried (Na$_2$SO$_4$). Removal of the solvent under reduced pressure followed by flash chromatography of the residue on silica gel (hexane-3% EtOAc/hexane) gave 810 mg (38%) of the title compound as a colorless oil. $^1$H-NMR (CDCl$_3$; 400 MHz): δ 6.01 (m, 1H), 3.30 (m, 2H), 2.86 (dd, 2H, J=5.7, 5.7 Hz), 2.58-2.64 (m, 2H). Mass spectrum (ESI, m/z): Calcd. for C$_6$H$_7$F$_3$O$_3$S$_2$, 249.0 (M+H), found 249.3.

b) 4-(4-Nitro-phenyl)-3,6-dihydro-2H-thiopyran

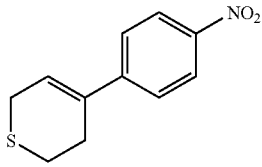

To a mixture of 4-nitrophenylboronic acid (418 mg, 2.50 mmol), trifluoromethanesulfonic acid 3,6-dihydro-2H-thiopyran-4-yl ester (as prepared in the previous step, 931 mg, 3.75 mmol), Pd(PPh$_3$)$_4$ (433 mg, 0.375 mmol) and lithium chloride (LiCl) (212 mg, 5.0 mmol) in 20 mL of 1,4-dioxane was added 2.0 M aq Na$_2$CO$_3$ solution (3.13 mL, 6.25 mmol). The resulting mixture was stirred at 80° C. for 2 h and then cooled to RT. Treated with 200 mL of EtOAc, the mixture was washed with H$_2$O (2×30 mL), brine (30 mL) and dried (Na$_2$SO$_4$). Removal of the solvent under reduced pressure followed by flash chromatography of the residue on silica gel (1-3% EtOAc/hexane) gave 470 mg (85%) of the title compound as a light brown oil. $^1$H-NMR (CDCl$_3$; 400 MHz): δ 8.19 (d, 2H, J=9.1 Hz), 7.48 (d, 2H, J=9.1 Hz), 6.36 (m, 1H), 3.39 (m, 2H), 2.91 (t, 2H, J=5.7 Hz), 2.72 (m, 2H). Mass spectrum (ESI, m/z): Calcd. for C$_{11}$H$_{11}$NO$_2$S, 222.1 (M+H), found 222.3.

c) 4-(4-Nitro-phenyl)-3,6-dihydro-2H-thiopyran 1,1-dioxide

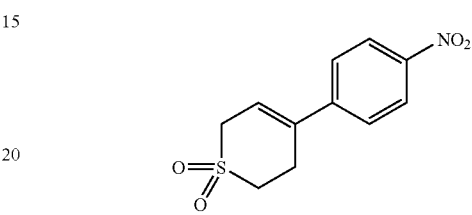

A solution of 3-chloroperoxybenzoic acid (1.04 g, 4.62 mmol, 77%) in 15 mL of dichloromethane (DCM) was added slowly to a solution of 4-(4-nitro-phenyl)-3,6-dihydro-2H-thiopyran (as prepared in the previous step, 465 mg, 2.10 mmol) in 15 mL of DCM at −78° C. under Ar. The mixture was stirred at −78° C. for 0.5 h, and then warmed to RT. Treated with 100 mL of EtOAc, the mixture was washed with 10% Na$_2$SO$_3$ (2×15 mL), satd aq NaHCO$_3$ solution (20 mL), H$_2$O (20 mL), brine (20 mL) and dried (Na$_2$SO$_4$). Removal of the solvent under reduced pressure followed by flash chromatography of the residue on silica gel (2-5% EtOAc/DCM) gave 518 mg (97%) of the title compound as a white solid. $^1$H-NMR (CDCl$_3$; 400 MHz): δ 8.23 (d, 2H, J=9.0 Hz), 7.52 (d, 2H, J=9.0 Hz), 6.04 (m, 1H), 3.86 (m, 2H), 3.26-3.31 (m, 2H), 3.18-3.23 (m, 2H).

d) 4-(1,1-Dioxo-hexahydro-1-thiopyran-4-yl)-phenylamine

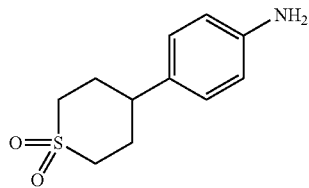

A mixture of 4-(4-nitro-phenyl)-3,6-dihydro-2H-thiopyran 1,1-dioxide (as prepared in the previous step, 502 mg, 1.98 mmol) and 10% Pd/C (250 mg, 50 wt %) in 15 mL of MeOH was stirred at RT under H$_2$ (balloon pressure) for 2 h. The Pd catalyst was removed by filtration on Celite, and the filtrate was concentrated to give 314 mg (70%) of the title compound as a slightly yellow solid. $^1$H-NMR (CDCl$_3$; 400 MHz): δ 7.03 (d, 2H, J=8.3 Hz), 6.67 (d, 2H, J=8.3 Hz), 3.51-3.79 (br s, 2H), 3.11-3.17 (m, 4H), 2.70 (dddd, 1H, J=12.3, 12.3, 2.9, 2.9 Hz), 2.31-2.43 (m, 2H), 2.15-2.23 (m, 2H).

e) 2-Bromo-4-(1,1-dioxo-hexahydro-1λ⁶-thiopyran-4-yl)-phenylamine

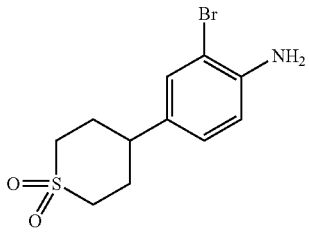

To a suspension of 4-(1,1-dioxo-hexahydro-1λ⁶-thiopyran-4-yl)-phenylamine (as prepared in the previous step, 174 mg, 0.77 mmol) in 20 mL of 3:1 DCM/MeOH at 0° C. was added N-bromosuccinimide (NBS) (137 mg, 0.77 mmol) in 5 mL of DCM under Ar. The mixture was warmed to RT and stirred for 1 h under Ar. Treated with 100 mL of EtOAc, the mixture was washed with $H_2O$ (2×20 mL), brine (20 mL) and dried ($Na_2SO_4$). Removal of the solvent under reduced pressure followed by flash chromatography of the residue on silica gel (2-3% EtOAc/DCM) gave 155 mg (66%) of the title compound as a white solid. ¹H-NMR ($CDCl_3$; 400 MHz): δ 7.28 (d, 1H, J=2.0 Hz), 6.97 (dd, 1H, J=8.3, 2.0 Hz), 6.73 (d, 1H, J=8.3 Hz), 4.07 (br s, 2H), 3.09-3.14 (m, 4H), 2.66 (dddd, 1H, J=12.1, 12.1, 3.3, 3.3 Hz), 2.26-2.39 (m, 2H), 2.12-2.21 (m, 2H). Mass spectrum (ESI, m/z): Calcd. for $C_{11}H_{14}BrNO_2S$, 304.0 (M+H), found 304.1.

f) 2-Cyclohex-1-enyl-4-(1,1-dioxo-hexahydro-1-thiopyran-4-yl)-phenylamine

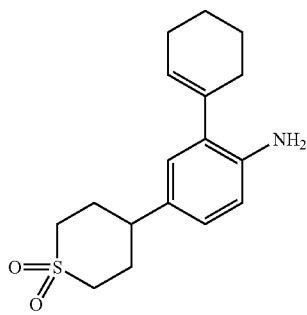

To a mixture of 2-bromo-4-(1,1-dioxo-hexahydro-1λ⁶-thiopyran-4-yl)-phenylamine (as prepared in the previous step, 150 mg, 0.493 mmol), cyclohexen-1-yl boronic acid (70 mg, 0.542 mmol) and $Pd(PPh_3)_4$ (57 mg, 0.0493 mmol) in 5 mL of 1,4-dioxane was added 2.0 M aq $Na_2CO_3$ solution (2.0 mL, 4.0 mmol). The resulting mixture was stirred at 80° C. for 8 h under Ar, and then cooled to RT. Treated with 50 mL of EtOAc, the mixture was washed with $H_2O$ (3×15 mL), brine (20 mL) and dried ($Na_2SO_4$). Removal of the solvent under reduced pressure followed by flash chromatography of the residue on silica gel (2-5% EtOAc/DCM) gave 130 mg (86%) of the title compound as a brown solid. ¹H-NMR ($CDCl_3$; 400 MHz): δ 6.89 (dd, 1H, J=8.4, 2.3 Hz), 6.84 (d, 1H, J=2.3 Hz), 6.65 (d, 1H, J=8.4 Hz), 5.74 (m, 1H), 3.74 (br s, 2H), 3.08-3.17 (m, 4H), 2.66 (dddd, 1H, J=12.1, 12.1, 3.1, 3.1 Hz), 2.29-2.42 (m, 2H), 2.13-2.25 (m, 6H), 1.73-1.81 (m, 2H), 1.65-1.73 2H). Mass spectrum (ESI, m/z): Calcd. for $C_{17}H_{23}NO_2S$, 306.1 (M+H), found 306.1.

g) 4-Cyano-1-(2-trimethylsilanyl-ethoxymethyl)-1H-imidazole-2-carboxylic acid [2-cyclohex-1-enyl-4-(1,1-dioxo-hexahydro-1λ⁶-thiopyran-4-yl)-phenyl]-amide

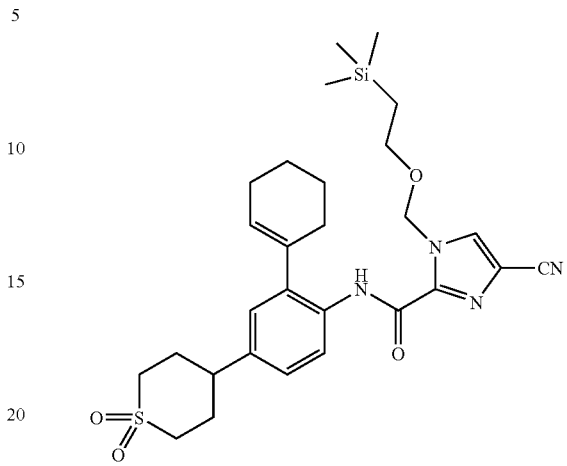

To a mixture of 2-cyclohex-1-enyl-4-(1,1-dioxo-hexahydro-1λ⁶-thiopyran-4-yl)-phenylamine (as prepared in the previous step, 122 mg, 0.50 mmol), potassium 4-cyano-1-(2-trimethylsilanyl-ethoxymethyl)-1H-imidazole-2-carboxylate (as prepared in Example 3, step (d), 134 mg, 0.44 mmol) and bromotri(pyrrolidino)phosphonium hexafluorophosphate (PyBroP) (205 mg, 0.44 mmol) in 5 mL of DMF was added DIEA (209 µL, 1.20 mmol). The resulting mixture was stirred at RT for 18 h under Ar, cooled to RT. Treated with 50 mL of EtOAc, the mixture was washed with $H_2O$ (3×10 mL), brine (10 mL) and dried ($Na_2SO_4$). Removal of the solvent under reduced pressure followed by flash chromatography of the residue on silica gel (1-3% EtOAc/DCM) gave 161 mg (73%) of the title compound as a colorless oil. ¹H-NMR ($CDCl_3$; 400 MHz): δ 9.69 (s, 1H), 8.29 (d, 1H, J=8.4 Hz), 7.78 (s, 1H), 7.14 (dd, 1H, J=8.4, 2.2 Hz), 7.04 (d, 1H, J=2.2 Hz), 5.95 (s, 2H), 5.83 (m, 1H), 3.66 (t, 2H, J=8.2 Hz), 3.11-3.20 (m, 4H), 2.77 (dddd, 1H, J=12.1, 12.1, 3.2, 3.2 Hz), 2.35-2.47 (m, 2H), 2.17-2.33 (m, 6H), 1.74-1.89 (m, 4H), 0.97 (t, 2H, J=8.2 Hz), 0.00 (s, 9H). Mass spectrum (ESI, m/z): Calcd. for $C_{28}H_{38}N_4O_4SSi$, 555.2 (M+H), found 555.3.

h) 4-Cyano-1H-imidazole-2-carboxylic acid [2-cyclohex-1-enyl-4-(1,1-dioxo-hexahydro-1λ⁶-thiopyran-4-yl)-phenyl]-amide

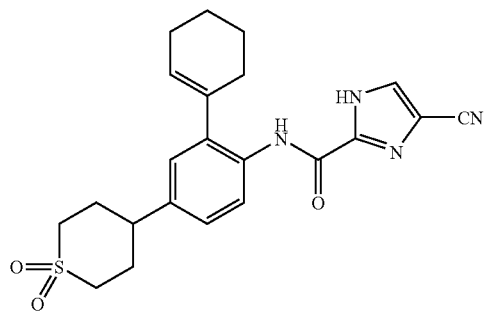

To a solution of 4-cyano-1-(2-trimethylsilanyl-ethoxymethyl)-1H-imidazole-2-carboxylic acid [2-cyclohex-1-enyl-4-(1,1-dioxo-hexahydro-1λ⁶-thiopyran-4-yl)-phenyl]-amide (as prepared in the previous step, 145 mg, 0.261 mmol) in 6 mL of DCM was added 0.20 mL of EtOH followed by 2 mL of TFA. The resulting solution was stirred at RT for 3 h. Removal of the solvent under reduced pressure followed by flash chromatography of the residue on silica gel (20-25% EtOAc/DCM) gave 83 mg (90%) of the title compound as a white solid. $^1$H-NMR (CDCl$_3$; 400 MHz): δ 12.34 (s, 1H), 9.60 (s, 1H), 8.35 (d, 1H, J=8.4 Hz), 7.75 (s, 1H), 7.30 (dd, 1H, J=8.4, 2.2 Hz), 7.08 (d, 1H, J=2.2 Hz), 5.86 (m, 1H), 3.11-3.23 (m, 4H), 2.80 (dddd, 1H, J=12.2, 12.2, 2.8, 2.8 Hz), 2.40-2.57 (m, 2H), 2.17-2.35 (m, 6H), 1.74-1.91 (m, 4H). Mass spectrum (ESI, m/z): Calcd. for $C_{22}H_{24}N_4O_3S$, 425.2 (M+H), found 425.6.

EXAMPLE 36

4-Cyano-1H-imidazole-2-carboxylic acid [2-(1,1-dioxo-1,2,3,6-tetrahydro-1λ$^6$-thiopyran-4-yl)-4-piperidin-4-yl-phenyl]-amide trifluoroacetic acid salt

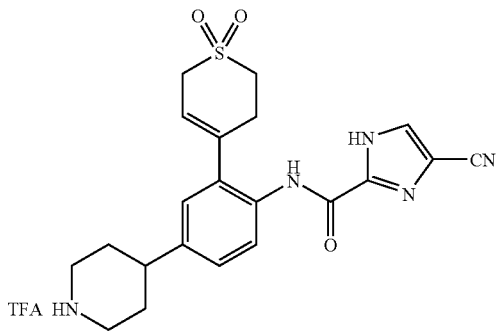

a) 2-(3,6-Dihydro-2H-thiopyran-4-yl)-5,5-dimethyl-[1,3,2]dioxaborinane

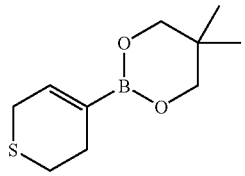

A mixture of trifluoromethanesulfonic acid 3,6-dihydro-2H-thiopyran-4-yl ester (as prepared in Example 35, step (a), 500 mg, 2.01 mmol), bis(neopentyl glycolato)diboron (478 mg, 2.11 mmol), Pd(dppf)Cl$_2$ (147 mg, 0.20 mmol) and KOAc (592 mg, 6.03 mmol) in 8 mL of 1,4-dioxane was stirred at 80° C. for 8 h under Ar, and then cooled to RT. Treated with 50 mL of EtOAc, the mixture was washed with H$_2$O (2×10 mL), brine (10 mL) and dried (Na$_2$SO$_4$). Removal of the solvent under reduced pressure followed by flash chromatography of the residue on silica gel (0-5% EtOAc/DCM) gave 351 mg (82%) of the title compound as a colorless oil. $^1$H-NMR (CDCl$_3$; 400 MHz): δ 6.62 (m, 1H), 3.63 (s, 4H), 3.21 (m, 2H), 2.68 (t, 2H, J=5.8 Hz), 2.37 (m, 2H), 0.96 (s, 6H). Mass spectrum (ESI, m/z): Calcd. for $C_{10}H_{17}BO_2S$, 213.1 (M+H), found 213.1.

b) 4-[4-Amino-3-(3,6-dihydro-2H-thiopyran-4-yl)-phenyl]-piperidine-1-carboxylic acid tert-butyl ester

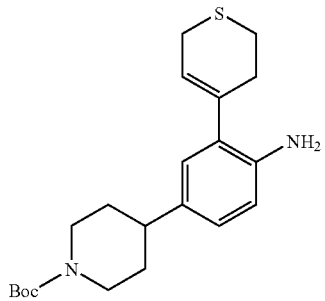

To a mixture of 4-(4-amino-3-bromo-phenyl)-piperidine-1-carboxylic acid tert-butyl ester (as prepared in Example 13, step (c), 200 mg, 0.563 mmol), 2-(3,6-dihydro-2H-thiopyran-4-yl)-5,5-dimethyl-[1,3,2]dioxaborinane (as prepared in the previous step, 131 mg, 0.619 mmol) and Pd(PPh$_3$)$_4$ (65 mg, 0.056 mmol) in 5 mL of 1,4-dioxane was added 2.0 M aq Na$_2$CO$_3$ solution (2.25 mL, 4.5 mmol). The resulting mixture was stirred at 80° C. for 7 h under Ar, and then cooled to RT. Treated with 50 mL of EtOAc, the mixture was washed with H$_2$O (3×15 mL), brine (20 mL) and dried (Na$_2$SO$_4$). Removal of the solvent under reduced pressure followed by flash chromatography of the residue on silica gel (15-30% EtOAc/hexane) gave 141 mg (67%) of the title compound as a colorless oil. $^1$H-NMR (CDCl$_3$; 400 MHz): δ 6.91 (dd, 1H, J=8.2, 2.2 Hz), 6.81 (d, 1H, J=2.2 Hz), 6.65 (d, 1H, J=8.2 Hz), 5.91 (m, 1H), 4.22 (br s, 2H), 3.66 (br s, 2H), 3.29-3.31 (m, 2H), 2.87 (dd, 2H, J=5.7, 5.7 Hz), 2.77 (m, 2H), 2.47-2.56 (m, 3H), 1.78 (d, 2H, J=12.6 Hz), 1.50-1.63 (m, 2H), 1.48 (s, 9H). Mass spectrum (ESI, m/z): Calcd. for $C_{21}H_{30}N_2O_2S$, 375.2 (M+H), found 375.2.

c) 4-[4-{[4-Cyano-1-(2-trimethylsilanyl-ethoxymethyl)-1H-imidazole-2-carbonyl]-amino}-3-(3,6-dihydro-2H-thiopyran-4-yl)-phenyl]-piperidine-1-carboxylic acid tert-butyl ester

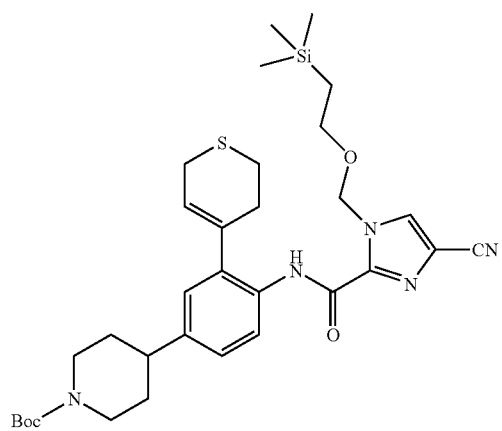

To a mixture of 4-[4-amino-3-(3,6-dihydro-2H-thiopyran-4-yl)-phenyl]-piperidine-1-carboxylic acid tert-butyl ester (as prepared in the previous step, 45 mg, 0.12 mmol), potassium 4-cyano-1-(2-trimethylsilanyl-ethoxymethyl)-1H-imidazole-2-carboxylate (as prepared in Example 3, step (d), 44 mg, 0.144 mmol) and PyBroP (67 mg, 0.144 mmol) in 2 mL of DMF was added DIEA (42 μL, 0.24 mmol). The resulting mixture was stirred at RT for 4 h under Ar. Treated with 30 mL of EtOAc, the mixture was washed with H$_2$O (3×10 mL), brine (10 mL) and dried (Na$_2$SO$_4$). Removal of the solvent under reduced pressure followed by flash chromatography of the residue on silica gel (1-2% EtOAc/DCM) gave 64 mg (85%) of the title compound as a light yellow oil. $^1$H-NMR (CDCl$_3$; 400 MHz): δ 9.51 (s, 1H), 8.21 (d, 1H, J=8.5 Hz), 7.78 (s, 1H), 7.16 (dd, 1H, J=8.5, 2.1 Hz), 7.02 (d, 1H, J=2.1 Hz), 6.00 (m, 1H), 5.92 (s, 2H), 4.25 (br s, 2H), 3.66 (t, 2H, J=8.2), 3.42 (m, 2H), 2.93 (dd, 2H, J=5.7, 5.7 Hz), 2.79 (m, 2H), 2.63 (dddd, 1H, J=12.3, 12.3, 3.3, 3.3 Hz), 2.49-2.56 (m, 2H), 1.82(d, 2H, J=12.8 Hz), 1.56-1.66 (m, 2H), 1.49 (s, 9H), 0.97 (t, 2H, J=8.2 Hz), 0.00 (s, 9H).

d) 4-[4-{[4-Cyano-1-(2-trimethylsilanyl-ethoxymethyl)-1H-imidazole-2-carbonyl]-amino}-3-(1,1-dioxo-1,2,3,6-tetrahydro-1λ$^6$-thiopyran-4-yl)-phenyl]-piperidine-1-carboxylic acid tert-butyl ester

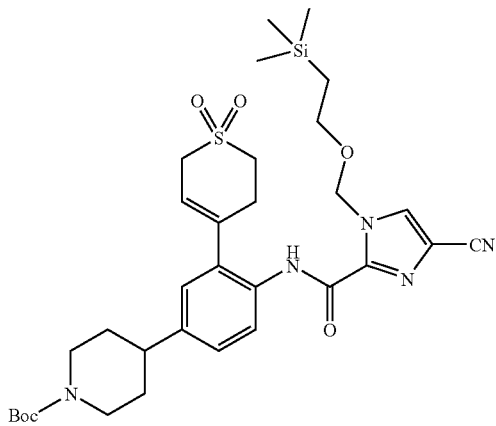

A solution of 3-chloroperoxybenzoic acid (91 mg, 0.404 mmol, 77%) in 1 mL of DCM was added slowly to 4-[4-{[4-cyano-1-(2-trimethylsilanyl-ethoxymethyl)-1H-imidazole-2-carbonyl]-amino}-3-(3,6-dihydro-2H-thiopyran-4-yl)-phenyl]-piperidine-1-carboxylic acid tert-butyl ester (as prepared in the previous step, 120 mg, 0.192 mmol) in 3 mL of DCM at –78° C. under Ar. The mixture was stirred at –78° C. for 15 min, and then warmed to RT. Treated with 40 mL of EtOAc, the mixture was washed with 15% Na$_2$SO$_3$ (5 mL), satd aq NaHCO$_3$ solution (2×10 mL), H$_2$O (10 mL), brine (10 mL) and dried (Na$_2$SO$_4$). Removal of the solvent under reduced pressure followed by flash chromatography of the residue on silica gel (2-10% EtOAc/DCM) gave 85 mg (67%) of the title compound as a colorless oil. $^1$H-NMR (CDCl$_3$; 400 MHz): δ 9.23 (s, 1H), 8.03 (d, 1H, J=8.3 Hz), 7.80 (s, 1H), 7.21 (dd, 1H, J=8.3, 2.0 Hz), 7.06 (d, 1H, J=2.0 Hz), 5.93 (s, 2H), 5.75 (t, 1H, J=4.1Hz), 4.25 (br s, 2H), 3.86 (br s, 2H), 3.66 (t, 2H, J=8.2 Hz), 3.29 (t, 2H, J=6.3 Hz), 3.03 (t, 2H, J=5.4 Hz), 2.74-2.86 (m, 2H), 2.64 (dddd, 1H, J=12.3, 12.3, 3.3, 3.3 Hz), 1.82 (d, 2H, J=12.3 Hz), 1.55-1.65 (m, 2H), 1.49 (s, 9H), 0.98 (t, 2H, J=8.2 Hz), 0.01 (s, 9H). Mass spectrum (ESI, m/z): Calcd. for C$_{32}$H$_{45}$N$_5$O$_6$SSi, 656.3 (M+H), found 656.7.

e) 4-Cyano-1H-imidazole-2-carboxylic acid [2-(1,1-dioxo-1,2,3,6-tetrahydro-1λ$^6$-thiopyran-4-yl)-4-piperidin-4-yl-phenyl]-amide, trifluoroacetic acid salt

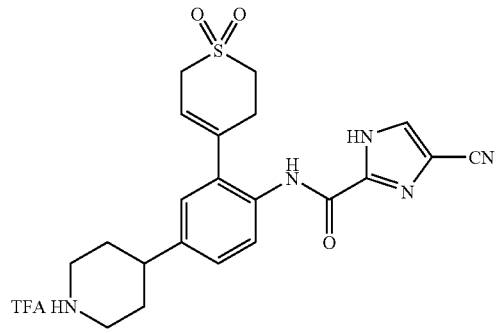

To a solution of 4-[4-{[4-cyano-1-(2-trimethylsilanyl-ethoxymethyl)-1H-imidazole-2-carbonyl]-amino}-3-(1,1-dioxo-1,2,3,6-tetrahydro-1λ$^6$-thiopyran-4-yl)-phenyl]-piperidine-1-carboxylic acid tert-butyl ester (as prepared in the previous step, 81 mg, 0.123 mmol) in 6 mL of DCM was added 0.20 mL of EtOH followed by 2 mL of TFA. The resulting solution was stirred at RT for 3 h. Removal of the solvent under reduced pressure gave 64 mg (96%) of the title compound as a white solid. $^1$H-NMR (CD$_3$OD; 400 MHz): δ 8.02 (s, 1H), 7.78 (d, 1H, J=8.3 Hz), 7.29 (dd, 1H, J=8.3, 2.0 Hz), 7.21 (d, 1H, J=2.0 Hz), 5.71 (t, 1H, J=4.2 Hz), 3.83 (br s, 2H), 3.51 (d, 2H, J=12.4 Hz), 3.33 (t, 2H, J=6.0 Hz), 3.15 (td, 2H, J=13.1, 2.6 Hz), 3.01 (m, 2H), 2.94 (dddd, 1H, J=12.2, 12.2, 3.5, 3.5 Hz), 2.08 (d, 2H, J=12.9 Hz), 1.91 (m, 2H, J=13.3, 13.3, 13.3, 3.8 Hz). Mass spectrum (ESI, m/z): Calcd. for C$_{21}$H$_{23}$N$_5$O$_3$S, 426.2 (M+H), found 426.2.

EXAMPLE 37

4-Cyano-1H-imidazole-2-carboxylic acid [4-(1-acetyl-piperidin-4-yl)-2-(1,1-dioxo-1,2,3,6-tetrahydro-1λ$^6$-thiopyran-4-yl)-phenyl]-amide

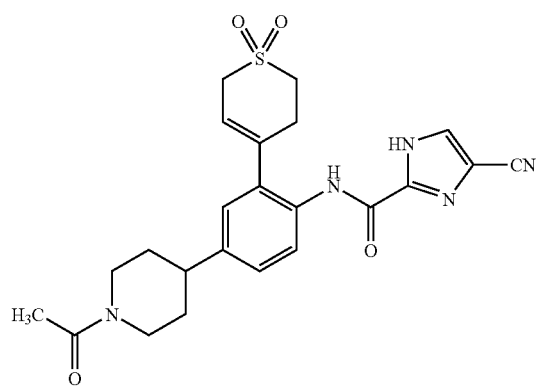

To a suspension of 4-cyano-1H-imidazole-2-carboxylic acid [2-(1,1-dioxo-1,2,3,6-tetrahydro-1λ$^6$-thiopyran-4-yl)-4-piperidin-4-yl-phenyl]-amide trifluoroacetic acid salt (as prepared in Example 36, step (e), 62 mg, 0.115 mmol) in 4 mL of 1:1 DCM/DMF at RT was added DIEA (60 μL, 0.345 mmol). The mixture was stirred for 5 min, then acetic anhydride (11 μL, 0.121 mmol) was added slowly to the mixture, and the resulting mixture was stirred at RT for 0.5 h. Treated with 40 mL of EtOAc, the mixture was washed with H₂O (2×20 mL). The aqueous layers were extracted with EtOAc (4×10 mL). The combined organic layers were concentrated in vacuo. The residue was purified by flash chromatography on silica gel (1-4% MeOH/DCM) yielding 50.9 mg (95%) of the title compound as a white solid. $^1$H-NMR (CDCl$_3$; 400 MHz): δ 13.0 (s, 1H), 9.10 (s, 1H), 8.13 (d, 1H, J=8.4 Hz), 7.77 (d, 1H, J=2.3 Hz), 7.26 (dd, 1H, J=8.4, 2.0 Hz), 7.08 (d, 1H, J=2.0 Hz), 5.77 (t, 1H, J=4.3 Hz), 4.84 (dt, 1H, J=13.3, 2.1Hz), 4.00 (dt, 1H, J=13.3, 2.1 Hz), 3.89 (br s, 2H), 3.31 (t, 2H, J=6.2 Hz), 3.23 (td, 1H, J=13.2, 2.5 Hz), 3.02 (m, 2H), 2.77 (dddd, 1H, J=11.9, 11.9, 3.4, 3.4 Hz), 2.68 (ddd, 1H, J=12.6, 12.6, 2.9 Hz), 2.18 (s, 3H), 1.70-1.97 (m, 4H). Mass spectrum (ESI, m/z): Calcd. for C$_{23}$H$_{25}$N$_5$O$_4$S, 468.2 (M+H), found 468.1.

EXAMPLE 38a

4-Cyano-1H-imidazole-2-carboxylic acid {2-cyclohex-1-enyl-4-[1-(2-dimethylamino-acetyl)-piperidin-4-yl]-phenyl}-amide

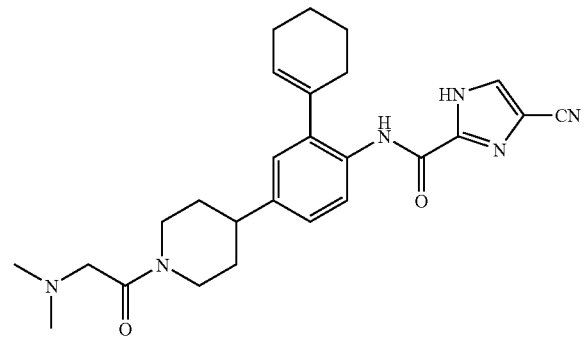

A mixture of 4-cyano-1H-imidazole-2-carboxylic acid (2-cyclohex-1-enyl-4-piperidin-4-yl-phenyl)-amide trifluoroacetic acid salt (as prepared in Example 14, step (b), 655 mg, 1.30 mmol) in DCM (15 mL) was cooled to 0° C. and DIEA (0.92 mL, 5.2 mmol) was added. Dimethylaminoacetyl chloride hydrochloride (211 mg, 1.3 mol) was then added portion wise over 10 min. The reaction mixture was stirred at 0° C. for 30 min and allowed to warm to RT and stirred for 2 h. Solvent was removed in vacuo and the resulting residue was partitioned between brine and DCM. The organic layer was separated, dried (Na$_2$SO$_4$) and concentrated. The residue obtained was purified on silica (5% MeOH: DCM) to obtain 432 mg (70%) of the title compound as a white solid. $^1$H-NMR (CDCl$_3$; 400 MHz): δ 9.49 (s, 1H), 8.24 (d, 1H, J=2.3 Hz), 7.70 (s, 1H), 7.12 (dd, 1H, J=8.4, 2.1 Hz), 7.01 (s, 1H), 5.82 (m, 1H), 4.75 (d, 1H, J=13.4Hz), 4.13 (d, 1H, J=13.4 Hz), 3.57 (d, 1H, J=14.2 Hz), 3.18 (d, 1H, J=14.2 Hz), 3.12 (td, 1H, J=13.3, 2.4 Hz), 2.73 (dddd, 1H, J=11.9, 11.9, 3.8, 3.8 Hz), 2.65 (ddd, 1H, J=13.3, 13.3, 2.4 Hz), 2.40 (s, 6H), 2.18-2.32 (m, 4H), 1.60-1.98 (m, 8H). Mass spectrum (ESI, m/z): Calcd. for C$_{26}$H$_{32}$N$_6$O$_2$, 461.3 (M+H), found 461.2.

EXAMPLE 38b

4-Cyano-1H-imidazole-2-carboxylic acid {2-cyclohex-1-enyl-4-[1-(2-methylamino-acetyl)-piperidin-4-yl]-phenyl}-amide

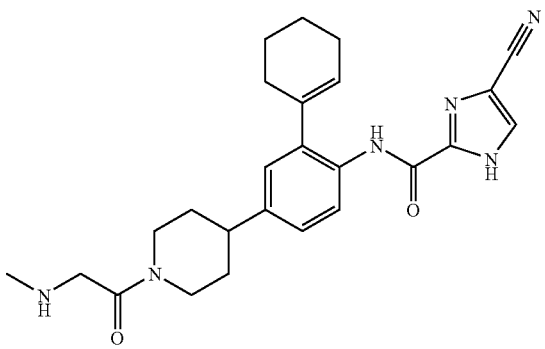

HPLC purification of Example 38a also afforded a small amount of 4-cyano-1H-imidazole-2-carboxylic acid {2-cyclohex-1-enyl-4-[1-(2-methylamino-acetyl)-piperidin-4-yl]-phenyl}-amide. $^1$H-NMR (CD$_3$OD; 400 MHz): δ 8.02 (d, 1H, J=8.4 Hz), 7.92 (s, 1H), 7.07 (dd, 1H, J=8.4 Hz, J=2.4 Hz), 6.98 (d, 1H, J=2.4 Hz), 5.73-5.68 (m, 1H), 4.60-4.51 (m, 1H), 3.76-3.68 (m, 1H), 3.20-3.11 (m, 1H), 2.81-2.70 (m, 2H), 2.67 (s, 3H), 2.22-2.13 (m, 4H), 1.88-1.66 (m, 6H), 1.66-1.46 (m, 2H). Mass spectrum (ESI, m/z): Calcd. for C$_{25}$H$_{30}$N$_6$O$_2$, 447.2 (M+H), found 447.3.

EXAMPLE 39

4-{4[(4Cyano-1H-imidazole-2-carbonyl)-amino]-3-cyclohex-1-enyl-phenyl}-piperidine-1-carboxylic acid (2-hydroxy-ethyl)-amide

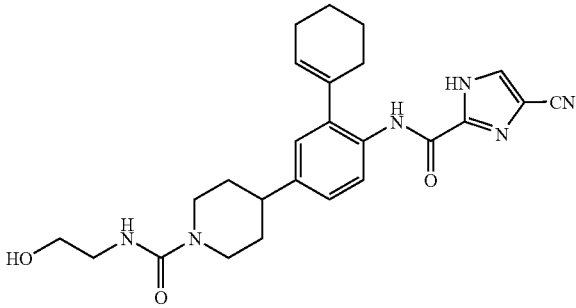

a) 4-Cyano-1-(2-trimethylsilanyl-ethoxymethyl)-1H-imidazole-2-carboxylic acid (2-cyclohex-1-enyl-4-piperidin-4-yl-phenyl)-amide, trifluoroacetic acid salt

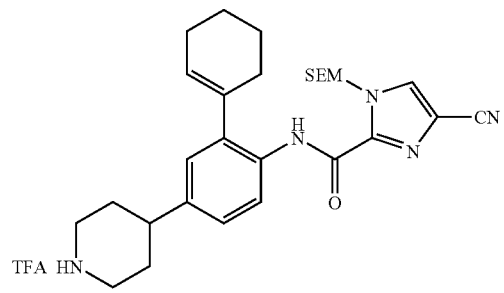

To a solution of 4-(4-{[4-cyano-1-(2-trimethylsilanyl-ethoxymethyl)-1H-imidazole-2-carbonyl]-amino }-3-cyclohex-1-enyl-phenyl)-piperidine-1-carboxylic acid tert-butyl ester (as prepared in Example 14, step (a), 81 mg, 0.123 mmol) in 18 mL of DCM was added 1 mL of EtOH followed by 5 mL of TFA at 0° C. The resulting solution was stirred at RT for 0.5 h, treated with 20 mL of EtOH followed by 20 mL of n-PrOH and 5 mL of H$_2$O, the mixture was then concentrated under reduced pressure to give a slightly yellow solid. Flash chromatography of the compound on silica gel (2-4% MeOH/DCM) gave 0.87 g (85%) of the title compound as a white solid. $^1$H-NMR (CDCl$_3$; 400 MHz): δ 9.70 (s, 1H), 9.66 (br s, 1H), 9.15 (br s, 1H), 8.29 (d, 1H, J=8.3 Hz), 7.78 (s, 1H), 7.13 (dd, 1H, J=8.3, 2.2 Hz), 7.03 (d, 1H, J=2.2 Hz), 5.95 (s, 2H), 5.83 (m, 1H), 3.66 (t, 2H, J=8.4 Hz), 3.55 (d, 2H, J=12.3 Hz), 2.95-3.11 (m, 2H), 2.76 (m, 1H), 2.18-2.33 (m, 4H), 1.99-2.15 (m, 4H), 1.82 (m, 4H), 0.97 (t, 2H, J=8.3 Hz), 0.00 (s, 9H). Mass spectrum (ESI, m/z): Calcd. for C$_{28}$H$_{39}$N$_5$O$_2$Si, 506.3 (M+H), found 506.1.

b) 4-(4-{[4-Cyano-1-(2-trimethylsilanyl-ethoxymethyl)-1H-imidazole-2-carbonyl]-amino}-3-cyclohex-1-enyl-phenyl)-piperidine-1-carboxylic acid (2-hydroxy-ethyl)-amide

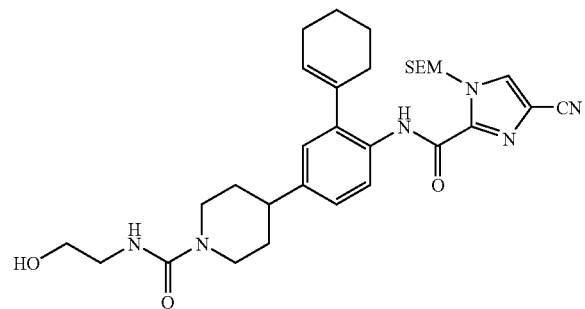

A solution of 4-cyano-1-(2-trimethylsilanyl-ethoxymethyl)-1H-imidazole-2-carboxylic acid (2-cyclohex-1-enyl-4-piperidin-4-yl-phenyl)-amide trifluoroacetic acid salt (as prepared in the previous step, 116 mg, 0.192 mmol) and DIEA (134 µL, 0.770 mmol) in 4 mL of DCM was added slowly to solution of triphosgene (23 mg, 0.0768 mmol) in 4 mL of DCM at −78° C. under Ar. The mixture was stirred at −78° C. for 15 min, warmed to RT and stirred for 15 min and cooled to −78° C. again. A suspension of 2-amino-ethanol (350 µL, 5.77 mmol) in 4 mL of THF was added and the resulting mixture was warmed to RT and stirred for 20 h under Ar. Treated with 100 mL of EtOAc, the mixture was washed with H$_2$O (3×20 mL), brine (20 mL) and dried (Na$_2$SO$_4$). Removal of the solvent in vacuo followed by flash chromatography of the residue on silica gel (10% EtOAc/DCM then 5% MeOH/DCM) gave 95 mg (83%) of the title compound as a colorless oil. $^1$H-NMR (CDCl$_3$; 400 MHz): δ 9.68 (s, 1H), 8.25 (d, 1H, J=8.4 Hz), 7.77 (s, 1H), 7.12 (dd, 1H, J=8.4, 2.2 Hz), 7.01 (d, 1H, J=2.2 Hz), 5.94 (s, 2H), 5.83 (m, 1H), 4.96 (t, 1H, J=5.6 Hz), 4.11 (d, 2H, J=13.3 Hz), 3.75 (ddd, 2H, J=4.4 Hz), 3.66 (t, 2H, J=8.3 Hz), 3.44 (ddd, 2H, J=5.0 Hz), 3.36 (t, 1H, J=4.6 Hz), 2.91 (ddd, 2H, J=13.0, 2.2 Hz), 2.66 (dddd, 1H, J=12.2, 12.2, 3.3, 3.3 Hz), 2.18-2.33 (m, 4H), 1.75-1.91 (m, 6H), 1.67 (dddd, 2H, J=12.9, 12.9, 12.9, 4.0 Hz), 0.97 (t, 2H, J=8.3 Hz), 0.00 (s, 9H). Mass spectrum (ESI, m/z): Calcd. for C$_{31}$H$_{44}$N$_6$O$_4$Si, 593.3 (M+H), found 593.1.

c) 4-{4-[(4-Cyano-1H-imidazole-2-carbonyl)-amino]-3-cyclohex-1-enyl-phenyl}-piperidine-1-carboxylic acid (2-hydroxy-ethyl)-amide

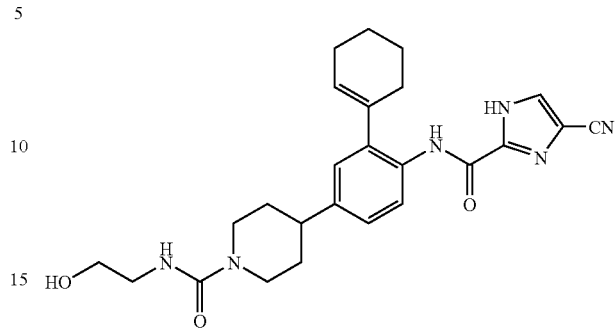

To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid (2-hydroxy-ethyl)-amide (as prepared in the previous step, 95 mg, 0.16 mmol) in 3 mL of DCM was added 0.10 mL of EtOH followed by 1.0 mL of TFA. The resulting solution was stirred at RT for 6 h. Removal of the solvent under reduced pressure followed by flash chromatography of the residue on silica gel (2-8% MeOH/DCM) gave 68 mg (92%) of the title compound as a white solid. $^1$H-NMR (CD$_3$OD; 400 MHz): δ 8.09 (d, 1H, J=8.4 Hz), 8.00 (s, 1H), 7.15 (dd, 1H, J=8.4, 2.2 Hz), 5.79 (m, 1H), 4.15 (dd, 2H, J=13.3, 1.1 Hz), 3.61 (t, 2H, J=5.9 Hz), 3.27-3.32 (m, 2H), 2.90 (ddd, 2H, J=13.0, 13.0, 2.5 Hz), 2.73 (dddd, 1H, J=12.1, 12.1, 2.6, 2.6 Hz), 2.26 (m, 4H), 1.73-1.88 (m, 6H), 1.62 (dddd, 2H, J=12.6, 12.6, 12.6, 4.0 Hz). Mass spectrum (ESI, m/z): Calcd. for C$_{25}$H$_{30}$N$_6$O$_3$, 463.2 (M+H), found 463.2.

EXAMPLE 40

4-Cyano-1H-imidazole-2-carboxylic acid {2-cyclohex-1-enyl-4-[1-(2-methanesulfonyl-ethyl)-piperidin-4-yl]--phenyl }-amide

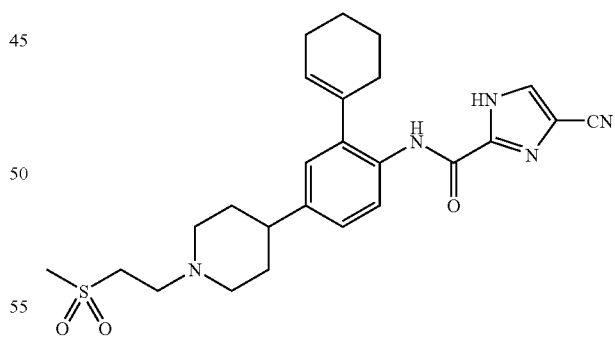

a) Methanesulfonic acid 2-methanesulfonyl-ethyl ester

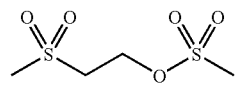

To a solution of methanesulfonyl chloride (484 mg, 4.23 mmol) in 15 mL of DCM at 0° C. was added 2-methanesulfonyl-ethanol (500 mg, 4.03 mmol) in 10 mL of DCM followed by DIEA (1.05 mL, 6.05 mmol) under Ar. The mixture was warmed to RT and stirred for 20 h under Ar. The mixture was treated with 100 mL of EtOAc and washed with H$_2$O (3×20 mL), brine (20 mL) and dried (Na$_2$SO$_4$). Removal of the solvent in vacuo gave 534 mg (66%) of the title compound as a brown oil. $^1$H-NMR (CDCl$_3$; 400 MHz): δ 4.67 (d, 2H, J=5.5 Hz), 3.46 (d, 2H, J=5.5 Hz), 3.11 (s, 3H), 3.04 (s, 3H).

b) 4-Cyano-1H-imidazole-2-carboxylic acid {2-cyclohex-1-enyl-4-[1-(2-methanesulfonyl-ethyl)-piperidin-4-yl]-phenyl}-amide

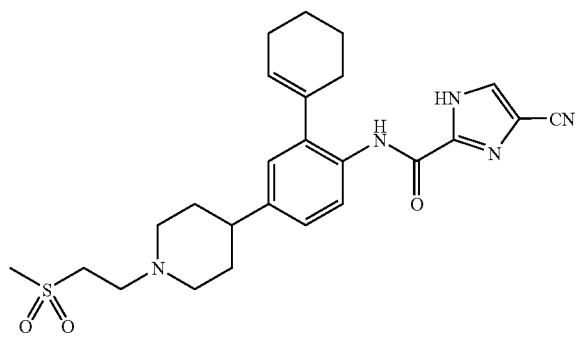

To a solution of 4-cyano-1H-imidazole-2-carboxylic acid (2-cyclohex-1-enyl-4-piperidin-4-yl-phenyl)-amide trifluoroacetic acid salt (as prepared in Example 14, step (b), 85 mg, 0.174 mmol) and DIEA (91 μL, 0.521 mmol) in 3 mL of DCM at RT was added 2-methanesulfonic acid 2-methanesulfonyl-ethyl ester (as prepared in the previous step, 42 mg, 0.208 mmol). The resulting mixture was stirred at RT for 3 h. Treated with 50 mL of EtOAc, the mixture was washed with H$_2$O (2×20 mL), brine (10 mL) and dried (Na$_2$SO$_4$). Removal of the solvent in vacuo followed by flash chromatography of the residue on silica gel (1-3% MeOH/DCM) gave 54 mg (65%) of the title compound as a white solid. $^1$H-NMR (CDCl$_3$; 400 MHz): δ 9.54 (s, 1H), 8.25 (d, 1H, J=8.4 Hz), 7.72 (s, 1H), 7.15 (dd, 1H, J=8.4, 2.0 Hz), 7.04 (d, 1H, J=2.0 Hz), 5.85 (m, 1H), 3.21 (t, 1H, J=6.5 Hz), 3.09 (s, 3H), 3.02-3.11 (m, 2H), 2.92 (t, 2H, J=6.5 Hz), 2.52 (dddd, 1H, J=12.1, 12.1, 3.3, 3.3 Hz), 2.18-2.34 (m, 4H), 2.18 (t, 2H, J=10.8 Hz), 1.64-1.94 (m, 8H). Mass spectrum (ESI, m/z): Calcd. for C$_{25}$H$_{31}$N$_5$O$_3$S, 482.2 (M+H), found 482.2.

The following compounds have been prepared according to the examples as indicated:

| Example | Structure | Mass Spectrum [M + H]$^+$ Calcd. | Found | Formula | Proc. Of Ex |
|---|---|---|---|---|---|
| 41 | 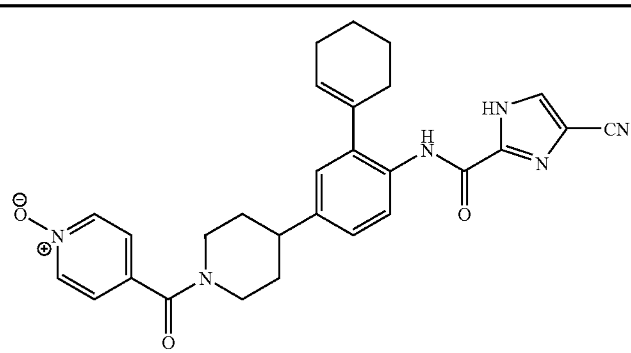 | 497.2 | 497.2 | C$_{28}$H$_{28}$N$_6$O$_3$ | 29 |
| 42 | 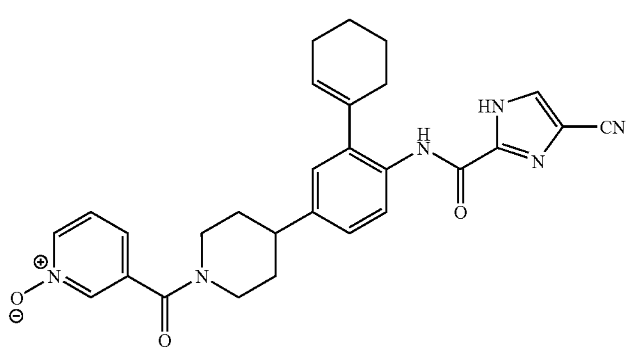 | 497.2 | 497.3 | C$_{28}$H$_{28}$N$_6$O$_3$ | 29 |

EXAMPLE 43

4-Cyano-1H-imidazole-2-carboxylic acid {2-cyclohex-1-enyl-4-[1-(pyridine-3-carbonyl)-piperidin-4-yl]-phenyl}-amide

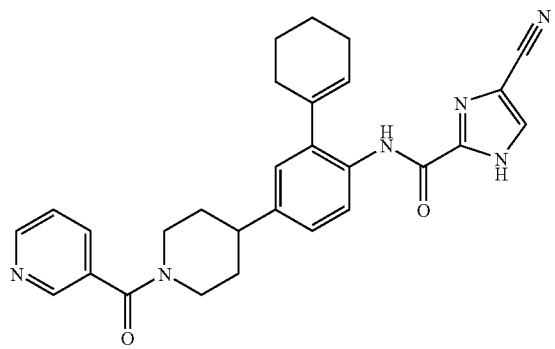

A solution of 4-cyano-1H-imidazole-2-carboxylic acid (2-cyclohex-1-enyl-4-piperidin-4-yl-phenyl)-amide trifluoroacetic acid salt (as prepared in Example 14, step (b), 75.0 mg, 0.15 mmol) in $CH_2Cl_2$ (10 mL) was treated with $Et_3N$ (64.1 µL, 0.46 mmol) and cooled to 0° C. The mixture was treated with nicotinoyl chloride hydrochloride (0.030 g, 0.17 mmol) and stirred at 0° C. for 15 min then at room temperature for 17 h. The reaction mixture was adsorbed directly onto silica gel. Silica gel chromatography (10% MeOH in EtOAc) afforded the title compound (61.0 mg, 83%) as a white solid. $^1$H-NMR (CDCl$_3$; 400 MHz): δ 9.51 (br s, 1H), 8.77 (s, 1H), 8.70-8.66 (m, 1H), 8.32 (d, 1H, J=8.4 Hz), 7.86-7.81 (m, 1H), 7.70 (s, 1H), 7.42-7.37 (m, 1H), 7.17 (d, 1H, J=8.4 Hz), 7.06-7.04 (m, 1H), 5.87-5.82 (m, 1H), 4.98-4.87 (m, 1H), 3.94-3.84 (m, 1H), 3.29-3.18 (m, 1H), 2.98-2.86 (m, 1H), 2.86-2.76 (m, 1H), 2.34-2.20 (m, 4H), 1.94-1.72 (m, 9H). LC-MS (ESI, m/z): Calcd. for $C_{28}H_{28}N_6O_2$, 481.2 (M+H), found 481.3.

EXAMPLE 44

4-Cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt

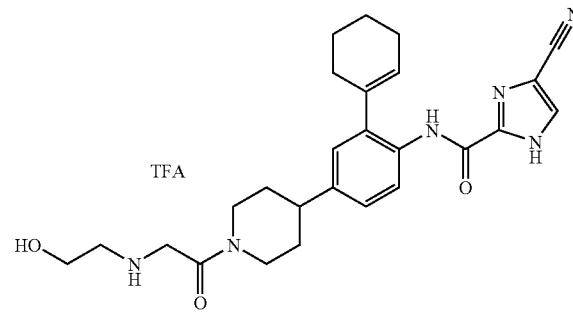

a) [2-(4-{4-[(4-Cyano-1H-imidazole-2-carbonyl)-amino]-3-cyclohex-1-enyl-phenyl}-piperidin-1-yl)-2-oxo-ethyl]-carbamic acid tert-butyl ester

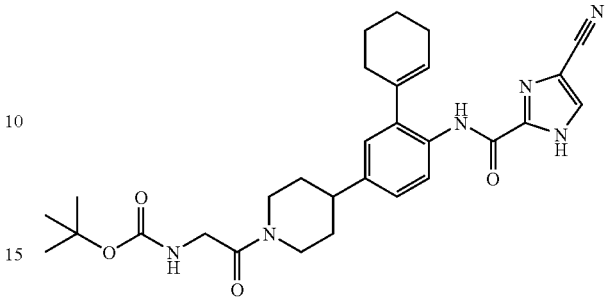

A solution of N-BOC-glycine (0.29 g, 1.63 mmol) in $CH_2Cl_2$ (10 mL) was treated with DIEA (0.85 mL, 4.90 mmol), HOBt (0.26 g, 1.96 mmol), and EDCI (0.38 g, 1.96 mmol). The mixture was stirred at room temperature for 10 min and added to a suspension of 4-cyano-1H-imidazole-2-carboxylic acid (2-cyclohex-1-enyl-4-piperidin-4-yl-phenyl)-amide trifluoroacetic acid salt (as prepared in Example 14, step (b), 0.80 g, 1.63 mmol) in $CH_2Cl_2$ (20 mL). The solution was stirred at room temperature for 17 h. Solvents were evaporated in vacuo. Silica gel chromatography (50% EtOAc in hexanes) afforded the title compound (0.41 g, 47%) as a white solid. $^1$H-NMR (CDCl$_3$; 400 MHz): δ 9.53 (s, 1H), 8.26 (d, 1H, J=8.4 Hz), 7.80-7.78 (m, 1H), 7.71 (s, 1H), 7.45-7.43 (m, 1H), 7.06 (d, 1H, J=8.4 Hz), 7.00 (s, 1H), 5.83 (br s, 1H), 5.76 (br s, 1H), 4.78-4.68 (m, 1H), 3.96-3.85 (m, 2H), 3.17-3.03 (m, 1H), 2.78-2.63 (m, 2H), 2.29 (br s, 2H), 2.22 (br s, 2H), 1.95-1.87 (m, 2H), 1.86-1.72 (m, 4H), 1.70-1.55 (m, 2H), 1.44 (s, 9H). LC-MS (ESI, m/z): Calcd. for $C_{29}H_{36}N_6O_4$ 533.3 (M+H), found 532.9.

b) 4-Cyano-1H-imidazole-2-carboxylic acid {4-[1-(2-amino-acetyl)-piperidin-4-yl]-2-cyclohex-1-enyl-phenyl]-amide trifluoroacetic acid salt

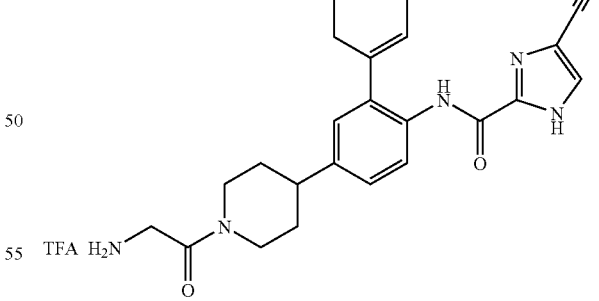

A solution of [2-(4-{4-[(4-cyano-1H-imidazole-2-carbonyl)-amino]-3-cyclohex-1-enyl-phenyl}-piperidin-1-yl)-2-oxo-ethyl]-carbamic acid tert-butyl ester (as prepared in the previous step, 0.41 g, 0.77 mmol) in $CH_2Cl_2$ (20 mL) was treated with EtOH (0.2 mL) and TFA (6 mL). The mixture stirred at room temperature for 45 min, and the solvents were evaporated in vacuo. The crude material was used directly in the next step. LC-MS (ESI, m/z): Calcd. for $C_{24}H_{28}N_6O_2$ 433.2 (M+H), found 433.2.

c) 4-Cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt

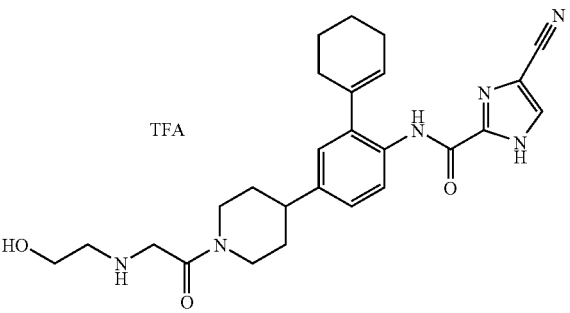

A suspension of 4-cyano-1H-imidazole-2-carboxylic acid {4-[1-(2-amino-acetyl)-piperidin-4-yl]-2-cyclohex-1-enyl-phenyl}-amide trifluoroacetic acid salt (as prepared in the previous step, 0.42 g, 0.77 mmol) in CH₂Cl₂ (20 mL) was treated with Na(OAc)₃BH (0.33 g, 1.54 mmol) and solid glyoxal (44.6 mg, 0.77 mmol). The mixture stirred at room temperature for 1 h, and the solvent was evaporated in vacuo. The residue was taken up in MeOH and the solids filtered off, and the filtrate was concentrated in vacuo. Reverse phase HPLC (C-18 column) (20% to 60% acetonitrile in water with 0.1% TFA over 30 min) afforded the title compound (83 mg, 19% over two steps) as a white solid. $^1$H-NMR (CD₃OD; 400 MHz): δ 8.16-8.09 (m, 1H), 8.05-8.01 (m, 1H), 7.22-7.15 (m, 1H), 7.11-7.06 (m, 1H), 5.84-5.79 (m, 1H), 4.72-4.62 (m, 1H), 4.24-3.91 (m, 2H), 3.89-3.80 (m, 2H), 3.28-3.18 (m, 2H), 2.92-2.79 (m, 2H), 2.28 (br s, 4H), 1.98-1.89 (m, 2H), 1.89-1.76 (m, 4H), 1.76-1.57 (m, 2H). LC-MS (ESI, m/z): Calcd. for $C_{26}H_{32}N_6O_3$ 477.2 (M+H), found 477.2.

EXAMPLE 45

4-Cyano-1H-imidazole-2-carboxylic acid (2-cyclo-hex-1-enyl-4-{1-[2-(2-hydroxy-ethyl)-methyl-amino-acetyl]-piperidin-4-yl}-phenyl)-amide trifluoroacetic acid salt

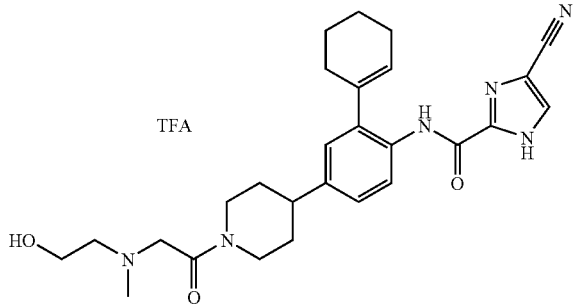

A solution of 4-cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt (as prepared in Example 44, step (c), 50.0 mg, 0.085 mmol) in MeOH (3 mL) was treated with Na(OAc)₃BH (39.5 mg, 0.19 mmol) and 37% aqueous formaldehyde (8.2 μL, 0.10 mmol). The mixture was stirred at room temperature for 5.5 h, and the solvents were removed in vacuo. Reverse phase HPLC (C-18 column) (10% to 50% acetonitrile in water with 0.1% TFA over 30 min) afforded the title compound (19.5 mg, 47%) as a white solid. H-NMR (CD₃OD; 400 MHz): δ 8.12 (d, 1H, J=8.4 Hz), 8.02 (s, 1H), 7.19 (dd, 1H, J=8.4, 2.0 Hz), 7.09 (d, 1H, J=2.0 Hz), 5.84-5.79 (m, 1H), 4.72-4.64 (m, 1H), 4.39-4.23 (m, 2H), 3.84-3.79 (m, 1H), 3.31-3.21 (m, 1H), 3.03-2.94 (m, 6H), 2.92-2.80 (m, 2H), 4H), 2.00-1.90 (m, 2H), 1.90-1.76 (m, 5H), 1.78-1.59 (m, 2H). LC-MS (ESI, m/z): Calcd. for $C_{27}H_{34}N_6O_3$ 491.3 (M+H), found 491.2.

EXAMPLE 46

4-Cyano-1H-imidazole-2-carboxylic acid [4-(1-acetyl-piperidin-4-yl)-2-(1,2,5,6-tetrahydro-pyridin-3-yl)-phenyl]-amide trifluoroacetic acid salt

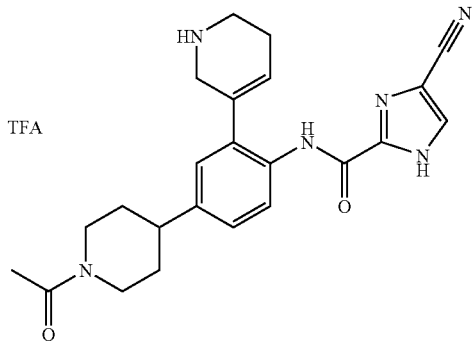

a) 5-Trifluoromethanesulfonyloxy-3,6-dihydro-2H-pyridine-1-carboxylic acid tert-butyl ester

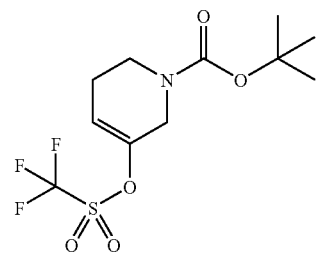

A solution of LDA (23.4 mL, 35.1 mmol, 1.5 M in cyclohex) in THF (50 mL) was cooled to −78° C. under Ar. The solution was treated with 3-oxo-piperidine-1-carboxylic acid tert-butyl ester (5.00 g, 25.1 mmol) as a solution in THF (15 mL) via drop wise addition and stirred for 15 min. The mixture was treated with 1,1,1-trifluoro-N-phenyl-N-[(trifluoromethyl)sulfonyl]methanesulfonimide (12.5 g, 35.1 mmol) as a solution in THF (40 mL). The mixture was allowed to warm to room temperature and stir 2.5 h. The reaction was quenched with saturated aqueous NaHCO₃, diluted with Et₂O, and washed with water. The organic layer was dried over MgSO₄ and concentrated in vacuo. Silica gel chromatography (5% EtOAc in hexanes) afforded the title compound (2.45 g, 30%) as a colorless oil. $^1$H-NMR (CDCl₃; 400 MHz): δ 5.97-5.89 (m, 1H), 4.09-4.01 (m, 2H), 3.54-3.45 (m, 2H), 2.36-2.26 (m, 2H), 1.48 (s, 9H). LC-MS (ESI, m/z): Calcd. for $C_{11}H_{16}F_3NO_5S$ 332.1 (M+H), found 332.1.

b) 5-(4,4,5,5-Tetramethyl-[1,3,2]dioxaborolan-2-yl)-3,6-dihydro-2H-pyridine-1-carboxylic acid tert-butyl ester

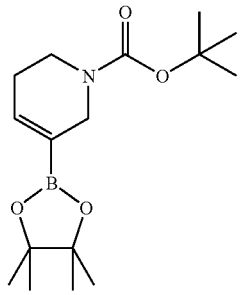

PdCl₂dppf (0.16 g, 0.22 mmol), KOAc (2.18 g, 22.2 mmol), 4,4,5,5,4',4',5',5'-octamethyl-[2,2']bi[[1,3,2]dioxaborolanyl] (2.07 g, 8.13 mmol), and dppf (0.12 g, 0.22 mmol) were placed in a round-bottomed flask, and the flask was flushed with Ar. A degassed solution of 5-trifluoromethanesulfonyloxy-3,6-dihydro-2H-pyridine-1-carboxylic acid tert-butyl ester (as prepared in the previous step, 2.45 g, 7.40 mmol) in dioxane (70 mL) was added to the flask and heated to 80° C. for 16 h. The mixture was filtered through a glass-fritted funnel to remove the solid KOAc, and the filtrate was concentrated in vacuo. Silica gel chromatography (5% EtOAc in hexanes) afforded the title compound (1.62 g, 71%) as a colorless oil. ¹H-NMR (CDCl₃; 400 MHz): δ 6.69-6.60 (m, 1H), 3.98 (br s, 2H), 3.49-3.42 (m, 2H), 2.24-2.16 (m, 2H), 1.47 (s, 9H), 1.27 (s, 12H). LC-MS (ESI, m/z): Calcd. for $C_{18}H_{28}BNO_4$ 310.2 (M+H), found 311.0.

c) 4-(4-Nitro-phenyl)-3,6-dihydro-2H-pyridine-1-carboxylic acid tert-butyl ester

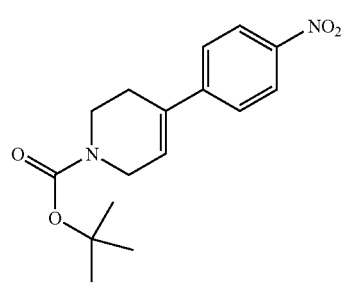

The title compound was prepared by the Suzuki coupling procedure of Example 35, step (b) using 4-nitrophenylboronic acid (167 mg, 1.00 mmol) and 4-trifluoromethanesulfonyloxy-3,6-dihydro-2H-pyridine-1-carboxylic acid tert-butyl ester (as prepared in Example 13, step (a), 295 mg, 1.00 mmol). Silica gel chromatography (10% EtOAc in hexanes) afforded the title compound (273 mg, 90%) as an oil. ¹H-NMR (CDCl₃; 400 MHz): δ 8.19 (d, 2H, J=8.8 Hz), 7.50 (d, 2H, J=8.8 Hz), 6.23 (m, 1H), 4.12 (m, 2H), 3.66 (m, 2H), 2.54 (m, 2H), 1.49 (s, 9H).

d) 1-[4-(4-Amino-phenyl)-piperidin-1-yl]-ethanone

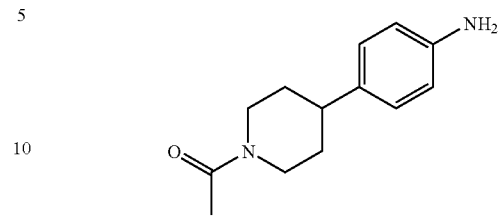

A solution of 4-(4-nitro-phenyl)-3,6-dihydro-2H-pyridine-1-carboxylic acid tert-butyl ester (as prepared in the previous step, 304 mg, 1.00 mmol) in a 1:1 mixture of DCM/TFA (10 mL) was stirred at room temperature for 3 h and concentrated. The residue was dried in vacuo overnight, was taken up in CH₂Cl₂ (10 mL) and was cooled to 0° C. To this solution, Et₃N (280 μL, 2 mmol) was added drop wise, followed by acetic anhydride (102 μL, 1 mmol). The resulting mixture was stirred at 0° C. for 1 h and allowed to warm to room temperature. The reaction mixture was washed with brine, and the organic layer was separated, dried and concentrated. The resulting product was reduced to obtain the title compound (143 mg, 65%) using a procedure similar to Example 4, step (d). ¹H-NMR (CDCl₃; 400 MHz): δ 6.97 (d, 2H, J=8.4 Hz), 6.64 (d, 2H, J=8.4 Hz), 4.75 (m, 1H), 3.93 (m, 1H), 3.13 (m, 3H), 2.66 (m, 2H), 2.12 (s, 3H), 1.84 (m, 2H), 1.57 (m, 2H).

e) 1-[4-(4-Amino-3-bromo-phenyl)-piperidin-1-yl]-ethanone

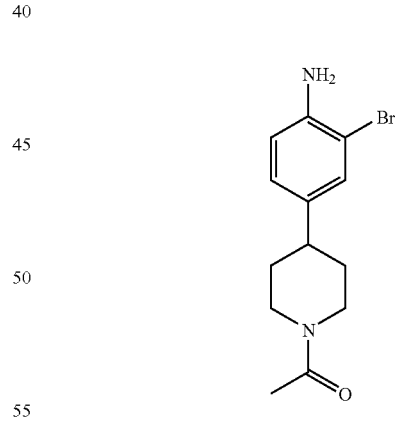

A solution of 1-[4-(4-amino-phenyl)-piperidin-1-yl]-ethanone (as prepared in the previous step, 0.36 g, 1.66 mmol) in CH₂Cl₂ (10 mL) was cooled to −78° C. and treated with NBS (0.28 g, 1.58 mmol) as a suspension in CH₂Cl₂ (4 mL). The reaction was allowed to warm to room temperature and stir for 30 min. The reaction was diluted with CH₂Cl₂ and washed with saturated aqueous NaHCO₃. The organic layer was dried over MgSO₄ and concentrated in vacuo. The crude material was used directly in the next reaction. LC-MS (ESI, m/z): Calcd. for $C_{13}H_{17}BrN_2O$ 297.1 (M+H), found 297.1.

f) 5-[5-(1-Acetyl-piperidin-4-yl)-2-amino-phenyl]-3,6-dihydro-2H-pyridine-1-carboxylic acid tert-butyl ester

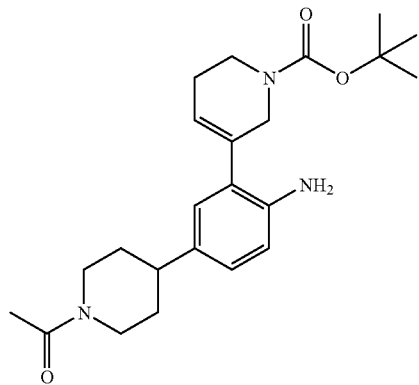

A solution of 5-(4,4,5,5-tetramethyl-[1,3,2]dioxaborolan-2-yl)-3,6-dihydro-2H-pyridine-1-carboxylic acid tert-butyl ester (as prepared in Example 46, step (b), 0.62 g, 2.02 mmol) and 1-[4-(4-amino-3-bromo-phenyl)-piperidin-1-yl]-ethanone (as prepared in the previous step, 0.20 g, 0.67 mmol) in toluene:EtOH (2:1, 9 mL) was treated with 2.0 M aqueous $Na_2CO_3$ (2.7 mL, 5.38 mmol) and was degassed with sonication under Ar. The mixture was heated to 80° C., treated with $Pd(PPh_3)_4$ (54 mg, 0.05 mmol), and stirred at 80° C. for 4.5 h. The reaction was cooled to room temperature, diluted with EtOAc, and washed with saturated aqueous $NaHCO_3$. The organic layer was dried over $MgSO_4$ and concentrated in vacuo to afford the title compound (0.25 g, 93%) as an off-white solid. LC-MS (ESI, m/z): Calcd. for $C_{23}H_{33}N_3O_3$ 422.2 (M+Na), found 422.0.

g) 5-(5-(1-Acetyl-piperidin-4-yl)-2-{[4-cyano-1-(2-tyimethylsilanyl-ethoxymethyl)-1H-imidazole-2-carbonyl]-amino}-phenyl)-3,6-dihydro-2H-pyridine-1-carboxylic acid tert-butyl ester

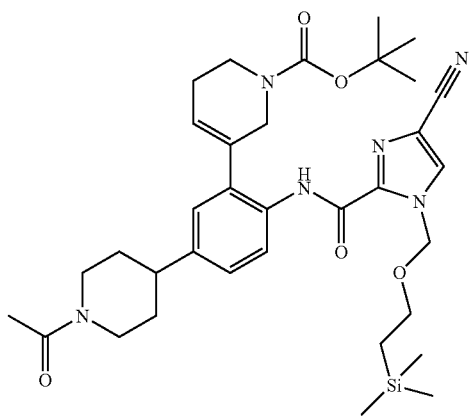

A solution of 5-[5-(1-acetyl-piperidin-4-yl)-2-amino-phenyl]-3,6-dihydro-2H-pyridine-1-carboxylic acid tert-butyl ester (as prepared in the previous step, 0.25 g, 0.63 mmol) in $CH_2Cl_2$ was treated with PyBroP (0.44 g, 0.94 mmol) and 4-cyano-1-(2-trimethylsilanyl-ethoxymethyl)-1H-imidazole-2-carboxylic acid, potassium salt (as prepared in Example 3, step (d), 0.21 g, 0.69 mmol). The resulting slurry was cooled to 0° C. and treated with DIEA (0.33 mL, 1.88 mmol). The ice bath was removed and the mixture stirred at room temperature for 18 h. The reaction was diluted with $CH_2Cl_2$ and washed with saturated aqueous $NaHCO_3$. The organic layer was dried over $MgSO_4$ and concentrated in vacuo. Silica gel chromatography (25-45% EtOAc in hexanes then 100% EtOAc) afforded the title compound (399 mg, 98%) as a white solid. LC-MS (ESI, m/z): Calcd. for $C_{34}H_{48}N_6O_5Si$ 649.4 (M+H), found 649.9.

h) 4-Cyano-1H-imizazole-2-carboxylic acid [4-(1-acetyl-piperidin-4-yl)-2-(1,2,5,6-tetrahydro-pyridin-3-yl)-phenyl]-amide trifluoroacetic acid salt

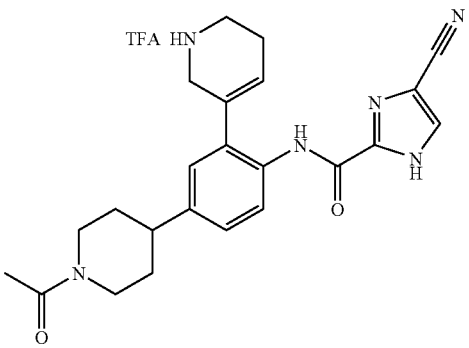

A solution of 5-(5-(1-acetyl-piperidin-4-yl)-2-{[4-cyano-1-(2-trimethylsilanyl-ethoxymethyl)-1H-imidazole-2-carbonyl]-amino}-phenyl)-3,6-dihydro-2H-pyridine-1-carboxylic acid tert-butyl ester (as prepared in the previous step, 0.40 g, 0.61 mmol) in $CH_2Cl_2$ (20 mL) and EtOH (0.4 mL) was treated with TFA (3 mL). The solution was stirred at room temperature for 0.5 h. The solvents were evaporated in vacuo, and the residue was immediately taken up in EtOH (25 mL) and stored at 5° C. for 11 h. The solution was concentrated in vacuo, and the residue was taken up in $CH_2Cl_2$ (20 mL) and EtOH (0.4 mL) then treated with TFA (6 mL). The reaction was stirred at room temperature for 2 h, and the solvents were evaporated in vacuo. Reverse phase HPLC (C-18 column) (10 to 80% acetonitrile in water with 0.1% TFA over 30 min) afforded the title compound (56.9 mg, 22%) as a white solid. $^1$H-NMR ($CDCl_3$; 400 MHz): δ 8.06 (s, 1H), 7.81 (d, 1H, J=8.4 Hz), 7.32 (d, 1H, J=8.4 Hz), 7.22 (s, 1H), 6.10-6.03 (m, 1H), 4.74-4.64 (m, 2H), 4.11-4.02 (m, 1H), 3.95 (s, 2H), 3.50-3.37 (m, 2H), 3.29-3.20 (m, 1H), 2.93-2.82 (m, 1H), 2.80-2.69 (m, 1H), 2.62-2.53 (m, 2H), 2.16 (s, 3H), 1.98-1.84 (m, 2H), 1.78-1.54 (m, 2H). LC-MS (ESI, m/z): Calcd. for $C_{23}H_{26}N_6O_2$ 419.2 (M+H), found 419.2.

EXAMPLE 47

(4-{4[(4-Cyano-1H-imidazole-2-carbonyl)-amino]-3-cyclohex-1-enyl-phenyl}-piperidin-1-yl)-acetic acid trifluoroacetic acid salt

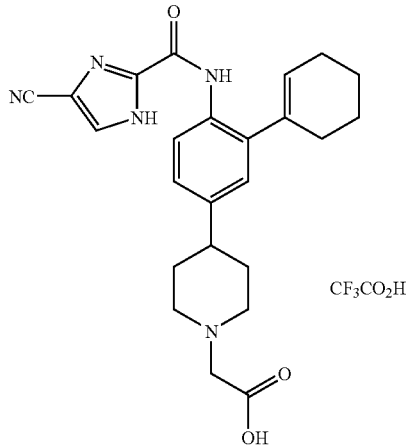

A flask was charged with 4-cyano-1H-imidazole-2-carboxylic acid (2-cyclohex-1-enyl-4-piperidin-4-yl-phenyl)-amide TFA salt (33 mg, 0.067 mmol) (as prepared in Example 14, step (b)), t-butyl bromoacetate (10 μL, 0.067 mmol), NEt₃ (20 μL, 0.135 mmol) and 0.25 mL of DCM and stirred for 10 h at 25° C. The reaction mixture was loaded on a 5 g SPE cartridge (silica) and 23 mg (70%) of (4-{4-[(4-cyano-1H-imidazole-2-carbonyl)-amino]-3-cyclohex-1-enyl-phenyl}-piperidin-1-yl)-acetic acid tert-butyl ester was eluted with 25% EtOAc/DCM. This compound was dissolved in 1 mL of DCM and 20 μL of EtOH and 1 mL of TFA were added and the reaction stirred for 3 h at 25° C. The title compound was purified by RP-HPLC (C18), eluting with 30-50% CH₃CN in 0.1% TFA/H₂O over 12 min to give 10 mg (40%) of a white solid. $^1$H-NMR (400 MHz, CD₃OD): δ 8.16 (d, 1H), 8.02 (s, 1H), 7.22 (dd, 1H), 7.10 (d, 1H), 5.72 (m, 1H), 4.04. (s, 2H), 3.76 (m, 2H), 3.22 (m, 2H), 2.90 (m, 1H), 2.29 (m, 4H), 2.10 (m, 4H), 1.82 (m, 4H). Mass spectrum (ESI, m/z): Calcd. for $C_{24}H_{27}N_5O_3$, 434.2 (M+H), found 434.2.

EXAMPLE 48

4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt

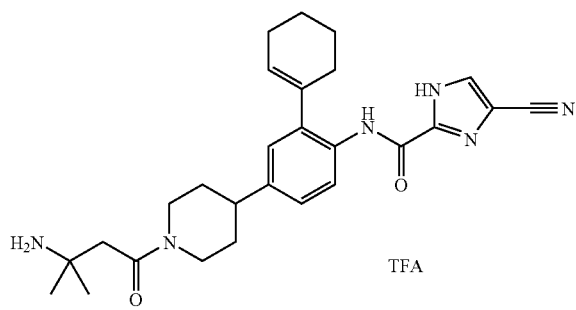

a) [3-(4-{4-[(4-Cyano-1H-imidazole-2-carbonyl)-amino]-3-cyclohex-1-enyl-phenyl}-piperidin-1-yl)-1,1-dimethyl-3-oxo-propyl]-carbamic acid tert-butyl ester

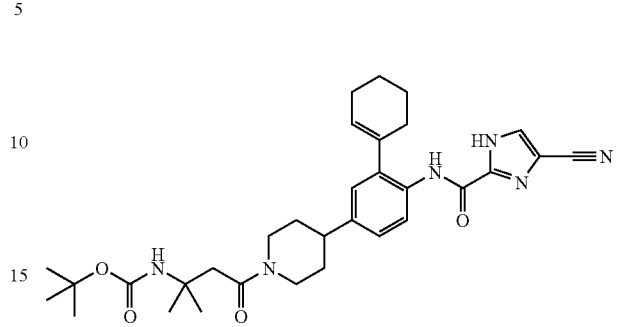

To a mixture of 4-cyano-1H-imidazole-2-carboxylic acid (2-cyclohex-1-enyl-4-piperidin-4-yl-phenyl)-amide trifluoroacetic acid salt (as prepared in Example 14, step (b), 40.0 mg, 0.0818 mmol), 3-tert-butoxycarbonylamino-3-methyl-butyric acid (*J. Med. Chem.*, 34(2), 633-642, (1991), 21.4 mg, 0.0981 mmol) and PyBroP (55.0 mg, 0.0981 mmol) in dichloroethane (2 mL) was added DIEA (43 μL, 0.25 mmol) and the resulting mixture was stirred at RT for 1 day under Ar. The mixture was diluted with EtOAc (30 mL) and washed with H₂O (2×10 mL), brine (10 mL), dried over Na₂SO₄ and then concentrated in vacuo. The residue was purified by flash chomatography (silica gel, 10-40% EtOAc/hexane) to give 33.0 mg (70%) of the title compound as a colorless oil. Mass spectrum (ESI, m/z): Calcd. for $C_{32}H_{42}N_6O_4$, 575.3 (M+H), found 574.8.

b) 4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt

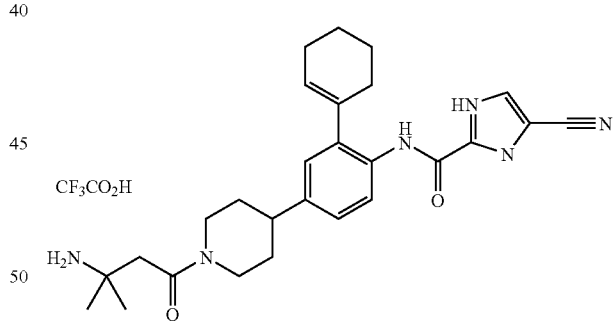

To a solution of [3-(4-{4-[(4-cyano-1H-imidazole-2-carbonyl)-amino]-3-cyclohex-1-enyl-phenyl}-piperidin-1-yl)-1,1-dimethyl-3-oxo-propyl]-carbamic acid tert-butyl ester (33.0 mg, 0.0574 mmol) (as prepared in the previous step) in 3 mL of DCM and 0.10 mL EtOH at 0° C. was added 1.0 mL of TFA, the mixture was warmed to RT and stirred for 3 h. The reaction was diluted with 3 mL of n-PrOH and then concentrated in vacuo. The residue was purified by flash chomatography (silica gel, 3-8% MeOH/DCM) to give 33.5 mg (99%) of the title compound as a white solid. $^1$H-NMR (400 MHz, CDCl₃): δ 13.3 (s, 1H), 9.52 (s, 1H), 8.57 (br s, 3H), 8.26 (d, 1H, J=8.6 Hz), 7.69 (s, 1H), 7.02 (dd, 1H, J=8.6, 1.7 Hz), 6.98 (d, 1H, J=1.7 Hz), 5.78 (m, 1H), 4.67 (br d, 1H, J=13.4 Hz), 3.88 (br d, 1H, J=13.4 Hz), 3.10 (m, 1H), 2.55-2.85 (m, 4H), 2.23 (m, 4H), 1.72-2.01 (m, 8H), 1.50 (s, 6H). Mass spectrum (ESI, m/z): Calcd. for $C_{27}H_{34}N_6O_2$, 475.3 (M+H), found 475.1.

EXAMPLE 49

4H-[1,2,4]-triazole-3-carboxylic acid (2-cyclohex-1-enyl-4-piperidin-4-yl-phenyl)-amide bis trifluoroacetic acid salt

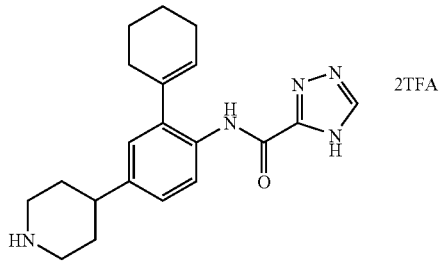

a) 1-(2-Trimethylsilanyl-ethoxymethyl)-1H-[1,2,4]-triazole-3-carboxylic acid methyl ester

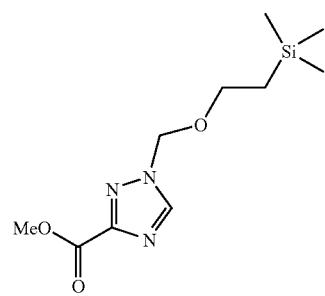

To a suspension of NaH (60% dispersion) (200 mg, 5.00 mmol) in DMF (5 mL) at 0° C., a solution of methyl-1H-1,2,4-triazolecarboxylate (635 mg, 5.00 mmol) in DMF (5 mL) was added dropwise. The resulting suspension was stirred at the same temperature for 30 min and treated with SEMCl (0.90 mL, 5.0 mmol). The resulting solution was stirred at RT for 30 min and poured onto ice. The product was extracted with ether (3×20 mL). The ether layers were combined, dried (Na$_2$SO$_4$) and concentrated in vacuo. The residue obtained was chromatographed on silica (10% EtOAc/hexane) to obtain the title compound (530 mg, 41%). Mass spectrum (ESI, m/z): Calcd. for $C_{10}H_{19}N_3O_3Si$, 258.1 (M+H), found 258.2.

b) 4-(3-Cyclohex-1-enyl-4-{[-(2-trimethylsilanyl-ethoxymethyl)-1H-[1,2,4-]triazole-3-carbonyl]-amino}-phenyl)-piperidine-1-carboxylic acid tert-butyl ester

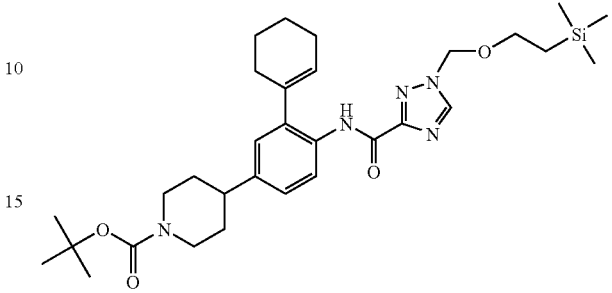

To a solution of 1-(2-trimethylsilanyl-ethoxymethyl)-1H-[1,2,4]-triazole-3-carboxylic acid methyl ester (as prepared in the previous step, 257 mg, 1.00 mmol) in EtOH (2 mL), 2 N KOH (0.5 mL, 1 mmol) was added. The resulting solution was stirred at RT for 20 min and concentrated in vacuo. The residue obtained was suspended in ether (10 mL) and sonicated for 5 min. The ether was then removed in vacuo and the resulting residue was dried for 4 hr to obtain 1-(2-trimethylsilanyl-ethoxymethyl)-1H-[1,2,4]-triazole-3-carboxylic acid potassium salt (273 mg, 97%) which was directly used in the next step without any further purification.

A mixture of 1-(2-trimethylsilanyl-ethoxymethyl)-1H-[1,2,4]-triazole-3-carboxylic acid potassium salt (as prepared above, 28 mg, 0.10 mmol), DIEA (34 µL, 0.20 mmol), 4-(4-amino-3-cyclohex-1-enyl-phenyl)-piperidine-1-carboxylic acid tert-butyl ester (as prepared in Example 14, step (b), 35.6 mg, 0.100 mmol) and PyBroP (69.9 mg, 0.150 mmol) in DCM (2 mL) was stirred at RT for 12 h. The reaction mixture was diluted with DCM (5 mL) and washed with saturated aqueous NaHCO$_3$ (10 mL) and water (10 mL). The organic layer was separated, dried (Na$_2$SO$_4$) and concentrated in vacuo The product was chromatographed on silica (20-40% EtOAc/hexane) to obtain the title compound (31.9 mg, 55%). Mass psectrum (ESI, m/z): Calcd. for $C_{13}H_{47}N_5O_4Si$, 481.2 (M-BOC+2H), found. 481.2.

c) 4H-[1,2,4-]-triazole-3-carboxylic acid (2-cyclohex-1-enyl-4-piperidin-4-yl-phenyl)-amide bis trifluoroacetic acid salt

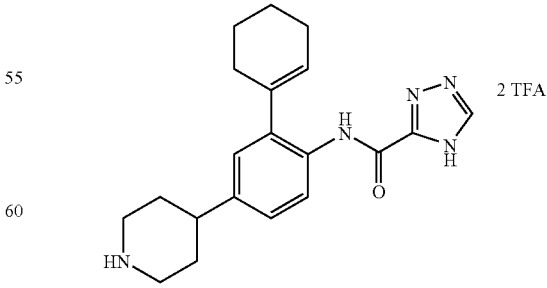

To a solution of 4-(3-cyclohex-1-enyl-4-{[1-(2-trimethylsilanyl-ethoxymethyl)-1H-[1,2,4]-triazole-3-carbonyl]-amino}-phenyl)-piperidine-1-carboxylic acid tert-butyl ester (as prepared in the previous step, 81.9 mg, 0.140 mmol) in DCM (0.4 mL) and EtOH (13 μL), was added TFA (0.13 mL). The resulting solution was stirred at RT for 3 h and concentrated in vacuo. The residue obtained was dried under vacuum for 1 h, suspended in ether (10 mL) and sonicated for 5 min. The solid formed was collected by suction filtration to obtain the title compound (56 mg, 68%). $^1$H-NMR (CD$_3$OD; 400 MHz): δ 8.53 (br s, 1H), 8.20 (d, 1H, J=8.4 Hz), 7.21 (dd, 1H, J=8.4, 2.1 Hz), 7.11 (d, 1H, J=2.1 Hz), 5.83 (br s, 1H), 3.45 (m, 2H), 3.19 (m, 2H), 2.98 (m, 1H), 2.28 (m, 4H), 2.14 (m, 2H), and 1.95-1.75 (m, 6H). Mass spectrum (ESI, m/z): Calcd. for C$_{20}$H$_{25}$N$_5$O, 352.4 (M+H), found 352.2.

EXAMPLE 50

5-Chloro-4H-[1,2,4]-triazole-3-carboxylic acid (2-cyclohex-1-enyl-4-piperidin-4-yl-phenyl)-amide trifluoroacetic acid salt

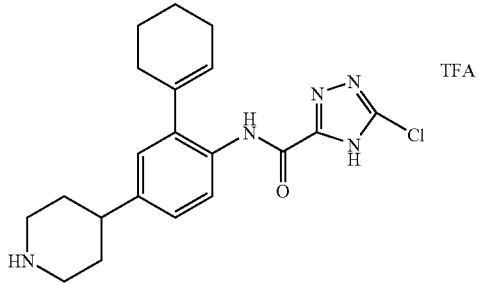

a) 5-Chloro-1-(2-trimethylsilanyl-ethoxymethyl)-1H-[1,2,4]-triazole-3-carboxylic acid methyl ester

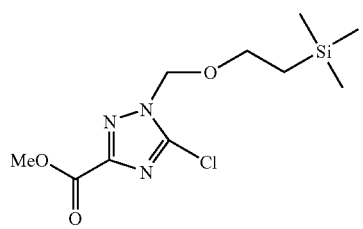

To a suspension of NaH (60% dispersion, 53.9 mg, 1.34 mmol) in DMF (5 mL) at 0° C., a solution of 5-chloro-1H-[1,2,4]-triazole-3-carboxylic acid methyl ester (*Bull. Pharm. Sci.*, 20(1): 47-61, (1997), 218 mg, 1.35 mmol) in DMF (10 mL) was added dropwise. The resulting suspension was stirred at the same temperature for 30 min and then treated with SEMCl (0.24 mL, 1.4 mmol). The resulting solution was stirred at RT for 30 min and poured onto ice. The mixture was extracted with ether (3×20 mL) and the ether layers were combined, dried (Na$_2$SO$_4$) and concentrated in vacuo. The residue obtained was chromatographed on silica (10% EtOAc/hexane) to obtain the title compound (227 mg, 58%). Mass spectrum (ESI, m/z): Calcd. for C$_{10}$H$_{18}$ClN$_3$O$_3$Si, 292.0 and 294.0 (M+H), found 291.5 and 293.6.

b) 4-(4-{[5-Chloro-1-(2-trimethylsilanyl-ethoxymethyl)-1H-[1,2,4]-triazole-3-carbonyl]-amino}-3-cyclohex-1-enyl-phenyl)-piperidine-1-carboxylic acid tert-butyl ester

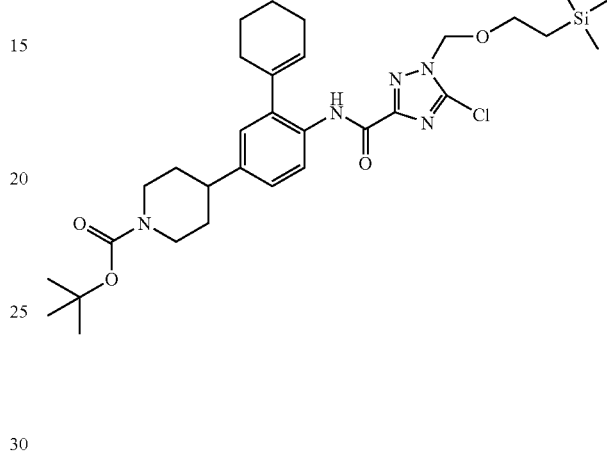

To a solution of 4-(4-{[5-chloro-1-(2-trimethylsilanyl-ethoxymethyl)-1H-[1,2,4]triazole-3-carboxylic acid methyl ester (as prepared in the previous step, 227 mg, 0.780 mmol) in EtOH (2 mL), 2 N KOH (0.4 mL, 0.8 mmol) was added. The resulting solution was stirred at RT for 20 min and concentrated in vacuo. The residue obtained was suspended in ether (10 mL) and sonicated for 5 min. The ether was then removed and the resulting residue was dried in vacuo for 4 h to obtain 4-(4-{[5-chloro-1-(2-trimethylsilanyl-ethoxymethyl)-1H-[1,2,4]triazole-3-carboxylic acid potassium salt (223 mg, 91%) which was directly used in the next step without any further purification.

A mixture of 4-(4-{[5-chloro-1-(2-trimethylsilanyl-ethoxymethyl)-1H-[1,2,4]-triazole-3-carboxylic acid potassium salt (as prepared above, 35 mg, 0.10 mmol), DIEA (34 μL, 0.10 mmol), 4-(4-amino-3-cyclohex-1-enyl-phenyl)-piperidine-1-carboxylic acid tert-butyl ester (as prepared in Example 14, step (b), 35.6 mg, 0.100 mmol) and PyBroP (69.9 mg, 0.150 mmol) in DCM (2 mL) was stirred at RT for 12 h. The reaction mixture was diluted with DCM (5 mL) and washed with saturated aqueous NaHCO$_3$ (10 mL) and water (10 mL). The organic layer was separated, dried (Na$_2$SO$_4$) and concentrated in vacuo The product was chromatographed on silica (20-40% EtOAc/hexane) to obtain the title compound (52 mg, 85%). $^1$H-NMR (CDCl$_3$; 400 MHz): δ 9.60 (s, 1H), 8.29 (d, 1H, J=8.4 Hz), 7.18 (dd, 1H, J=8.4, 2.2 Hz), 7.13 (d, 1H, J=2.2 Hz), 5.99 (s, 2H), 5.84 (br s, 1H), 4.18-4.25 (m, 2H), 3.72-3.76 (m, 2H), 2.58-2.67 (m, 2H), 2.51-2.64 (m, 1H), 2.18-2.33 (m, 4H), 1.78-1.92 (m, 6H), 1.55-1.65 (m, 2H), 1.49 (s, 9H), 0.93-0.98 (m, 2H), 0.10 (s, 9H).

c) 5-Chloro-1H-[1,2,4-]-triazole-3-carboxylic acid (2-cyclohex-1-enyl-4-piperidin-4-yl-phenyl)-amide trifluoroacetic acid salt

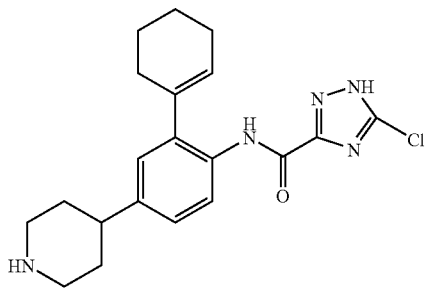

To a solution of 4-(4-{[5-chloro-1-(2-trimethylsilanyl-ethoxymethyl)-1H-[1,2,4]-triazole-3-carbonyl]-amino}-3-cyclohex-1-enyl-phenyl)-piperidine-1-carboxylic acid tert-butyl ester (as prepared in the previous step, 63.3 mg, 0.102 mmol) in DCM (0.5 mL) and EtOH (11 μL) was added TFA (0.1 mL). After stirring the resulting mixture at RT for 12 h, another 0.1 mL of TFA was added. The reaction mixture was stirred for an additional 5 h at RT, the solvents were evaporated, and the title compound was purified by RP-HPLC (C18) eluting with 20-70% CH$_3$CN in 0.1% TFA/H$_2$O over 20 min to obtain the title compound (30 mg, 58%). $^1$H-NMR (CD$_3$OD; 400 MHz): δ 8.14 (d, 1H, J=8.4 Hz), 7.20 (dd, 1H, J=8.4, 2.1 Hz), 7.13 (d, 1H, J=2.1 Hz), 5.82 (br s, 1H), 3.45 (m, 2H), 3.19 (m, 2H), 2.98 (m, 1H), 2.28 (m, 4H), 2.14 (m, 2H), and 1.95-1.75 (m, 6H). Mass spectrum (ESI, m/z): Calcd. for C$_{20}$H$_{24}$ClN$_5$O, 386.1 and 388.1 (M+H), found 386.2 and 388.1.

EXAMPLE 51

5-Cyano-1H-imidazole-2-carboxylic acid [2-cyclohex-1-enyl-4-(cis-2,6-dimethyl-piperidin-4-yl)-phenyl]-amide bis trifluoroacetic acid salt and 5-cyano-1H-imidazole-2-carboxylic acid [2-cyclohex-1-enyl-4-(trans-2,6-dimethyl-piperidin-4-yl)-phenyl]-amide bis trifluoroacetic acid salt

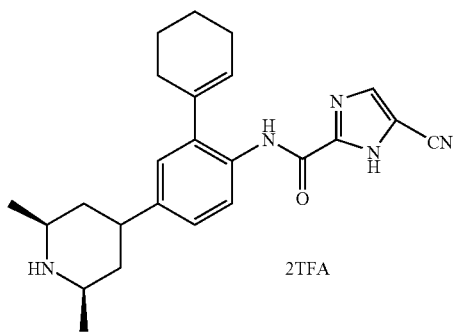

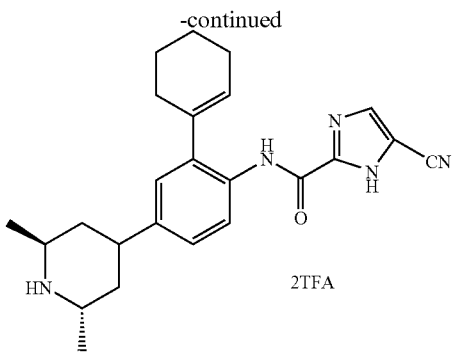

a) Cis/trans 2,6-Dimethyl-4-oxo-piperidine-1-carboxylic acid tert-butyl ester

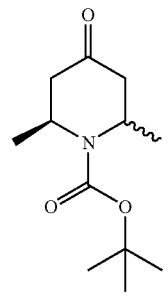

A solution of cis/trans-2,6-dimethylpiperidinone (*Coll. Czech. Chem. Commun.*: 31(11), 4432-41, (1966), 1.27 g, 10.0 mmol) in ether (100 mL) was treated with aq 1 N NaOH (11 mL, 11 mmol) and (BOC)$_2$O (2.18 g, 10.0 mmol). The resulting mixture as stirred at RT for 48 hr. The ether layer was separated, dried and concentrated. The residue was chromatographed on silica (10% EtOAc-hexane) to obtain the title compound (1.10 g, 50%): LC-MS (ESI, m/z): Calcd. for C$_{12}$H$_{21}$NO$_3$, 128.1 (M-BOC+2H), found 128.1.

b) 4-(4-Amino-phenyl)-cis/trans 2,6-dimethyl-piperidine-1-carboxylic acid tert-butyl ester

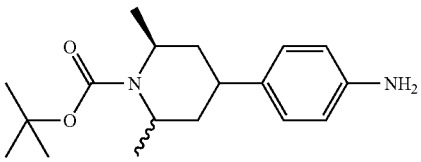

A solution of cis/trans N-Boc-2,6-dimethylpiperidinone (as prepared in the previous step, 1.14 g, 5.00 mmol) in THF (20 mL) was cooled to −78° C. and treated with LDA (1.5 M solution in cyclohex, THF and ethylbenzene, 4.4 mL, 6.5 mmol) under Ar. The resulting mixture was stirred at the same temperature for 30 min and treated with N-phenyltrifluoromethanesulfonimide (2.34 g, 6.55 mmol) in THF (20 mL). The reaction mixture was stirred for another 30 min and allowed to warm to RT. After 30 min. at RT the reaction mixture was concentrated in vacuo and the residue was taken up in ether (20 mL) and washed with cold water (2×10 mL). The ether layer was dried (Na$_2$SO$_4$) and concentrated to afforded cis/trans-2,6-dimethyl-4-trifluoromethanesulfonyloxy-3,6-dihydro-2H-pyridine-1-carboxylic acid tert-butyl ester (890 mg, 49%) which was directly used in next step.

The title compound was then prepared according to the Suzuki coupling procedure of Example 35, step (b) using 4-aminophenylboronic acid (219 mg, 1.00 mmol) and cis/trans-2,6-dimethyl-4-trifluoromethanesulfonyloxy-3,6-dihydro-2H-pyridine-1-carboxylic acid tert-butyl ester (as prepared above, 321 mg, 1.00 mmol). Silica gel chromatography (10-20% EtOAc/hexanes) afforded 4-(4-amino-phenyl)-2,6-dimethyl-3,6-dihydro-2H-pyridine-1-carboxylic acid tert-butyl ester (172 mg, 57%): Mass spectrum (ESI, m/z): Calcd. for C$_{18}$H$_{26}$N$_2$O$_2$, 303.2 (M+H) found 303.1.

A solution of 4-(4-amino-phenyl)-2,6-dimethyl-3,6-dihydro-2H-pyridine-1-carboxylic acid tert-butyl ester (as prepared above, 380 mg, 1.25 mmol) in MeOH (10 mL) was hydrogenated over 10% Pd/C (190 mg) at 20 psi for 1 h. The solution was filtered through a pad of Celite and concentrated to give the title compound (360 mg, 94%). Mass spectrum (ESI, m/z): Calcd. for C$_{18}$H$_{28}$N$_2$O$_2$, 305.2 (M+H), found 305.6.

c) 4-(4-Amino-3-cyclohex-1-enyl-phenyl)-cis/trans 2,6-dimethyl-piperidine-1-carboxylic acid tert-butyl ester

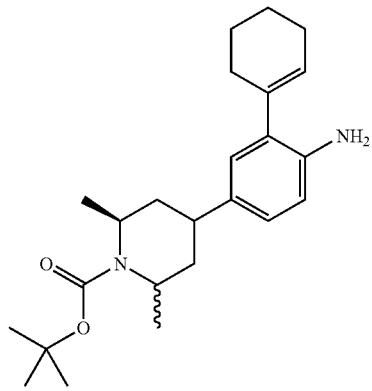

To a solution of 4-(4-amino-phenyl)-2,6-dimethyl-piperidine-1-carboxylic acid tert-butyl ester (as prepared in previous step, 334 mg, 1.09 mmol) in DCM (10 mL) was added NBS (195 mg, 1.09 mmol) and the reaction mixture was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo to obtain 4-(4-amino-3-bromo-phenyl)-cis/trans-2,6-dimethyl-piperidine-1-carboxylic acid tert-butyl ester (367 mg, 87%). Mass spectrum (ESI, m/z): Calcd. for C$_{18}$H$_{27}$BrN$_2$O$_2$, 327.0 and 329.0 (M-t-Bu+H), found 327.0 and 328.9.

The title compound was then prepared according to the Suzuki coupling procedure of Example 12, step (d) using cyclohexan-1-enyl boronic acid (157 mg, 1.25 mmol) and 4-(4-amino-3-bromo-phenyl)-2,6-dimethyl-piperidine-1-carboxylic acid tert-butyl ester (as prepared above, 382 mg, 1.00 mmol) and chromatographed on silica (20% EtOAc/hexanes) to afford 254 mg (66%). Mass spectrum (ESI, m/z): Calcd. for C$_{24}$H$_{36}$N$_2$O$_2$, 384.2 (M+H), found 385.1.

d) 4-(4-{[4-Cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester and 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester A mixture of 4-cyano-1-(2-trimethylsilanyl-ethoxymethyl)-1H-imidazole-2-carboxylic acid, potassium salt (as prepared in Example 3, step (d), 384 mg, 1.00 mmol), DIEA (0.34 µL, 2.0 mmol), 4-(4-amino-3-cyclohex-1-enyl-phenyl)-2,6-dimethyl-piperidine-1-carboxylic acid tert-butyl ester (as prepared in the previous step, 384 mg, 1.00 mmol) and PyBroP (699 mg, 1.50 mmol) in DCM (20 mL) was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo to obtained a mixture of the above two title compounds (321 mg, 50.7%). The mixture was chromatographed on silica (10-20% EtOAc/hexane) to obtain the individual title compounds.

4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester (31 mg). Mass spectrum (ESI, m/z): Calcd. for $C_{35}H_{51}N_5O_4Si$, 634.3 (M+H), found 634.1.

4-(4-{[4-cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester contaminated with 10% of 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester (290 mg). Mass spectrum (ESI, m/z): Calcd. for $C_{35}H_{51}N_5O_4Si$, 634.3 (M+H), found 634.1.

e) 5-Cyano-1H-imidazole-2-carboxylic acid [2-cyclohex-1-enyl-4-(cis-2,6-dimethyl-piperidin-4-yl)-phenyl]-amide bis trifluoroacetic acid salt and 5-cyano-1-H-imidazole-2-carboxylic acid [2-cyclohex-1-enyl-4-(trans-2,6-dimethyl-piperidin-4-yl)-phenyl]-amide bis trifluoroacetic acid salt

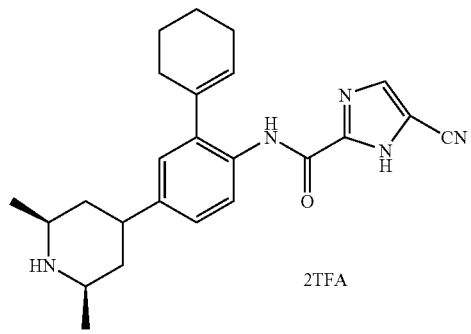

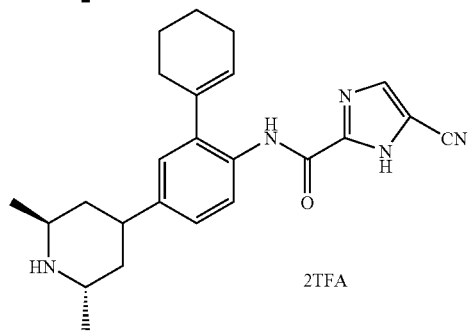

The title compounds were prepared from 290 mg (0.457 mmol) of 4-(4-{[4-cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester and 31 mg (0.048 mmol) of 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester according to the procedure in Example 14, step (b).

5-Cyano-1H-imidazole-2-carboxylic acid [2-cyclohex-1-enyl-4-(cis-2,6-dimethyl-piperidin-4-yl)-phenyl]-amide bis trifluoroacetic acid salt (93 mg, 32%): $^1$H-NMR (CD$_3$OD; 400 MHz): δ 8.17 (d, 1H, J=8.4 Hz), 8.03 (s, 1H), 7.22 (d, 1H, J=8.4 Hz), 7.11 (s, 1H), 5.72 (br s, 1H), 3.87 (m, 1H), 3.78 (m, 1H), 3.45 (m, 1H), 3.23 (m, 1H), 3.07 (m, 1H), 2.22 (m, 4H), 2.19 (m, 2H), 1.75-1.92 (m, 4H), 1.56 (m, 3H), 1.37 (m, 6H). Mass spectrum, ESI, n/z): Calcd. for $C_{24}H_{29}N_5O$, 404.2 (M+H), found 404.2.

5-Cyano-1H-imidazole-2-carboxylic acid [2-cyclohex-1-enyl-4-(trans-2,6-dimethyl-piperidin-4-yl)-phenyl]-amide bis trifluoroacetic acid salt (17.3 mg, 56%). $^1$H-NMR (CDCl$_3$; 400 MHz): δ 13.9 (br s, 1H), 10.3 (br s, 1H), 9.98 (s, 1H), 8.41 (d, 1H, J=8.4 Hz), 7.75 (br s, 1H), 7.26 (dd, 1H, J=8.4, 2.0 Hz), 7.15 (d, 1H, J=2 Hz), 5.92 (br s, 1H), 4.12 (m, 1H), 3.59 (m, 1H), 3.1-3.3 (m, 4H), 2.25-2.42 (m, 6H), 2.05-1.78 (m, 6H), 1.62 (d, 3H, J=7.1 Hz), 1.43 (d, 3H, J=6.3 Hz). Mass spectrum (ESI, m/z): Calcd. for $C_{24}H_{29}N_5O$, 404.2 (M+H), found 404.2.

EXAMPLE 52

5-Cyano-1H-imidazole-2-carboxylic acid {2-cyclohex-1-enyl-4-[1-(R)-(+)-(2,3-dihydroxy-propionyl)-piperidin-4-yl]-phenyl}-amide

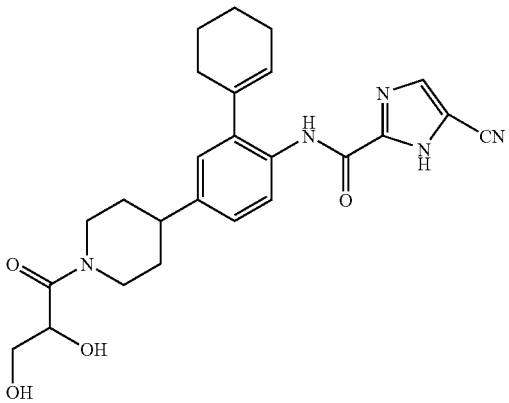

a) 5-Cyano-1H-imidazole-2-carboxylic acid {2-cyclohex-1-enyl-4-[1-(R)-(+)2,2-dimethyl-[1,3]dioxolane-4-carbonyl)-piperidin-4-yl]-phenyl}-amide

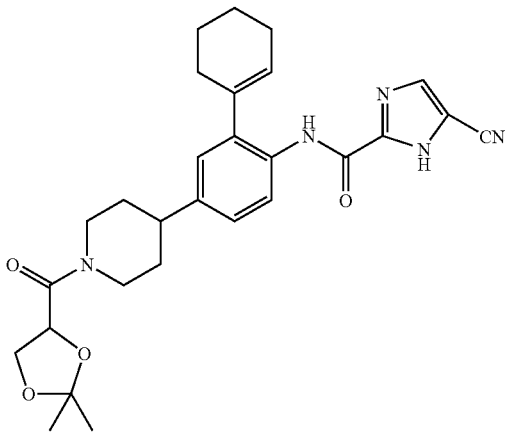

To a solution of methyl (R)-(+)-2,2-dimethyl-1,3-dioxolane-4-carboxylate (0.16 mL, 1.0 mmol) in MeOH (2 mL), 2 N KOH (0.5 mL, 1 mmol) was added. The resulting solution was stirred at RT for 20 min and concentrated in vacuo. The residue obtained was suspended in ether (10 mL) and sonicated for 5 min. The ether was then removed and the resulting residue was dried in vacuo for 4 h to obtain (R)-(+)-2,2-dimethyl-1,3-dioxolane-4-carboxylic acid potassium salt (173 mg, 94%) which was directly used in the next step without purification.

To a solution of 4-cyano-1H-imidazole-2-carboxylic acid (2-cyclohex-1-enyl-4-piperidin-4-yl-phenyl)-amide, trifluoroacetic acid salt (as prepared in Example 14, step (b), 40 mg, 0.08 mmol) in DCM (1.5 mL) was added to a mixture of (R)-(+)-2,2-dimethyl-1,3-dioxalane-4-carboxylic acid potassium salt (as prepared above, 18 mg, 0.090 mmol), EDCI (18.8 mg, 0.0900 mmol), HOBt (13.2 mg, 0.0900 mmol) and DIEA (42 μL, 0.24 mmol). The resulting mixture was stirred at RT for 6 h. Water (10 mL) was added and DCM layer was separated, dried (Na$_2$SO$_4$) and concentrated. The residue obtained was chromatographed on silica (2% MeOH/DCM) to obtain title compound (47 mg, 97%). Mass spectrum (ESI, m/z): Calcd. for C$_{28}$H$_{33}$N$_5$O$_4$, 504.2 (M+H), found 503.9.

b) 5-Cyano-1H-imidazole-2-carboxylic acid {2-cyclohex-1-enyl-4-[1-(R)-(+)-(2,3-dihydroxy-propionyl)-piperidin-4-yl]-phenyl}-amide

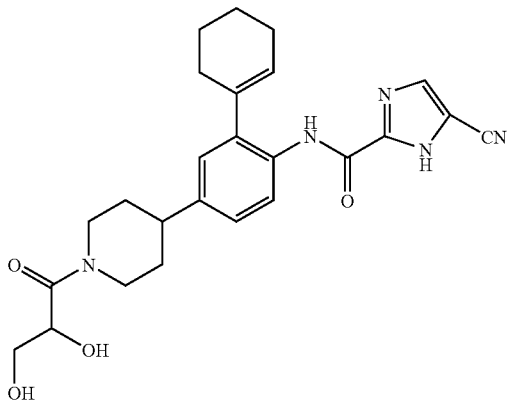

To a solution of 5-cyano-1H-imidazole-2-carboxylic acid {2-cyclohex-1-enyl-4-[1-(R)-(2,2-dimethyl-[1,3]dioxolane-4-carbonyl)-piperidin-4-yl]-phenyl}-amide (as prepared in the previous step, 45 mg, 0.090 mmol) in MeOH (1 mL) was added aq 2 N HCl (2 mL). The resulting mixture was stirred at RT for 12 hr. Solvents were removed in vacuo and the resulting residue was dried for 4 h. The ether (10 mL) was added and sonicated for 5 min. The ether was removed in vacuo and the residue was dried for 12 h to obtain the title compound (21.3 mg, 52%). $^1$H-NMR (DMSO; 400 MHz): δ 14.1 (br s, 1H), 9.85 (s, 1H), 8.32 (s, 1H), 7.92 (d, 1H, J=8.4Hz), 7.18 (dd, 1H, J=8.4,2.1 Hz), 7.13 (d, 1H, J=2.1 Hz), 5.72 (br s, 1H), 4.51 (m, 1H), 4.33 (m, 1H), 4.15 (m, 1H), 3.55 (m, 1H), 3.43 (m, 1H), 3.08 (m, 1H), 2.81 (m, 1H), 2.63 (m, 1H), 2.12-2.24 (m, 4H), 1.31-1.38 (m, 10 H). mass spectrum (ESI, m/z): Calcd. for C$_{25}$H$_{29}$N$_5$O$_4$, 464.2 (M+H), found 464.1.

EXAMPLE 53

5-Cyano-1H-imidazole-2-carboxylic acid [2-cyclohex-1-enyl-4-(1-methoxy-piperidin-4-yl)-phenyl]-amide trifluoroacetic acid salt

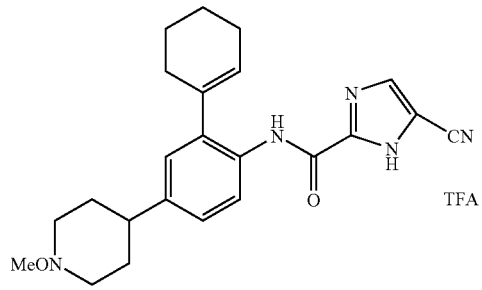

a) 4-(1-Methoxy-1,2,3,6-tetrahydro-pyridin-4-yl)-phenylamine

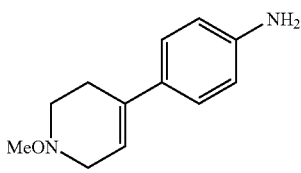

A solution of N-methoxypiperidinone (J. Org. Chem., 26, 1867, (1961), 650 mg, 5.00 mmol) in THF (20 mL)) was cooled to −78° C. and treated with LDA (1.5 M solution in cyclohex, THF and ethylbenzene, 4.3 mL, 6.4 mmol) under Ar. The resulting mixture was stirred at same temperature for 30 min and treated with N-phenyltrifluoromethanesulfonimide (2.3 g, 6.4 mmol) in THF (20 mL). The reaction mixture was stirred for another 30 min and allowed to warm to RT. After 30 min at RT, the reaction mixture was concentrated in vacuo and the residue obtained was taken up in EtOAc (20 mL) and washed with cold water (2×10 mL). EtOAc layer was dried (Na$_2$SO$_4$) and concentrated to afforded trifluoromethanesulfonic acid 1-methoxy-1,2,3,6-tetrahydro-pyridin-4-yl ester (980 mg, 71%) as a white foam which was directly used in next step The title compound was then prepared according to Suzuki coupling procedure of Example 35, step (b) using 4-aminophenylboronic acid (219 mg, 1.00 mmol) and trifluoromethanesulfonic acid 1-methoxy-1,2,3,6-tetrahydro-pyridin-4-yl ester (as prepared above, 261 mg, 1.00 mmol). Silica gel chromatography (20-50% EtOAc/hexanes) afforded 60 mg (29%). Mass spectrum (ESI, m/z): Calcd. for C$_{12}$H$_{16}$N$_2$O, 205.1 (M+H), found 205.2.

b) 2-Cyclohex-1-enyl-4-(1-methoxy-piperidin-4-yl)-phenylamine

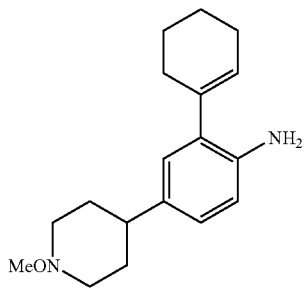

A solution of 4-(1-methoxy-1,2,3,6-tetrahydro-pyridin-4-yl)-phenylamine (as prepared in previous step) (40.8 mg, 0.200 mmol) in MeOH (5 mL) was hydrogenated over 10% Pd/C (20.4 mg) at 20 psi for 1 h. The solution was filtered through a pad of Celite and concentrated to give 4-(1-methoxy-piperidin-4-yl)-phenylamine (38 mg, 92%) which was directly used in the next step without purification.

To a solution of 4-(1-methoxy-piperidin-4-yl)-phenylamine (as prepared above, 42 mg, 0.20 mmol) in DCM (2 mL) was added NBS (36.2 mg, 0.20 mmol) and the reaction mixture was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo to obtain 2-bromo-4-(1-methoxy-1,2,3,6-tetrahydro-pyridin-4-yl)-phenylamine (43 mg, 74.5%) which was used in the next step without purification.

The title compound was then prepared according to Suzuki coupling procedure of Example 12, step (d) using cyclohex-1-enyl boronic acid (27.9 mg, 1.00 mmol) and 2-bromo-4-(1-methoxy-1,2,3,6-tetrahydro-pyridin-4-yl)-phenylamine (as prepared above, 44 mg, 0.15 mmol) and chromatographed on silica (20-50% EtOAc/hexanes) afforded 2-cyclohex-1-enyl-4-(1-methoxy-piperidin-4-yl)-phenylamine (33 mg, 74%). Mass spectrum, (ESI, m/z): Calcd. for C$_{18}$H$_{26}$N$_2$O, 287.2 (M+H), found 286.8.

c) 4-Cyano-1-(2-trimethylsilanyl-ethoxymethyl)-1H-imidazole-2-carboxylic acid [2-cyclohex-1-enyl-4-(1-methoxy-piperidin-4-yl)-phenyl]-amide

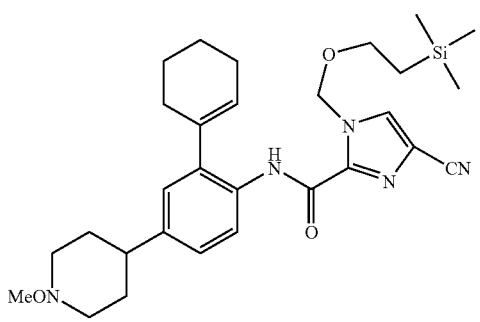

A mixture of 4-cyano-1-(2-trimethylsilanyl-ethoxymethyl)-1H-imidazole-2-carboxylic acid, potassium salt (as prepared in Example 3, step (d), 35.6 mg, 0.100 mmol), DIEA (0.34 μL, 0.20 mmol), 2-cyclohex-1-enyl-4-(1-methoxy-piperidin-4-yl)-phenylamine (as prepared in previous step, 28.6 mg, 0.1 mmol) and PyBroP (69.9 mg, 0.150 mmol) in DCM (2 mL) was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo The product was chromatographed on silica (20-40% EtOAc/hexane) to obtain the title compound (26 mg, 48%). Mass spectrum (ESI, m/z): Calcd. for C$_{29}$H$_{41}$N$_5$O$_3$Si, 536.3 (M+H), found 536.2.

d) 5-Cyano-1H-imidazole-2-carboxylic acid [2-cyclohex-1-enyl-4-(1-methoxy-piperidin-4-yl)-phenyl]-amide trifluoroacetic acid salt

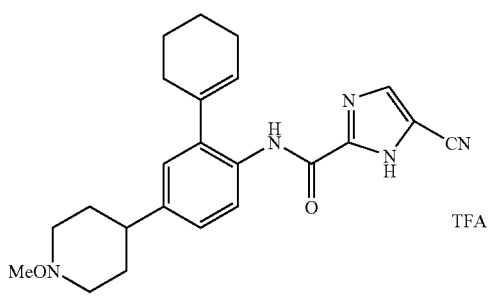

To a solution of 4-cyano-1-(2-trimethylsilanyl-ethoxymethyl)-1H-imidazole-2-carboxylic acid [2-cyclohex-1-enyl-4-(1-methoxy-piperidin-4-yl)-phenyl]-amide (as prepared in previous step, 31 mg, 0.020 mmol) in DCM (0.5 mL) and EtOH (11 μL) was added TFA (0.1 mL). The resulting solution was stirred at RT for 6 h. The reaction mixture was concentrated in vacuo and the resulting residue was dried for 1 h, suspended in ether (10 mL) and sonicated for 5 min. The solid formed was collected by suction filtration to obtain the title compound (17.3 mg, 58%). 1H-NMR (DMSO; 400 MHz): δ 9.70 (s, 1H), 8.30 (s, 1H), 7.83 (d, 1H, J=8.4 Hz), 7.14 (d, 1H, J=8.4 Hz), 7.05 (s, 1H), 5.71 (br s, 1H), 3.30-3.55 (m, 5H), 2.41-2.62 (m, 2H), 2.12-2.19 (m, 4H), 1.60-1.85 (m, 8H). Mass spectrum (ESI, m/z): Calcd. for C$_{23}$H$_{27}$N$_5$O$_2$, 406.2 (M+H), found 406.1.

EXAMPLE 54

4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt

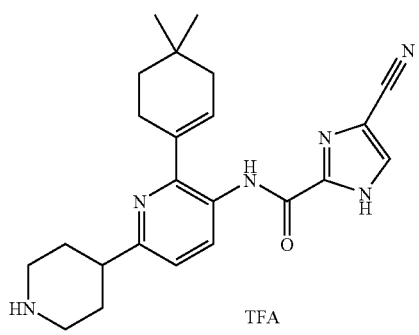

a) 5-Nitro-3',6'-dihydro-2'H-[2,4']bipyridinyl-1'-carboxylic acid tert-butyl ester

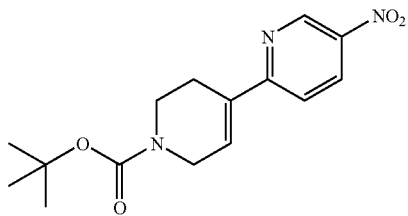

A solution of 202 mg (0.994 mmol) 2-bromo-5-nitropyridine in 4 mL of toluene and 2 mL of EtOH was treated with 338 mg (1.09 mmol) 4-trifluoromethane-sulfonyloxy-3,6-dihydro-2H-pyridine-1-carboxylic acid tert-butyl ester (*Synthesis*, 993, (1991)) and 1.49 mL (2.981 mmol) 2 M aqueous $Na_2CO_3$. The mixture was degassed via sonication, placed under argon, treated with 80.3 mg (0.00700 mmol) $Pd(PPh_3)_4$ and heated to 80° C. for 4 h. The mixture was diluted with EtOAc and washed with water. The organic layer was dried over $MgSO_4$ and concentrated in vacuo. The resulting residue was chromatographed on a 50-g silica Varian MegaBond Elut column with 10-25% EtOAc-hexane to afford 226 mg (75%) of the title compound as a light yellow solid: Mass spectrum (ESI, m/z): Calcd. for $C_{15}H_{19}N_3O_4$, 306.1 (M+H), found 305.7.

b) 5-Amino-3',4',5',6'-tetrahydro-2'H-[2,4']bipyridinyl-1'-carboxylic acid tert-butyl ester

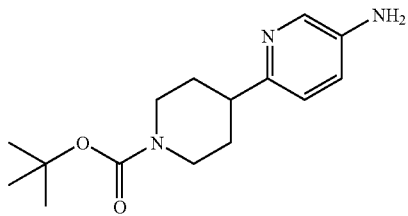

A solution of 226 mg (0.740 mmol) 5-nitro-3',6'-dihydro-2'H-[2,4']bipyridinyl-1'-carboxylic acid tert-butyl ester (as prepared in the previous step) in 15 mL MeOH was treated with 110 mg 10% Pd/C (Degussa type E101-NE/W, Aldrich, 50% by weight water) and 1 atm $H_2$ at room temperature for 18 h. The mixture was filtered through Celite, and the filter cake was washed with MeOH. Concentration afforded 220 mg (107%) of the title compound as a colorless glassy solid. Mass spectrum (ESI, m/z): Calcd. for $C_{15}H_{23}N_3O_2$, 278.2 (M+H), found 278.0.

c) 5-Amino-6-bromo-3',4',5',6'-tetrahydro-2'H-[2,4']bipyridinyl-1'-carboxlic acid tert-butyl ester

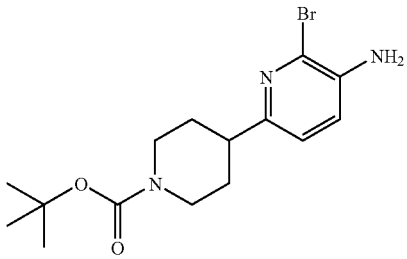

A solution of 220 mg (0.793 mmol) 5-amino-3',4',5',6'-tetrahydro-2'H-[2,4']bipyridinyl-1'-carboxylic acid tert-butyl ester (as prepared in the previous step) in 10 mL $CH_2Cl_2$ was treated with 134 mg (0.753 mmol) N-bromosuccinimide at room temperature for 20 min. The mixture was diluted with $CH_2Cl_2$ and washed with saturated aqueous $NaHCO_3$. The organic layer was dried over $MgSO_4$ and concentrated in vacuo. Chromatography of the residue on a 50-g silica Varian MegaBond Elut column with 10-35% EtOAc-hexanes afforded 209 mg (74%) of the title compound as a colorless gliassy solid. $^1$H-NMR ($CDCl_3$; 400 MHz): δ 6.97 (d, 1H, J=8.0 Hz), 6.91 (d, 1H, J=8.0 Hz), 4.28-4.15 (br s, 2H), 4.06-3.90 (m, 2H), 2.85-2.75 (m, 2H), 2.77-2.68 (m, 1H), 192-1.83 (m, 2H), 1.68-1.54 (m, 2H), 1.47 (s, 9H).

d) 5-Amino-6-(4,4-dimethyl-cyclohex-1-enyl)-3',4',5',6'-tetrahydro-2'H-[2,4']bipyridinyl-1'-carboxylic acid tert-butyl ester

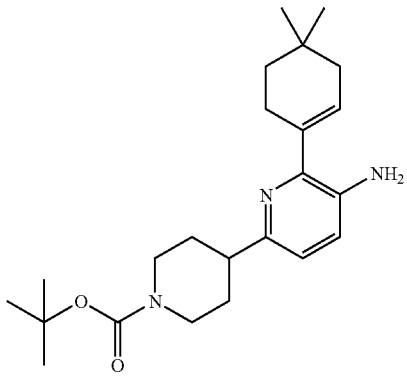

A solution of 209 mg (0.587 mmol) 5-amino-6-bromo-3',4',5',6'-tetrahydro-2'H-[2,4']bipyridinyl-1'-carboxylic acid tert-butyl ester (as prepared in the previous step) in 5 mL of toluene and 2.5 mL of EtOH was treated with 99.3 mg (0.645 mmol) 4,4-dicyclohex-1-enylboronic acid and 2.34 mL (4.69 mmol) 2 M aqueous $Na_2CO_3$. The mixture was degassed via sonication, placed under argon, treated with 47.4 mg (0.0410 mmol) $Pd(PPh_3)_4$, and heated to 80° C. for 16 h. The mixture was diluted with EtOAc and washed with water. The aqueous layer was extracted with additional EtOAc, and the combined organic layers were dried over $MgSO_4$ and concentrated in vacuo. Chromatography of the residue on a 50-g silica Varian MegaBond Elut column with 25% EtOAc-hexanes afforded 150 mg (66%) of the title compound as a white foamy solid. Mass spectrum (ESI, m/z): Calcd. for $C_{23}H_{35}N_3O_2$, 386.3 (M+H), found 386.3.

e) 5-{[4-Cyano-1-(2-trimethylsilanyl-ethoxymethyl)-1H-imidazole-2-carbonyl]-amino}-6-(4,4-dimethyl-cyclohex-1-enyl)-3',4',5',6'-tetrahydro-2'H-[2,4']bipyridinyl-1'-carboxylic acid tert-butyl ester

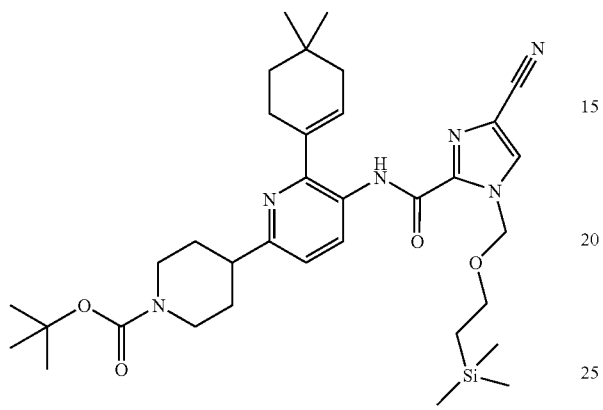

A solution of 150 mg (0.389 mmol) 5-amino-6-(4,4-dimethyl-cyclohex-1-enyl)-3',4',5',6'-tetrahydro-2'H-[2,4']bipyridinyl-1'-carboxylic acid tert-butyl ester (as prepared in the previous step) in 15 mL of $CH_2Cl_2$ was treated with 131 mg (0.428 mmol) of 4-cyano-1-(2-trimethylsilanyl-ethoxymethyl)-1H-imidazole-2-carboxylate potassium salt (as prepared in Example 3, step (b)), 272 mg (0.584 mmol) PyBroP, and 203 µL (1.17 mmol) DIEA at room temperature for 3 h. The mixture was diluted with $CH_2Cl_2$ and washed with saturated aqueous $NaHCO_3$. The organic layer was dried over $MgSO_4$ and concentrated in vacuo. Chromatography of the residue on a 50-g silica Varian MegaBond Elut column with 50% EtOAc-hexanes afforded 215 mg (87%) of the title compound as a white solid. Mass spectrum (ESI, m/z): Calcd. for $C_{34}H_{50}N_6O_4Si$, 635.4 (M+H), found 635.3.

f) 4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt

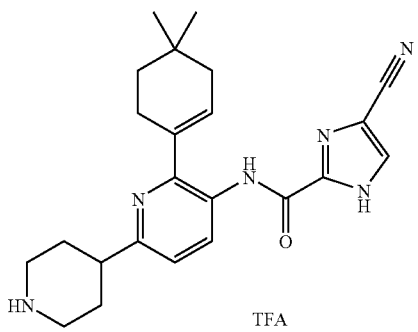

A solution of 215 mg (0.339 mmol) 5-{[4-cyano-1-(2-trimethylsilanyl-ethoxymethyl)-1H-imidazole-2-carbonyl]-amino}-6-(4,4-dimethyl-cyclohex-1-enyl)-3',4',5',6'-tetrahydro-2'H-[2,4']bipyridinyl-1'-carboxylic acid tert-butyl ester (as prepared in the previous step) in 10 mL of $CH_2Cl_2$ was treated with three drops MeOH and 3 mL TFA at room temperature for 4 h. MeOH (10 mL) was added and the solvents evaporated in vacuo. Chromatography of the residue on a 50-g silica Varian MegaBond Elut column with 10% MeOH—$CH_2Cl_2$ afforded 210 mg (97%) of the title compound as a white solid.

$^1$H-NMR ($CD_3OD$; 400 MHz): δ 8.59 (d, 1H, J=8.4 Hz), 8.04 (s, 1H), 7.28 (d, 1H, J=8.4 Hz), 6.02-5.93 (m, 1H), 3.58-3.48 (m, 2H), 3.32-3.03 (m, 3H), 2.54-2.42 (m, 2H), 2.23-2.02 (m, 6H), 1.11 (s, 6H). Mass spectrum (ESI, m/z): Calcd. for $C_{23}H_{28}N_6O$, 405.2 (M+H), found 405.2.

EXAMPLE 55

4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4']bipyridinyl-5-yl]-amide trifluoroacetic acid salt

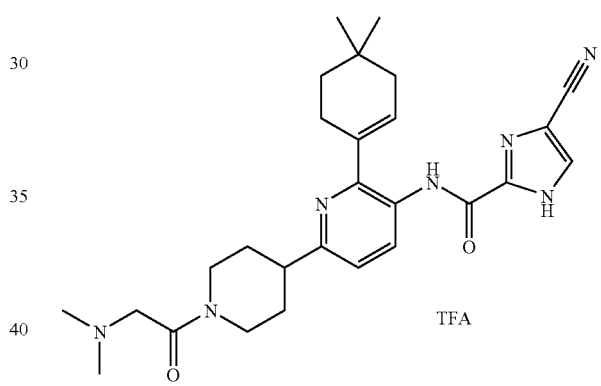

A suspension of 20.9 mg (0.203 mmol) N,N-dimethylglycine in 4 mL $CH_2Cl_2$ was treated with 49.8 mg (0.197 mmol) bis(2-oxo-3-oxazolidinyl)phosphinic chloride (BOP—Cl) and 75 µL (0.54 mmol) $Et_3N$ at room temperature for 1 h. The mixture was then treated with 70.0 mg (0.135 mmol) 4-cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetate (as prepared in Example 54, step (f)) at room temperature for 18 h. The mixture was diluted with $CH_2Cl_2$ and washed with water. The organic layer was dried over $MgSO_4$ and concentrated in vacuo. The residue was purified by RP-HPLC (C1 8) with 10-80% $CH_3CN$ in 0.1% TFA/$H_2O$ over 30 min to afford 34.9 mg (53%) of the title compound as a white solid. $^1$H-NMR ($CD_3OD$; 400 MHz): δ 8.38 (d, 1H, J=8.4 Hz), 8.05 (s, 1H), 7.33 (d, 1H, J=8.4 Hz), 6.05-5.98 (m, 1H), 4.68 (d, 1H, J=15.2 Hz), 3.82 (d, 1H, J=15.2 Hz) 3.16-3.05 (m, 1H), 3.01-2.94 (m, 6H), 2.52-2.40 (m, 2H), 2.39 (s, 6H), 2.10 (m, 2H), 2.09-1.87 (m, 2H), 1.67-1.59 (m, 2H), 1.12 (s, 6H). Mass spectrum (ESI, m/z): Calcd. for $C_{27}H_{35}N_7O_2$, 490.3 (M+H), found 490.4.

EXAMPLE 56

4-Cyano-1H-imidazole-2-carboxylic acid [6-(4,4-dimethyl-cyclohex-1-enyl)-1'-(2-methanesulfonyl-ethyl)-1',2',3',4',5',6'-hexahydro-[2,4']bipyridinyl-5-yl]-amide trifluoroacetic acid salt

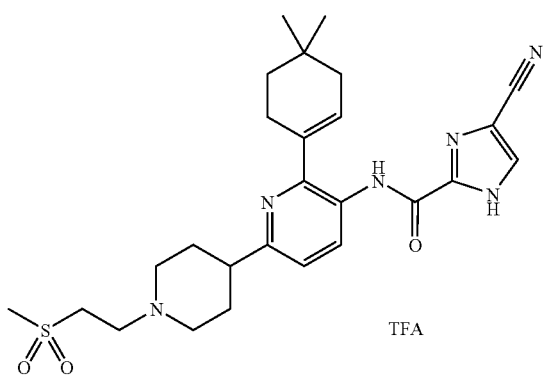

TFA

A solution of 70.0 mg (0.135 mmol) 4-cyano-1H-imidazole-2-carboxylic acid [6-(4,4-dimethyl-cyclohex-1-enyl)-1',2',3',4',5',6'-hexahydro-[2,4']bipyridinyl-5-yl]-amide (as prepared in Example 54, step (f)) in 10 mL of $CH_2Cl_2$ was treated with 32.7 mg (0.162 mmol) methanesulfonic acid 2-methanesulfonyl-ethyl ester (as prepared in Example 40, step (a)) and 70.5 µL (0.405 mmol) DIEA at room temperature for 6 h. The mixture was diluted with $CH_2Cl_2$ and washed with water. The organic layer was dried over $MgSO_4$ and concentrated in vacuo. The residue was purified by RP-HPLC (C 18) with 20-60% $CH_3CN$ in 0.1% $TFA/H_2O$ over 30 min to afford 48 mg (85%) of the title compound as a white solid. H-NMR ($CD_3OD$; 400 MHz): δ 8.65 (d, 1H, J=8.4 Hz), 8.05 (s, 1H), 7.34 (d, 1H, J=8.4 Hz), 6.05-5.98 (m, 1H), 3.85-3.66 (m, 6H), 3.29-3.21 (m, 2H), 3.20-3.01 (m, 1H), 3.14 (s, 3H), 2.53-2.45 (m, 2H), 2.30-2.15 (m, 4H), 2.15-2.10 (m, 2H), 1.62 (t, 2H, J=6.4 Hz), 1.11 (s, 6H). Mass spectrum (ESI, m/z): Calcd. for $C_{26}H_{34}N_6O_3S$, 511.2 (M+H), found 511.3.

EXAMPLE 57

5-Cyano-1H-imidazole-2-carboxylic acid (4-[1-(2-amino-2-methyl-propionyl)-piperidin-4-yl]-2-cyclohex-1-enyl-phenyl)-amide trifluoroacetic acid salt

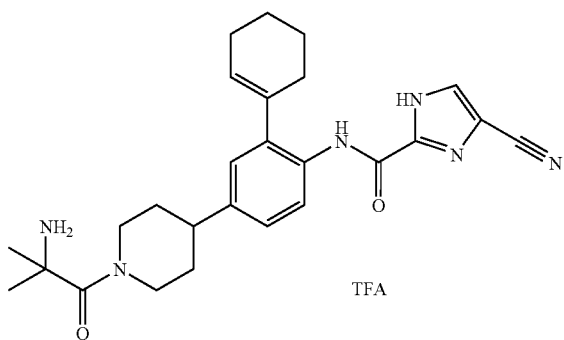

TFA a) {2-[4(4-{[4-Cyano-1-(2-trimethylsilanyl-ethoxymethyl)-1H-imidazole-2-carbonyl]-amino}-3-cyclohex-1-enyl-phenyl)-piperidin-1-yl]-1,1-dimethyl-2-oxo-ethyl}-carbamic acid tert-butyl ester

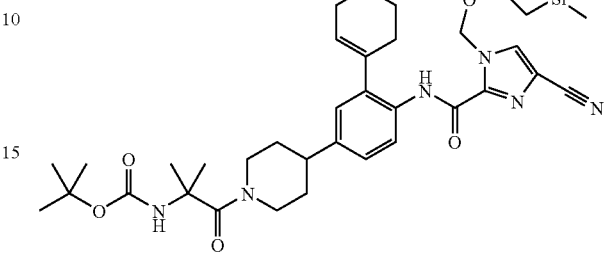

To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (231 mg, 0.380 mmol) (as prepared in Example 14, step (a)) in 2.5 mL of DCM and 0.4 mL EtOH was added 700 µL of TFA and the solution stirred for 3 h at 25° C. The reaction was diluted with 4 mL of EtOH and then concentrated to give ca. a 2:1 mixture of 5-cyano-1-(2-trimethylsilanyl-ethoxymethyl)-1H-imidazole-2-carboxylic acid (2-cyclohex-1-enyl-4-piperidin-4-yl-phenyl)-amide trifluoroacetic acid salt to starting material by $^1$H-NMR and LC/MS which was used in the following step without further purification. The mixture in 3 mL of DCM was added to a solution of 2-tert-butoxycarbonylamino-2-methyl-propionic acid (53 mg, 0.70 mmol), DIEA (122 µL, 0.700 mmol) and PyBroP (144 mg, 0.300 mmol) in 3 mL of DCM and the reaction was stirred at 25° C. overnight. The reaction was diluted with EtOAc (25 mL) and washed with satd aq $NaHCO_3$ (1×25 mL) and brine (25 mL) and the organic layer was dried over $Na_2SO_4$ and then concentrated. Purification of the residue by preparative TLC (50% EtOAc-hexanes) afforded 40 mg (15%) of the title compound as a white solid. Mass Spectrum (ESI, m/z): Calcd. for $C_{37}H_{55}N_6O_5Si$, 691.3 (M+H), found 691.1.

b) 5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt To a solution of {2-[4-(4-{[4-cyano-1-(2-trimethylsilanyl-ethoxymethyl)-1H-imidazole-2-carbonyl]-amino}-3-cyclohex-1-enyl-phenyl)-piperidin-1-yl]-1,1-dimethyl-2-oxo-ethyl}-carbamic acid tert-butyl ester (40 mg, 0.050 mmol) in 2 mL of DCM and 20 µL of EtOH was added 1.5 mL of TFA. The solution was stirred for 3 h at 25° C., diluted with 2 mL of EtOH and concentrated in vacuo. Trituration of the residue with ether afforded 8.4 mg (29%) of the title compound as a white solid. $^1$H-NMR ($CD_3OD$; 400 MHz): δ 8.10 (d, 1H, J=8.4 Hz), 8.00 (s, 1H), 7.16 (d, 1H, J=8.4 Hz), 7.07 (s, 1H), 5.79 (s, 1H), 4.55-4.48 (m, 1H), 3.30 (s, 6H), 2.89-2.87 (m, 2H), 2.40-2.25 (m, 4H), 1.96-1.93 (m, 2H), 1.86-1.83 (m, 6H), 1.64-1.61 (m, 2H). Mass Spectrum (ESI, m/z): Calcd. for $C_{26}H_{33}N_6O_2$, 461.2 (M+H), found 461.3.

EXAMPLE 58

5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide

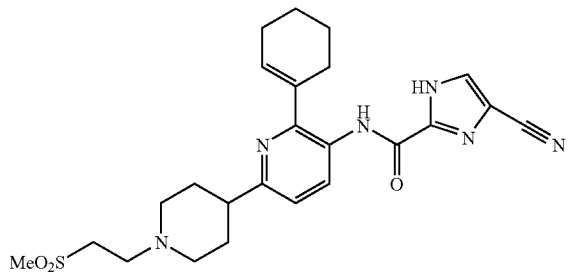

a) 5-Amino-6-cyclohex-1-enyl-3',4',5',6'-tetrahydro-2'H-[2,4']bipyridinyl-1'-carboxylic acid tert-butyl ester

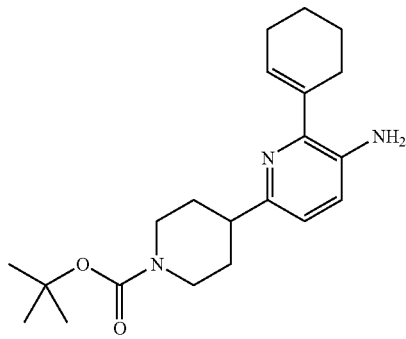

To a mixture of 5-amino-6-bromo-3',4',5',6'-tetrahydro-2'H-[2,4']bipyridinyl-1'-carboxylic acid tert-butyl ester (331 mg, 0.93 mmol) (as prepared in Example 54, step (c)) and cyclohexen-1-yl boronic acid (141 mg, 1.11 mmol) in 5 mL of EtOH, 10 mL of toluene and 5 mL of 2 M $Na_2CO_3$, was added $Pd(PPh_3)_4$ (107 mg, 0.0930 mmol) and the result was heated at 80° C. for 16 h. The reaction was diluted with 100 mL of ether and 100 mL of brine and the layers were separated. The organic layer was dried ($Na_2SO_4$) and concentrated in vacuo. Purification of the residue by column chromatography (silica gel, 30-60% ether-hexanes) afforded 248 mg (74%) the title compound as an light brown oil LC-MS (ESI, m/z): Calcd. for $C_{21}H_{32}N_3O_2$ (M+H), 358.2, found 358.1.

b) 5-{[4-Cyano-1-(2-trimethylsilanyl-ethoxymethyl)-1H-imidazole-2-carbonyl]-amino}-6-cyclohex-1-enyl-3',4',5',6'-tetrahydro-2'H-[2,4']bipyridinyl-1'-carboxylic acid tert-butyl ester

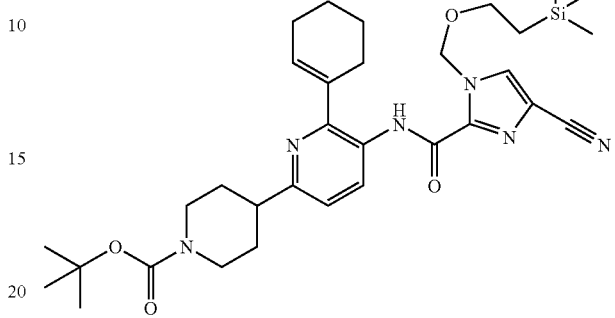

To a solution of 4-cyano-1-(2-trimethylsilanyl-ethoxymethyl)-1H-imidazole-2-carboxylate potassium salt (296 mg, 0.970 mmol) (as prepared in Example 3, step (d)) in 8 mL DCM was added DIEA (291 µL, 1.72 mmol) and PyBroP (512 mg, 1.10 mmol), and the reaction was stirred at 25° C. for 15 min. A solution of 5-amino-6-cyclohex-1-enyl-3',4',5',6'-tetrahydro-2'H-[2,4']bipyridinyl-1'-carboxylic acid tert-butyl ester (233 mg, 0.65 mmol) (as prepared in the previous step) in 4 mL DCM was added and the reaction stirred overnight at 25° C. The reaction was diluted with EtOAc (25 mL) and washed with $NaHCO_3$ (1×25 mL) and brine (25 mL) and the organic layer was dried over $Na_2SO_4$ and then concentrated. The residue was purified by flash chomatography (silica gel, 5% MeOH-$CHCl_3$) to afford 167 mg (40%) of the title compound as a white solid. Mass Spectrum (ESI, m/z): Calcd. for $C_{32}H_{46}N_6O_4Si$, 607.3 (M+H), found 607.3.

c) 5-Cyano-1H-imidazole-2-carboxylic acid (6-cyclohex-1-enyl-1',2',3',4',5',6'-hexahydro-[2,4']bipyridinyl-5-yl)-amide trifluoroacetic acid salt

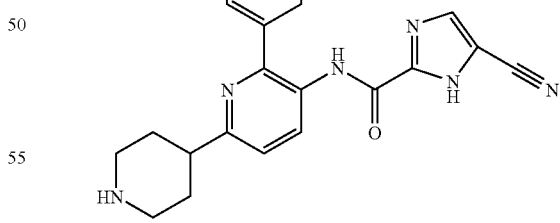

The title compound was prepared from 5-{[4-cyano-1-(2-trimethylsilanyl-ethoxymethyl)-1H-imidazole-2-carbonyl]-amino}-6-cyclohex-1-enyl-1',2',3',4',5',6'-tetrahydro-2'H-[2,4']bipyridinyl-1'-carboxylic acid tert-butyl ester (167 mg, 0.27 mmol) using a procedure similar to Example 14, step (b) to afford 57 mg (43%) of the title compound as a white solid. LC-MS (ESI, m/z): Calcd. for $C_{21}H_{24}N_6O$, 377.2 (M+H), found 377.2.

d) 5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide To a slurry of 5-cyano-1H-imidazole-2-carboxylic acid (6-cyclohex-1-enyl-1',2',3',4',5',6'-hexahydro-[2,4']bipyridinyl-5-yl)-amide trifluoroacetic acid salt (57 mg, 0.11 mmol) in 5 mL of DCM was added DIEA (50.4 µL, 0.290 mmol) followed by 30.5 mg (0.150 mmol) of methanesulfonic acid 2-methanesulfonyl-ethyl ester (as prepared in Example 40, step(a)). The reaction was allowed to stir overnight, diluted with 20 mL of DCM, washed with satd aq NaHCO$_3$ (1×20 mL) and dried over Na$_2$SO$_4$. Purification by preparative TLC (silica gel, 40% EtOAc-hexanes) afforded 22.3 mg (40%) of the title compound as a white solid. $^1$H-NMR (DMSO; 400 MHz): δ 10.02 (s, 1H), 8.24 (s, 1H), 8.11 (d, 1H, J=8.4 Hz), 7.18 (d, 1H, J=8.4 Hz), 5.96 (s, 1H), 3.04 (s, 3H), 3.02-2.99 (m, 3H), 2.73 (t, 2H, J=2.7 Hz), 2.39-2.37 (m, 2H), 2.11-2.05 (m, 4H), 1.85-1.64 (m, 10H). Mass Spectrum (ESI, m/z): Calcd. for C$_{24}$H$_{31}$N$_6$O$_3$S, 483.2 (M+H), found 483.3.

EXAMPLE 59

An alternate method for the synthesis of the intermediate described in Example 3 is described below.

4-Cyano-1-(2-trimethylsilanyl-ethoxymethyl)-1H-imidazole-2-carboxylic acid potassium salt

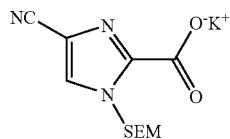

a) 1H-Imidazole-4-carbonitrile

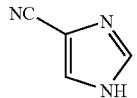

A 22-L, four-neck, round-bottom flask equipped with a mechanical stirrer, a temperature probe, a condenser, and an addition funnel with a nitrogen inlet was charged with 1H-imidazole-4-carboxaldehyde (Aldrich, 1.10 kg, 11.5 mol) and pyridine (3.0 L, 3.0 mol). The reaction flask was cooled to 8° C. with an ice bath and hydroxylamine hydrochloride (871 g, 12.5 mol) was added slowly in portions to maintain the internal temperature below 30° C. The reaction was allowed to cool to ambient temperature and stirred for 2 h at ambient temperature. The resulting thick yellow solution was heated to 80° C. with a heating mantle and acetic anhydride (2.04 L, 21.6 mol) was added dropwise over 200 min to maintain the temperature below 110° C. during the addition. The reaction mixture was heated at 100° C. for 30 min, after which time it was allowed to cool to ambient temperature and then further cooled in an ice bath. The pH was adjusted to 8.0 (pH meter) by the addition of 25 wt % NaOH (5.5 L) at such a rate that the internal temperature was maintained below 30° C. The reaction mixture was then transferred into a 22-L separatory funnel and extracted with ethyl acetate (6.0 L). The combined organic layer was washed with brine (2×4.0 L), dried over MgSO$_4$, filtered, and concentrated to dryness under reduced pressure at 35° C. to give the crude product as a yellow semisolid. The resulting semisolid was suspended in toluene (3.0 L) and stirred for 1 h, after which time it was filtered to give a light yellow solid, which was resuspended in toluene (3.0 L) and stirred for 1 h. The resulting slurry was filtered and the filter cake washed with toluene (2×500 mL) to give the title compound as a light yellow solid [870 g, 82%). The $^1$H and $^{13}$C NMR spectra were consistent with the assigned structure.

b) 1-(2-Trimethylsilanyl-ethoxymethyl)-1H-imidazole-4-carbonitrile and 3-(2-trimethylsilanyl-ethoxymethyl)-3H-imidazole-4-carbonitrile

A 22-L, four-neck, round-bottom flask equipped with a mechanical stirrer, a temperature probe, and an addition funnel with a nitrogen inlet was charged with 1H-imidazole-4-carbonitrile (830 g, 8.91 mol, as prepared in the previous step), potassium carbonate (2.47 kg, 17.8 mol), and acetone (6.0 L). Agitation was initiated and the mixture was cooled to 10° C. with an ice bath. SEMCl (1.50 kg, 9.00 mol) was added through the addition funnel over 210 min to maintain the internal temperature below 15° C. The reaction was then allowed to warm to ambient temperature and stirred at ambient temperature overnight (20 h). The reaction mixture was then cooled in an ice bath to 10° C. and quenched by the slow addition of water (8.0 L) over 30 min to maintain the internal temperature below 30° C. The resulting mixture was transferred to a 22-L separatory funnel and extracted with ethyl acetate (2×7.0 L). The combined organics were concentrated under reduced pressure at 35° C. to give the crude product as a dark brown oil, which was purified through a plug of silica gel (16.5×20 cm, 2.4 kg silica gel) using 2:1 heptane/ethyl acetate (15 L) as eluent. The fractions containing the product were combined and concentrated under reduced pressure at 35° C. to afford a mixture of the title compounds as a light brown oil [1785 g, 90%). The $^1$H NMR spectrum was consistent with the assigned structure and indicated the presence of a 64:36 ratio of regioisomers.

c) 2-Bromo-1-(2-trimethylsilanyl-ethoxymethyl)-1H-imidazole-4carbonitrile

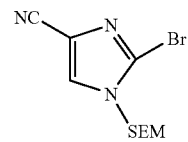

A 22-L, four-neck, round-bottom flask equipped with a mechanical stirrer, a temperature probe, and a condenser with a nitrogen inlet was charged with a mixture of 1-(2-trimethylsilanyl-ethoxymethyl)-1H-imidazole-4-carbonitrile and 3-(2-trimethylsilanyl-ethoxymethyl)-3H-imidazole-4-carbonitrile [600 g, 2.69 mol, as prepared in the previous step) and carbon tetrachloride (1.8 L). Agitation was initiated and the mixture was heated to 60° C. At this point N-bromosuccinimide (502 g, 2.82 mol) was added in several portions over 30 min, which resulted in an exotherm to 74° C. The reaction was allowed to cool to 60° C. and further stirred at 60° C. for 1 h. The reaction was allowed to cool slowly to ambient temperature and the resulting slurry was filtered and the filtrate washed with satd NaHCO$_3$ solution (4.0 L). The organics were passed through a plug of silica gel (8×15 cm, silica gel; 600 g) using 2:1 heptane/ethyl acetate (6.0 L) as eluent. The fractions containing the product (based on TLC analysis) were combined and concentrated under reduced pressure to give a crystalline light yellow solid, which was then filtered and washed with heptane (500 mL) to give the title compound as a crystalline white solid [593 g, 73%). The $^1$H and $^{13}$C NMR spectra were consistent with the assigned structure and showed no evidence of the minor regioisomer.

d) 4-Cyano-1-(2-trimethylsilanyl-ethoxymethyl)-1H-imidazole-2-carboxylic acid ethyl ester

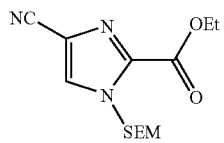

A 12-L, four-neck, round-bottom flask equipped with a mechanical stirrer, a temperature probe, and an addition funnel with a nitrogen inlet was charged with 2-bromo-1-(2-trimethylsilanyl-ethoxymethyl)-1H-imidazole-4-carbonitrile [390 g, 1.29 mol, as prepared in the previous step) and anhydrous tetrahydrofuran (4.0 L). Agitation was initiated and the reaction mixture was cooled to −50° C. using a dry ice/acetone bath. Isopropylmagnesium chloride (2.0 M in THF, 760 mL, 1.52 mol) was added through the addition funnel over 30 min to maintain the internal temperature below −40° C. The reaction was stirred for a further 30 min at −43° C., after which time it was cooled to −78° C. Ethyl chloroformate (210 mL, 2.20 mol) was added through the addition funnel over 10 min to maintain the internal temperature below −60° C. The reaction was stirred for a further 40 min at −70° C., at which point the dry ice/acetone bath was removed and the reaction was allowed to warm to ambient temperature over 1.5 h. The reaction mixture was cooled in an ice bath to 0° C. and quenched by the slow addition of satd ammonium chloride solution (1.8 L) at such a rate that the internal temperature was maintained below 10° C. The reaction mixture was transferred into a 12-L separatory funnel, diluted with ethyl acetate (4.0 L), and the layers were separated. The organic layer was washed with brine (2×2.0 L) and concentrated under reduced pressure at 35° C. to give a brown oil. The crude oil was dissolved in dichloromethane (300 mL) and purified by chromatography (15×22 cm, 1.5 kg of silica gel, 10:1 to 4:1 heptane/ethyl acetate) to give a yellow oil, which was dissolved in EtOAc (100 mL), diluted with heptane (2.0 L), and stored in a refrigerator for 5 h. The resulting slurry was filtered to give the title compound as a crystalline white solid (141 g, 37%). The $^1$H and $^{13}$C NMR spectra were consistent with the assigned structure.

e) 4-Cyano-1-(2-trimethylsilanyl-ethoxymethyl)-1H-imidazole-2-carboxylic acid potassium salt

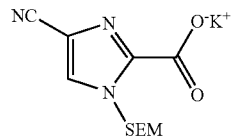

A 5-L, three-neck, round-bottom flask equipped with a mechanical stirrer, a temperature probe, and an addition funnel with a nitrogen inlet was charged with 5 [400 g, 1.35 mol) and ethanol (4.0 L). Agitation was initiated and a water bath was applied after all of the solid had dissolved. A solution of 6 N KOH (214.0 mL, 1.29 mol) was added through the addition funnel over 15 min to maintain the internal temperature below 25° C. and the reaction was stirred for 5 min at room temperature. The solution was then concentrated to dryness under reduced pressure at 20° C. to give a white solid. The resulting solid was suspended in methyl t-butyl ether (MTBE, 4.0 L) and stirred for 30 min, after which time the slurry was filtered and the filter cake washed with MTBE (1.0 L) to give the title compound as a white solid, which was further dried under vacuum at ambient temperature for 4 d [366 g, 89%). The $^1$H NMR, $^{13}$C NMR, and mass spectra were consistent with the assigned structure. Anal. Calcd for $C_{11}H_{16}KN_3O_3Si$: C, 43.25; H, 5.28; N, 13.76. Found: C, 42.77; H, 5.15; N, 13.37. Karl Fisher: 1.3% $H_2O$.

EXAMPLE 60

5-Cyano-1H-imidazole-2-carboxylic acid [4-(3,6-dihydro-2H-pyran-4-yl)-2-(4,4-dimethyl-cyclohex-1-enyl)-phenyl]-amide

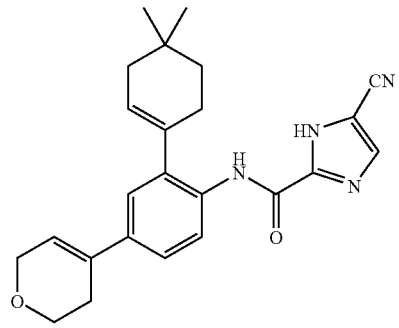

a) 1-(2-Trimethylsilanyl-ethoxymethyl)-1H-imidazole-4-carbonitrile

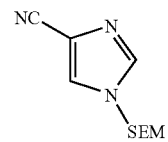

A flask charged with imidazole-4-carbonitrile (0.5 g, 5.2 mmol) (Synthesis, 677, 2003), 2-(trimethylsilyl)ethoxymethyl chloride (SEMCl) (0.95 mL, 5.3 mmol), K$_2$CO$_3$ (1.40 g, 10.4 mmol), and acetone (5 mL) was stirred for 10 h at RT. The mixture was diluted with EtOAc (20 mL) and washed with water (20 mL) and brine (20 mL) and the organic layer dried over MgSO$_4$. The crude product was eluted from a 20-g SPE cartridge (silica) with 30% EtOAc/hexane to give 0.80 g (70%) of the title compound as a colorless oil: Mass spectrum (CI(CH$_4$), m/z) Calcd. for C$_{10}$H$_{17}$N$_3$OSi, 224.1 (M+H), found 224.1.

b) 2-Bromo-1-(2-trimethylsilanyl-ethoxymethyl)-1H-imidazole-4carbonitrile

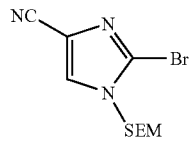

To a solution of 1-(2-trimethylsilanyl-ethoxymethyl)-1H-imidazole-4-carbonitrile (0.70 g, 3.1 mmol) (as prepared in the previous step) in CCl$_4$ (10 mL) was added NBS (0.61 g, 3.4 mmol) and AIBN (cat), and the mixture heated at 60° C. for 4 h. The reaction was diluted with EtOAc (30 mL) and washed with NaHCO$_3$ (2×30 mL) and brine (30 mL) and the organic layer was dried over Na$_2$SO$_4$ and then concentrated. The title compound was eluted from a 20-g SPE cartridge (silica) with 30% EtOAc/hexane to give 0.73 g (77%) of a yellow solid: Mass spectrum (CI(CH$_4$), m/z) Calcd. for C$_{10}$H$_{16}$BrN$_3$OSi, 302.0/304.0 (M+H), found 302.1/304.1.

c) 4-Cyano-1-(2-trimethylsilanyl-ethoxymethyl)-1H-imidazole-2-carboxylic acid ethyl ester

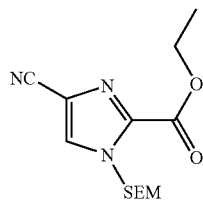

To a solution of 2-bromo-1-(2-trimethylsilanyl-ethoxymethyl)-1H-imidazole-4-carbonitrile (0.55 g, 1.8 mmol) (as prepared in the previous step) in THF (6 mL) at −40° C. was added drop wise a solution of 2M i-PrMgCl in THF (1 mL). The reaction was allowed to stir for 10 min at −40° C. and then cooled to −78° C., and ethyl cyanoformate (0.3 g, 3.0 mmol) was added. The reaction allowed to attain RT and stirred for 1 h. The reaction was quenched with satd aq NH4Cl, diluted with EtOAc (20 mL) and washed with brine (2×20 mL), and the organic layer was dried over Na$_2$SO$_4$ and then concentrated. The title compound was eluted from a 20-g SPE cartridge (silica) with 30% EtOAc/hexane to give 0.4 g (74%) of a colorless oil: Mass spectrum (ESI, m/z): Calcd. for C$_{13}$H$_{21}$N$_3$O$_3$Si, 296.1 (M+H), found 296.1.

d) 4-Cyano-1-(2-trimethylsilanyl-ethoxymethyl)-1H-imidazole-2-carboxylate potassium salt

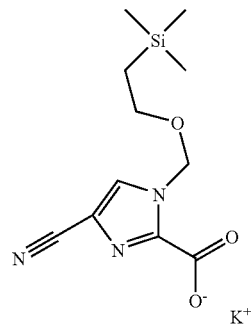

To a solution of 4-cyano-1-(2-trimethylsilanyl-ethoxymethyl)-1H-imidazole-2-carboxylic acid ethyl ester (0.4 g, 1.3 mmol) (as prepared in the previous step) in ethanol (3 mL) was added a solution of 6M KOH (0.2 mL) and the reaction was stirred for 10 min and then concentrated to give 0.40 g (100%) of the title compound as a yellow solid: 1H-NMR (400 MHz, CD$_3$OD) δ 7.98 (s, 1H), 5.92 (s, 2H), 3.62 (m, 2H), 0.94 (m, 2H), 0.00 (s, 9H). Mass spectrum (ESI-neg, m/z) Calcd. for C$_{11}$H$_{16}$N$_3$KO$_3$Si, 266.1 (M−K), found 266.0.

e) 4-Bromo-2-(4,4-dimethyl-cyclohex-1-enyl)-phenylamine

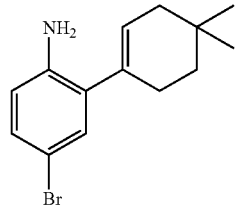

A flask is charged with 4-bromo-2-iodo-phenylamine (1.10 g, 3.70 mmol), 4,4-dimethylcyclohexen-1-ylboronic acid (0.630 g, 4.07 mmol), Pd(PPh$_3$)$_4$ (0.240 g, 5 mol %), 2 M Na$_2$CO$_3$ (16 mL), EtOH (16 mL) and toluene (32 mL) and heated at 80° C. for 6 h. The reaction was diluted with EtOAc (100 mL) and washed with saturated aqueous NaHCO$_3$ (2×100 mL) and brine (100 mL), and the organic layer dried over Na$_2$SO$_4$ and evaporated. The crude product was purified by flash silica gel chromatography eluting with 10% EtOAc/hexane to give 0.68 g (66%) of the title compound as a light yellow oil: Mass spectrum (ESI, m/z) calcd. for C$_{14}$H$_{18}$BrN, 280.1 (M+H), found 280.1.

f) 4-Cyano-1-(2-trimethylsilanyl-ethoxymethyl)-1H-imidazole-2-carboxylic acid [4-bromo-2-(4,4-dimethyl-cyclohex-1-enyl)-phenyl]-amide

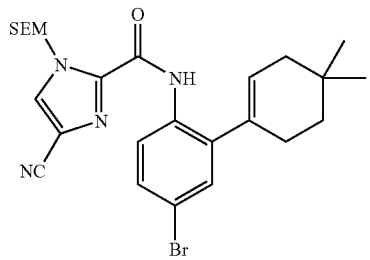

To a suspension of 4-bromo-2-(4,4-dimethyl-cyclohex-1-enyl)-phenylamine (0.640 g, 2.29 mmol, as prepared in the previous step) and 4-cyano-1-(2-trimethylsilanyl-ethoxymethyl)-1H-imidazole-2-carboxylate potassium salt (0.700 g, 2.30 mmol, as prepared in this Example, step (d)) in DCM (12 mL) was added DIPEA (0.800 mL, 4.60 mmol) and PyBrOP (1.29 g, 2.76 mmol) and the mixture allowed to stir at RT for 10 h. The mixture was diluted with DCM (50 mL) and washed with NaHCO$_3$ (2×50 mL) and the organic layer dried over Na$_2$SO$_4$ and concentrated. The title compound was eluted from a 20-g SPE with 1:1 DCM/hexane to give 1.04 g (86%) of a white solid: Mass spectrum (ESI, m/z) calcd. for C$_{25}$H$_{33}$BrN$_4$O$_2$Si, 529.1 (M+H), found 529.1.

g) 4-Cyano-1H-imidazole-2-carboxylic acid [4-bromo-2-(4,4-dimethyl-cyclohex-1-enyl)-phenyl]-amide

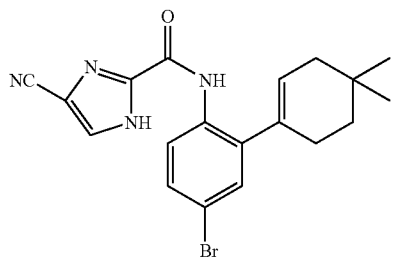

To a solution of 4-cyano-1-(2-trimethylsilanyl-ethoxymethyl)-1H-imidazole-2-carboxylic acid [4-bromo-2-(4,4-dimethyl-cyclohex-1-enyl)-phenyl]-amide (0.950 g, 1.80 mmol, as prepared in the previous step) in 10 mL of DCM was added 0.4 mL of EtOH and 10 mL of TFA and the mixture stirred for 1 h at RT. The mixture was concentrated and triturated with Et$_2$O to give 0.68 g (95%) of the title compound as a white solid: 1H-NMR (400 MHz, CDCl$_3$) δ 11.23 (br s, 1H), 9.52 (br s, 1H), 8.27 (d, J=8.7 Hz, 1H), 7.72 (s, 1H), 7.41 (dd, J=2.3, 8.7 Hz, 1H), 7.33 (d, J=2.3Hz, 1H), 5.82 (m, 1H), 2.28 (m, 2H), 2.10 (m, 2H), 1.58 (m, 2H), 1.08 (s, 6H). Mass spectrum (ESI, m/z) calcd. for C$_{19}$H$_{19}$BrN$_4$O 399.1 (M+H), found 399.0.

h) 5-Cyano-1H-imidazole-2-carboxylic acid [2-(4,4-dimethyl-cyclohex-1-enyl)-4-(4-hydroxy-tetrahydro-pyran-4-yl)-phenyl]-amide

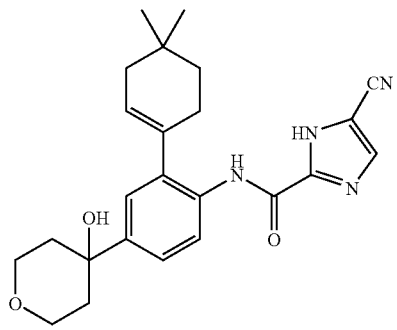

To a suspension of 4-cyano-1H-imidazole-2-carboxylic acid [4-bromo-2-(4,4-dimethyl-cyclohex-1-enyl)-phenyl]-amide (0.550 g, 1.38 mmol, as prepared in the previous step) in 20 mL THF at −40° C. was added i-PrMgCl (1.40 mL, 2 M in THF) and the solution was then warmed to 0° C. and stirred for 10 min. The solution was then cooled to −78° C. and t-BuLi (2.15 mL, 1.7 M in pentane) was added dropwise over 5 min and then tetrahydropyran-4-one (0.650 mL, 7.05 mmol) was added immediately thereafter. After 5 min at −78° C. the reaction was quenched with satd NH$_4$Cl (20 mL) and extracted with EtOAc (3×20 mL) and dried over Na$_2$SO$_4$. The title compound was purified by flash chromatography (silica gel) eluting with 50% EtOAc/DCM to give 0.46 g (79%) of a white solid: $^1$H-NMR (400 MHz, DMSO-d6) δ 14.28 (s, 1H), 9.77 (s, 1H), 8.21 (s, 1H), 7.98 (d, J=8.5 Hz, 1H), 7.38 (dd, J=8.5, 2.2 Hz, 1H), 7.34 (d, J=2.2 Hz, 1H), 5.67 (m, 1H), 5.03 (s, 1H), 3.83-3.66 (m, 4H), 2.31-2.22 (m, 2H), 2.04-1.92 (m, 4H), 1.58-1.46 (m, 4H), 1.01 (s, 6H). Mass spectrum (ESI, m/z) calcd. for C$_{24}$H$_{28}$N$_4$O$_3$ 421.2 (M+H), found 421.1.

i) 5-Cyano-1H-imidazole-2-carboxylic acid [4-(3,6-dihydro-2H-pyran-4-yl)-2-(4,4-dimethyl-cyclohex-1-enyl)-phenyl]-amide To a suspension of 5-cyano-1H-imidazole-2-carboxylic acid [2-(4,4-dimethyl-cyclohex-1-enyl)-4-(4-hydroxy-tetrahydro-pyran-4-yl)-phenyl]-amide (16.0 mg, 38.1 μmol, as prepared in the previous step) in 0.3 mL of toluene was added p-toluenesulfonic acid (14.0 mg, 74.0 mmol) and the mixture heated to 60° C. for 2 h. The solvent was evaporated and the title compound purified by RP-HPLC, eluting with a linear gradient of 40% CH$_3$CN in 0.1% TFA/H$_2$O to 100% CH$_3$CN over 20 min to give 8.0 mg (50%) of a white solid: $^1$H-NMR (400 MHz, CD$_3$OD) δ 8.23 (d, J=8.6 Hz, 1H), 8.02 (s, 1H), 7.38 (dd, J=8.6, 2.2 Hz, 1H), 7.26 (d, J=2.2 Hz, 1H), 6.20 (m, 1H), 5.78 (m, 1H), 4.32 (m, 2H), 3.94 (t, J=5.5, 5.5 Hz, 2H), 2.53 (m, 2H), 2.34 (m, 2H), 2.10 (m, 2H), 1.62 (t, J=6.3, 6.3 Hz, 2H), 1.12 (s, 6H). Mass spectrum (ESI, m/z) calcd. for C$_{24}$H$_{26}$N$_4$O$_2$ 403.2 (M+H), found 403.2.

EXAMPLE 61

4-Cyano-1H-imidazole-2-carboxylic acid {2-cyclohept-1-enyl-4-[1-(2-dimethylamino-acetyl)-piperidin-4-yl]-phenyl}-amide trifluoroacetic acid salt

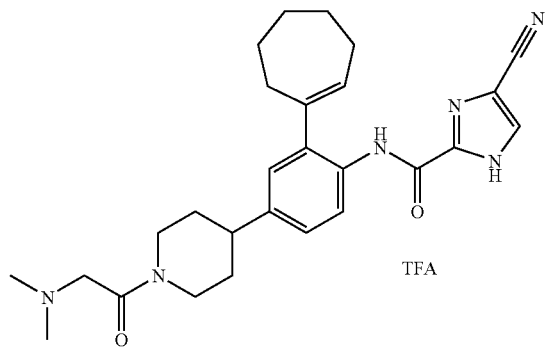

a) 4-(4-Amino-phenyl)-3,6-dihydro-2H-pyridine-1-carboxylic acid tert-butyl ester

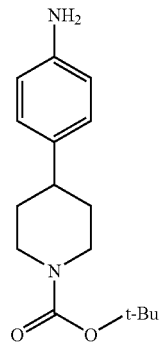

To a mixture of 4-trifluoromethanesulfonyloxy-3,6-dihydro-2H-pyridine-1-carboxylic acid tert-butyl ester (*Synthesis*, 993, (1991), 7.4 g, 22 mmol), 4-(4,4,5,5-tetramethyl-[1,3,2]dioxaborolan-2-yl)-phenylamine (4.0 g, 18 mmol) and Pd(PPh₃)₄ (2.3 g, 2.0 mmol) in 160 mL of toluene and 80 mL of absolute ethanol under Ar was added 2.0 M aq Na₂CO₃ solution (80 mL, 160 mmol). The resulting mixture was stirred at 80° C. for 3 h and then cooled to RT. After adding 600 mL of EtOAc, the mixture was washed with 1 M NaOH (250 mL), H₂O (2×250 mL), brine (300 mL) and dried (Na₂SO₄). Removal of the solvent under reduced pressure followed by flash chromatography of the residue on silica gel (20% EtOAc/hexane) gave 3.20 g (63%) of the title compound as a hard yellow foam: Mass spectrum (ESI, m/z): Calcd. for $C_{16}H_{22}N_2O_2$, 275.2 (M+H), found 275.1.

b) 4-(4-Amino-phenyl)-piperidine-1-carboxylic acid tert-butyl ester

A solution of 4-(4-amino-phenyl)-3,6-dihydro-2H-pyridine-1-carboxylic acid tert-butyl ester (0.35 g, 1.2 mmol, as prepared in the previous step) in 30 mL methanol was hydrogenated over 10% Pd/C at 20 psi for 1 h. The solution was filtered and concentrated to give 0.35 g (100%) of the title compound as a yellow solid: Mass spectrum (ESI, m/z): Calcd. for $C_{16}H_{24}N_2O_2$, 277.2 (M+H), found 277.1.

c) 4-(4-Amino-3-bromo-phenyl)-piperidine-1-carboxylic acid tert-butyl ester

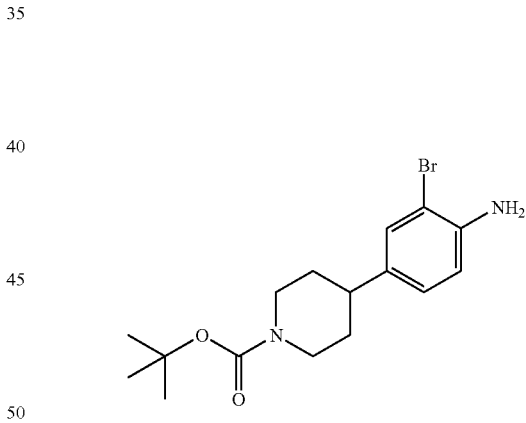

A solution of 2.00 g (7.24 mmol) 4-(4-amino-phenyl)-piperidine-1-carboxylic acid tert-butyl ester (as prepared in the previous step) in 40 mL of CH₃CN was treated with solid 1.25 g (7.02 mmol) NBS and stirred at RT for 15 min. The solvents were evaporated in vacuo, the residue was taken up in EtOAc (70 mL) and washed with saturated aqueous NaHCO₃ (2×50 mL). The combined organic layers were dried (MgSO₄) and concentrated in vacuo. Silica gel chromatography of the residue with 10-25% EtOAc-hexanes afforded 3.12 g (97%) of the title compound as a tan solid: Mass spectrum (ESI, m/z): Calcd. for $C_{12}H_{16}N_2O_2Br$, 299.0 (M−$C_4H_9$+2H), found 299.1/301.1.

d) 4-(4-Amino-3-cyclohept-1-enyl-phenyl)-piperidine-1-carboxylic acid tert-butyl ester

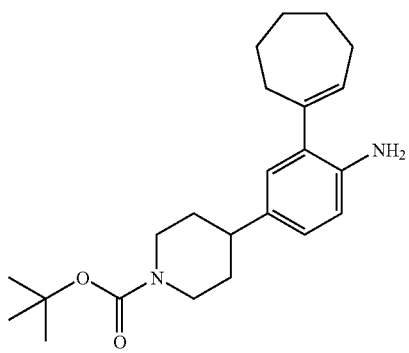

A solution of 230 mg (0.647 mmol) 4-(4-amino-3-bromophenyl)-piperidine-1-carboxylic acid tert-butyl ester (as prepared in the previous step) in 6 mL toluene and 3 mL EtOH was treated with 118 mg (0.842 mmol) cyclohept-1-enylboronic acid and 2.60 mL (5.18 mmol) 2.0 M $Na_2CO_3$. The mixture was degassed via sonication, placed under Ar, treated with 52.3 mg (0.0453 mmol) $Pd(PPh_3)_4$, and heated to 85° C. for 23 h. The mixture was diluted with EtOAc (15 mL) and washed with water (1×15 mL) and brine (1×15 mL). The combined aqueous layers were extracted with EtOAc (15 mL), and the combined organic layers were dried ($MgSO_4$) and concentrated in vacuo. Silica gel chromatography of the residue on a Varian MegaBond Elut 50-gm column with 10-18% EtOAc-hexane afforded 108 mg (45%) of the title compound as a tan solid: Mass spectrum (ESI, m/z): Calcd. for $C_{19}H_{27}N_2O_2$, 315.2 ($M-C_4H_9+2H$), found 315.2.

e) 4(4-{[4-Cyano-1-(2-trimethylsilanyl-ethoxymethyl)-1H-imidazole-2-carbonyl]-amino}-3-cyclohept-1-enyl-phenyl)-piperidine-1-carboxylic acid tert-butyl ester

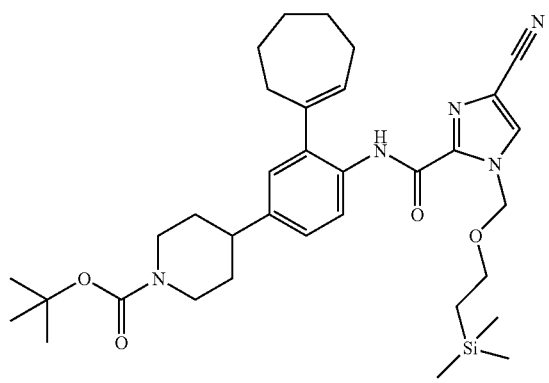

A solution of 108 mg (0.292 mmol) 4-(4-amino-3-cyclohept-1-enyl-phenyl)-piperidine-1-carboxylic acid tert-butyl ester (as prepared in the previous step) in 10 mL $CH_2Cl_2$ was treated with 97.9 mg (0.321 mmol) 4-cyano-1-(2-trimethylsilanyl-ethoxymethyl)-1H-imidazole-2-carboxylate potassium salt (as prepared in Example 1, step (d)), 204 mg (0.437 mmol) PyBrOP, and 152 µL (0.874 mmol) DIEA and stirred at RT for 17 h. The mixture was diluted with $CH_2Cl_2$ (20 mL) and washed with saturated $NaHCO_3$ (1×15 mL) and water (1×15 mL). The organic layer was dried ($MgSO_4$) and concentrated in vacuo. Silica gel chromatography of the residue on a Varian MegaBond Elut 50-gm column with 10-25% EtOAc-hexane afforded 160 mg (88%) of the title compound as an off-white solid: Mass spectrum (ESI, m/z): Calcd. for $C_{30}H_{42}N_5O_4Si$, 563.3 ($M-C_4H_9+2H$), found 563.9.

f) 4-Cyano-1H-imidazole-2-caboxylic acid (2-cyclohept-1-enyl-4-piperidin-4-yl-phenyl)-amide

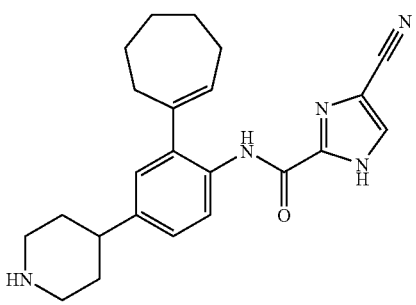

A solution of 160 mg (0.258 mmol) 4-(4-{[4-cyano-1-(2-trimethylsilanyl-ethoxymethyl)-1H-imidazole-2-carbonyl]-amino}-3-cyclohept-1-enyl-phenyl)-piperidine-1-carboxylic acid tert-butyl ester (as prepared in the previous step) in 10 mL $CH_2Cl_2$ was treated with 200 µL MeOH and 3 mL TFA at RT for 3.5 h. Solvents were evaporated in vacuo. The residue was taken up in $CH_2Cl_2$ (30 mL) and washed with saturated aqueous $NaHCO_3$ (1×20 mL). The organic layer was dried ($MgSO_4$) and concentrated in vacuo to afford 100 mg (100%) of the title compound as a white solid: Mass spectrum (ESI, m/z): Calcd. for $C_{23}H_{27}N_5O$, 390.2 (M+H), found 390.3.

g) 4-Cyano-1H-imidazole-2-carboxylic acid {2-cyclohept-1-enyl-4-[1-(2-dimethylamino-acetyl)-piperidin-4-yl]-phenyl}-amide trifluoroacetic acid salt A suspension of 39.7 mg (0.385 mmol) dimethylaminoacetic acid in 5 mL $CH_2Cl_2$ was treated with 94.8 mg (0.372 mmol) BOP—Cl and 143 µL (1.03 mmol) triethylamine at RT for 1 h. This mixture was added to a suspension of 100 mg (0.257 mmol) 4-cyano-1H-imidazole-2-carboxylic acid (2-cyclohept-1-enyl-4-piperidin-4-yl-phenyl)-amide (as prepared in the previous step) in 5 mL $CH_2Cl_2$. The mixture stirred at RT for 22 h, was diluted with $CH_2Cl_2$ (15 mL), and washed with saturated aqueous $NaHCO_3$ (10 mL). The organic layer was dried ($MgSO_4$) and concentrated in vacuo. Purification of the residue by RP-HPLC (C18) with 20-60% $CH_3CN$ in 0.1% $TFA/H_2O$ over 30 min to afford 32.1 mg (21%) of the title compound as a white solid: $^1$H-NMR ($CD_3OD$; 400 MHz): δ 8.09 (d, 1H, J=8.4 Hz), 8.03 (br s, 1H), 7.18 (dd, 1H, J=8.4 Hz, J=2.4 Hz), 7.07 (d, 1H, J=2.4 Hz), 5.98 (t, 1H, J=6.4 Hz), 4.72-4.64 (m, 1H), 4.31 (q, 2H, J=16.4 Hz), 3.83-3.75 (m, 1H), 3.31-3.22 (m, 1H), 3.03-2.94 (m, 6H), 2.92-2.81 (m, 2H), 2.54-2.47 (m, 2H), 2.43-2.35 (m, 2H), 1.99-1.87 (m, 4H), 1.83-1.68 (m, 6H), 1.69-1.59 (m, 1H). Mass spectrum (ESI, m/z): Calcd. for $C_{27}H_{34}N_6O_2$, 475.3 (M+H), found 475.3.

EXAMPLE 62

4-Cyano-1H-imidazole-2-carboxylic acid [4-[1-(2-dimethylamino-acetyl)-piperidin-4-yl]-2-(4,4-dimethyl-cyclohex-1-enyl)-phenyl]-amide trifluoroacetic acid salt

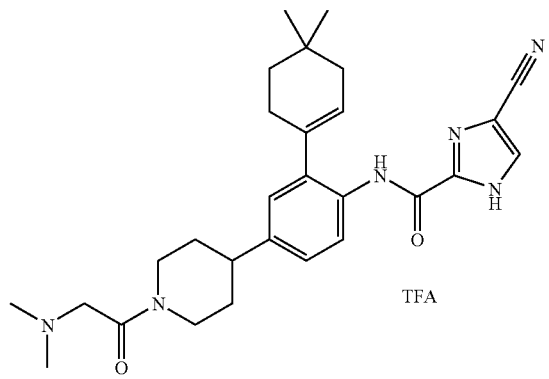

a) 4-[4-Amino-3-(4,4dimethyl-cyclohex-1-enyl)-phenyl]-piperidine-4-carboxylic acid tert-butyl ester

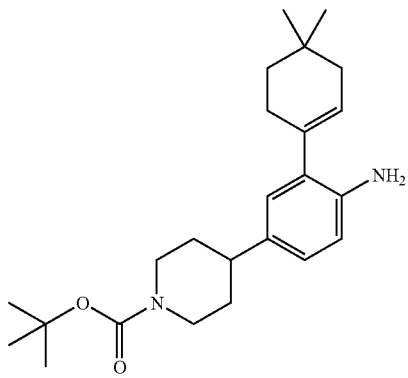

A solution of 250 mg (0.704 mmol) 4-(4-amino-3-bromo-phenyl)-piperidine-1-carboxylic acid tert-butyl ester (as prepared in Example 61, step (c)) in 6 mL toluene and 3 mL EtOH was treated with 119 mg (0.774 mmol) 4,4-dimethyl-cyclohex-1-enylboronic acid and 2.81 mL (5.63 mmol) 2.0 M $Na_2CO_3$. The mixture was degassed via sonication, placed under Ar, treated with 56.9 mg (0.0493 mmol) $Pd(PPh_3)_4$, and heated to 85° C. for 27 h and allowed to stand at RT for 36 h. The mixture was diluted with EtOAc (15 mL) and washed with water (1×15 mL). The combined aqueous layers were extracted with EtOAc (15 mL), and the combined organic layers were dried ($MgSO_4$) and concentrated in vacuo. Silica gel chromatography of the residue on a Varian MegaBond Elut 50-gm column with 10-15% EtOAc-hexane afforded 89.0 mg (33%) of the title compound as a tan solid: Mass spectrum (ESI, m/z): Calcd. for $C_{20}H_{29}N_2O_2$, 329.2 ($M-C_4H_9+2H$), found 329.2.

b) 4-[4-{[4-Cyano-1-(2-trimethylsilanyl-ethoxymethyl)-1H-imidazole-2-carbonyl]-amino}-3-(4,4-dimethyl-cyclohex-1-enyl)-phenyl]-piperidine-1-carboxylic acid tert-butyl ester

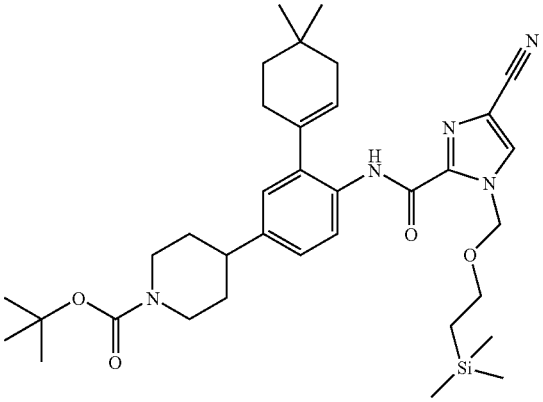

A solution of 89.0 mg (0.231 mmol) 4-[4-amino-3-(4,4-dimethyl-cyclohex-1-enyl)-phenyl]-piperidine-1-carboxylic acid tert-butyl ester (as prepared in the previous step) in 10 mL $CH_2Cl_2$ was treated with 77.8 mg (0.255 mmol) 4-cyano-1-(2-trimethylsilanyl-ethoxymethyl)-1H-imidazole-2-carboxylate potassium salt (as prepared in Example 1, step (d)), 162 mg (0.347 mmol) PyBrOP, and 121 μL (0.694 mmol) DIEA and stirred at RT for 2 h. The mixture was diluted with $CH_2Cl_2$ (20 mL) and washed with saturated $NaHCO_3$ (1×15 mL) and water (1×15 mL). The organic layer was dried ($MgSO_4$) and concentrated in vacuo. Silica gel chromatography of the residue on a Varian MegaBond Elut 50-gm column with 10-25% EtOAc-hexane afforded 124 mg (84%) of the title compound as an off-white solid: Mass spectrum (ESI, m/z): Calcd. for $C_{31}H_{44}N_5O_4Si$, 578.3 ($M-C_4H_9+2H$), found 578.0.

c) 4-Cyano-1H-imidazole-2-carboxylic acid[2-(4,4-dimethyl-cyclohex-1-enyl)-4-piperidin-4-yl-phenyl]-amide

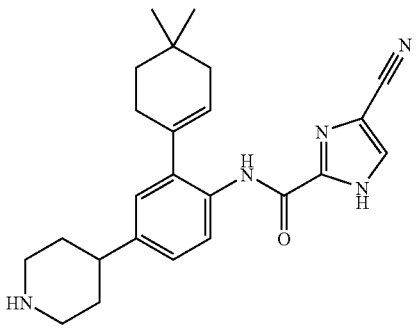

A solution of 124 mg (0.196 mmol) 4-[4-{[4-cyano-1-(2-trimethylsilanyl-ethoxymethyl)-1H-imidazole-2-carbonyl]-amino}-3-(4,4-dimethyl-cyclohex-1-enyl)-phenyl]-piperidine-1-carboxylic acid tert-butyl ester (as prepared in the previous step) in 10 mL $CH_2Cl_2$ was treated with 200 μL MeOH and 3 mL TFA at RT for 3.5 h. Solvents were evaporated in vacuo. The residue was taken up in $CH_2Cl_2$ (30 mL)

and washed with saturated aqueous NaHCO$_3$ (1×20 mL). The organic layer was dried (MgSO$_4$) and concentrated in vacuo to afford 70.0 mg (89%) of the title compound as a white solid: Mass spectrum (ESI, m/z): Calcd. for C$_{24}$H$_{29}$N$_5$O, 404.2 (M+H), found 404.3.

d) 4-Cyano-1H-imidazole-2-carboxylic acid [4-[1-(2-dimethylamino-acetyl)-piperidin-4-yl]-2-(4,4-dimethyl-cyclohex-1-enyl)-phenyl]-amide trifluoroacetic acid salt A suspension of 26.8 mg (0.260 mmol) dimethylamino-acetic acid in 4 mL CH$_2$Cl$_2$ was treated with 64.0 mg (0.372 mmol) BOP—Cl and 96.7 μL (0.694 mmol) triethylamine at RT for 1 h. This mixture was added to a suspension of 70.0 mg (0.173 mmol) 4-cyano-1H-imidazole-2-carboxylic acid [2-(4,4-dimethyl-cyclohex-1-enyl)-4-piperidin-4-yl-phenyl]-amide (as prepared in the previous step) in 5 mL CH$_2$Cl$_2$. The mixture stirred at RT for 17 h, was diluted with CH$_2$Cl$_2$ (15 mL), and washed with saturated aqueous NaHCO$_3$ (10 mL). The organic layer was dried (MgSO$_4$) and concentrated in vacuo. Purification of the residue by RP-HPLC (C18) with 20-60% CH$_3$CN in 0.1% TFA/H$_2$O over 30 min to afford 57.3 mg (55%) of the title compound as a white solid: $^1$H-NMR (CD$_3$OD; 400 MHz): δ 8.15 (d, 1H, J=8.4 Hz), 8.02 (s, 1H), 7.20 (dd, 1H, J=8.4 Hz, J=2.0 Hz), 7.10 (d, 1H, J=2.0 Hz), 5.77-5.72 (m, 1H), 4.72-4.64 (m, 1H), 4.30 (q, 2H, J=16.0 Hz), 3.83-3.75 (m, 1H), 3.30-3.21 (m, 1H), 2.98 (d, 6H, J=9.2 Hz), 2.93-2.81 (m, 2H), 2.36-2.28 (m, 2H), 2.11-2.06 (m, 2H), 1.99-1.90 (m, 2H), 1.82-1.62 (m, 2H), 1.61 (t, 2H, J=6.4 Hz), 1.10 (s, 6H). Mass spectrum (ESI, m/z): Calcd. for C$_{27}$H$_{34}$N$_6$O$_2$, 475.3 (M+H), found 475.3. Mass spectrum (ESI, m/z): Calcd. for C$_{28}$H$_{36}$N$_6$O$_2$, 489.3 (M+H), found 489.4.

EXAMPLE 63

4-Cyano-1H-pyrrole-2-carboxylic acid {2-cyclohex-1-enyl-4-[1-(2-dimethylamino-acetyl)-piperidin-4-yl]-phenyl}-amide trifluoroacetic acid salt

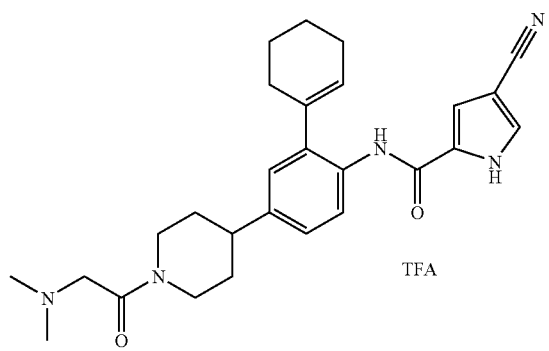

a) 4-(4-Amino-3-cyclohex-1-enyl-phenyl)-piperidine-1-carboxylic acid tert-butyl ester

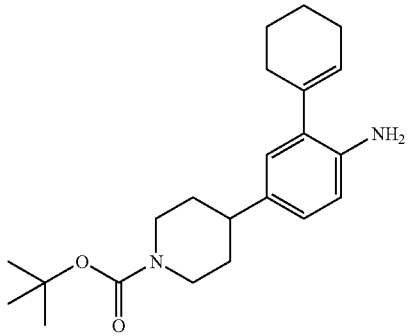

A solution of 500 mg (1.41 mmol) 4-(4-amino-3-bromo-phenyl)-piperidine-1-carboxylic acid tert-butyl ester (as prepared in Example 61, step (c)) in 11.2 mL toluene and 5.6 mL EtOH was treated with 5.63 mL (11.3 mmol) 2.0 M aqueous Na$_2$CO$_3$ and 381 mg (1.83 mmol) 2-cyclohex-1-enyl-4,4,5,5-tetramethyl-[1,3,2]dioxaborolane. The mixture was degassed via sonication, placed under Ar, treated with 163 mg (0.141 mmol) Pd(PPh$_3$)$_4$, and heated to 80° C. for 22 h. The mixture was diluted with EtOAc (30 mL) and washed with water (2×20 mL). The combined aqueous layers were extracted with EtOAc (1×30 mL) and the combined organic layers were dried (MgSO$_4$) and concentrated in vacuo. Silica gel chromatography of the residue on a Varian MegaBond Elut 50-gm column with 10-25% EtOAc-hexanes afforded 445 mg (89%) as a tan solid: Mass spectrum (ESI, m/z): Calcd. for C$_{18}$H$_{25}$N$_2$O$_2$, 301.2 (M–C$_4$H$_9$+2H), found 301.2.

b) 4-{4-[(4-Cyano-1H-pyrrole-2-carbonyl)-amino]-3-cyclohex-1-enyl-phenyl}-piperidine-1-carboxylic acid tert-butyl ester A suspension of 101 mg (0.741 mmol) 4-cyano-1H-pyrrole-2-carboxylic acid (*Canadian J. Chem.* 59: 2673 (1981)) in 20 mL CH$_3$CN was treated with 116 μL (0.741 mmol) (1-chloro-2-methyl-propenyl)-dimethylamine at RT for 20 min. The mixture was added to a solution of 220 mg (0.617 mmol) of 4-(4-amino-3-cyclohex-1-enyl-phenyl)-piperidine-1-carboxylic acid tert-butyl ester (as prepared in the previous step) in 10 mL CH$_3$CN, stirred at RT for 20 h and the solvents evaporated in vacuo. Silica gel chromatography of the residue on a Varian MegaBond Elut 25-gm column with 10-25% EtOAc-hexane afforded 36.0 mg (12%) of the title compound as an off-white solid: Mass spectrum (ESI, m/z): Calcd. for $C_{24}H_{27}N_4O_3$, 419.2 (M−$C_4H_9$+2H), found 419.1.

c) 4-Cyano-1H-pyrrole-2-carboxylic acid (2-cyclohex-1-enyl-4-piperidin-4-yl-phenyl)-amide trifluoroacetic acid salt

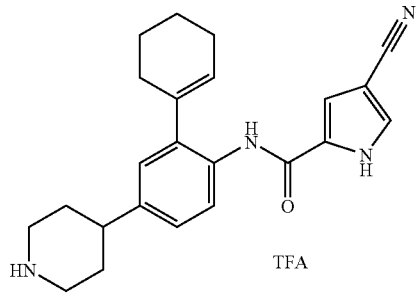

A solution of 36.0 mg (0.0759 mmol) 4-{4-[(4-cyano-1H-pyrrole-2-carbonyl)-amino]-3-cyclohex-1-enyl-phenyl}-piperidine-1-carboxylic acid tert-butyl ester (as prepared in the previous step) in 5 mL $CH_2Cl_2$ was treated with 4 drops MeOH and 1 mL TFA and stirred at RT for 2 h. MeOH (5 mL) was added, and solvents were evaporated in vacuo. Purification of the residue by RP-HPLC (C18) with 10-80% $CH_3CN$ in 0.1% TFA/$H_2O$ over 30 min afforded 22.0 mg (59%) of the title compound as a white solid: Mass spectrum (ESI, m/z): Calcd. for $C_{23}H_{26}N_4O$, 375.2 (M+H), found 375.2.

d) 4-Cyano-1H-pyrrole-2-carboxylic acid {2-cyclohex-1-enyl-4-[1-(2-dimethylamino-acetyl)-piperidin-4-yl]-phenyl}-amide trifluoroacetic acid salt A suspension of 9.10 mg (0.0881 mmol) dimethylamino-acetic acid in 5 mL $CH_2Cl_2$ was treated with 21.7 mg (0.0852 mmol) BOP—Cl and 32.8 µL (0.235 mmol) triethylamine at RT for 50 min. This mixture was added to a suspension of 22.0 mg (0.0588 mmol) 4-cyano-1H-pyrrole-2-carboxylic acid (2-cyclohex-1-enyl-4-piperidin-4-yl-phenyl)-amide trifluoroacetic acid salt (as prepared in the previous step) in 5 mL $CH_2Cl_2$. The mixture stirred at RT for 23 h, was diluted with $CH_2Cl_2$ (15 mL), and washed with saturated aqueous $NaHCO_3$ (1×10 mL). The organic layer was dried ($MgSO_4$) and concentrated in vacuo. Purification of the residue by RP-HPLC (C18) with 20-80% $CH_3CN$ in 0.1% TFA/$H_2O$ over 30 min to afford 33.6 mg (83%) of the title compound as a white solid: $^1$H-NMR ($CD_3OD$; 400 MHz): δ 7.54 (d, 1H, J=1.6 Hz), 7.41 (d, 1H, J=8.0 Hz), 7.14 (dd, 1H, J=8.4 Hz, J=2.0 Hz), 7.12-7.08 (m, 1H), 7.07 (d, 1H, J=2.0 Hz), 5.70-5.65 (m, 1H), 4.67-4.59 (m, 1H), 4.26 (q, 2H, J=16.4 Hz), 3.78-3.70 (m, 1H), 3.26-3.17 (m, 1H), 2.97-2.89 (m, 6H), 2.88-2.75 (m, 2H), 2.25-2.18 (m, 2H), 2.15-2.07 (m, 2H), 1.94-1.85 (m, 2H), 1.76-1.54 (m, 6H). Mass spectrum (ESI, m/z): Calcd. for $C_{27}H_{33}N_5O_2$, 460.3 (M+H), found 460.3.

EXAMPLE 64

4-Cyano-1-imidazole-2-carboxilic acid {2-(4,4-dimethyl-cyclohex-1-enyl)-4-[1-(2-methanesulfonyl-ethyl)-piperidin-4-yl]-phenyl}-amide trifluoroacetic acid salt

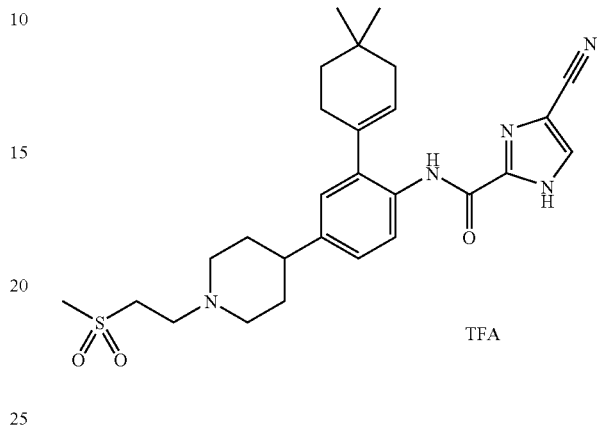

a) Methanesulfonic acid 2-methanesulfonyl-ethyl ester

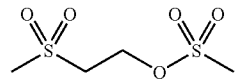

To a solution of methanesulfonyl chloride (484 mg, 4.23 mmol) in 15 mL of $CH_2Cl_2$ at 0° C. was added 2-methanesulfonyl-ethanol (500 mg, 4.03 mmol) in 10 mL of $CH_2Cl_2$ followed by DIEA (1.05 mL, 6.05 mmol) under Ar. The mixture was warmed to RT and stirred for 20 h under Ar. The mixture was treated with 100 mL of EtOAc and washed with $H_2O$ (3×20 mL), brine (20 mL) and dried ($Na_2SO_4$). Removal of the solvent in vacuo gave 534 mg (66%) of the title compound as a brown oil: $^1$H-NMR ($CDCl_3$; 400 MHz): δ 4.67 (d, 2H, J=5.5 Hz), 3.46 (d, 2H, J=5.5 Hz), 3.11 (s, 3H), 3.04 (s, 3H).

b) 4-Cyano-1-imidazole-2-carboxilic acid {2-(4,4-dimethyl-cyclohex-1-enyl)-4-[1-(2-methanesulfonyl-ethyl)-piperidin-4-yl]-phenyl}-amide trifluoroacetic acid salt A solution of 522 mg (1.01 mmol) of 4-cyano-1H-imidazole-2-carboxylic acid[2-(4,4-dimethyl-cyclohex-1-enyl)-4-piperidin-4-yl-phenyl]-amide (as prepared in Example 62, step (c)) in 30 mL $CH_2Cl_2$ was treated with 245 mg (1.21 mmol) methanesulfonic acid 2-methanesulfonyl-ethyl ester (as prepared in the previous step) and 527 µL (3.03 mmol) DIEA and stirred at RT for 25 h. The mixture was diluted with $CH_2Cl_2$ (50 mL) and washed with saturated aqueous $NaHCO_3$ (1×50 mL). The organic layer was dried ($MgSO_4$) and concentrated in vacuo. The residue was purified by RP-HPLC (C18) with 30-50% $CH_3CN$ in 0.1% TFA/$H_2O$ over 30 min to afford 15.3 mg (3%) of the title compound as a white solid: 1H-NMR ($CD_3OD$; 400 MHz): δ 8.20 (d, 1H, J=8.8 Hz), 8.02 (s, 1H), 7.26-7.19 (m, 1H), 7.16-7.10 (m, 1H), 5.78-5.73 (m, 1H), 3.83-3.63 (m, 6H), 3.29-3.17 (m, 2H), 3.14 (s, 3H), 2.99-2.88 (m, 1H), 2.37-2.28 (m, 2H), 2.23-2.13 (m, 2H), 2.12-2.07 (m, 2H), 2.07-1.93 (m. 2H), 1.61 (t, 2H, J=6.0 Hz), 1.10 (s, 6H). Mass spectrum (ESI, m/z): Calcd. for $C_{27}H_{35}N_5O_3S$, 510.3 (M+H), found 510.2.

IV. Results

An autophosphorylation, fluorescence polarization competition immunoassay was used to determine the potency for c-fms inhibition exhibited by selected compounds of Formula I. The assay was performed in black 96-well microplates (LJL BioSystems). The assay buffer used was 100 mM 4-(2-hydroxyethyl)piperazine 1-ethanesulfonic acid (HEPES), pH 7.5, 1 mM 1,4-dithio-DL-threitol (DTT), 0.01% (v/v) Tween-20. Compounds were diluted in assay buffer containing 4% dimethylsulfoxide (DMSO) just prior to the assay. To each well, 5 µL of compound were added followed by the addition of 3 µL of a mix containing 33 nM c-fms (Johnson & Johnson PRD) and 16.7 mM $MgCl_2$ (Sigma) in assay buffer. The kinase reaction was initiated by adding 2 µL of 5 mM ATP (Sigma) in assay buffer. The final concentrations in the assay were 10 nM c-fms, 1 mM ATP, 5 mM $MgCl_2$, 2% DMSO. Control reactions were ran in each plate: in positive and negative control wells, assay buffer (made 4% in DMSO) was substituted for the compound; in addition, positive control wells received 1.2 µL of 50 mM ethylenediaminetetraaceticacid (EDTA).

The plates were incubated at room temperature for 45 min. At the end of the incubation, the reaction was quenched with 1.2 µL of 50 mM EDTA (EDTA was not added to the positive control wells at this point; see above). Following a 5-min incubation, each well received 10 µL of a 1:1:3 mixture of anti-phosphotyrosine antibody, 10X, PTK green tracer, 10X (vortexed), FP dilution buffer, respectively (all from PanVera, cat. # P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. The reported $IC_{50}$ values are averages of three independent measurements.

Table 1 lists representative compounds of the invention.

TABLE 1

| Example # | Structure | c-fms IC50 (µM) |
|---|---|---|
| 4 | 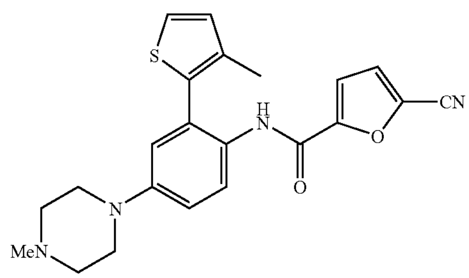 | 0.47 |
| 5 | 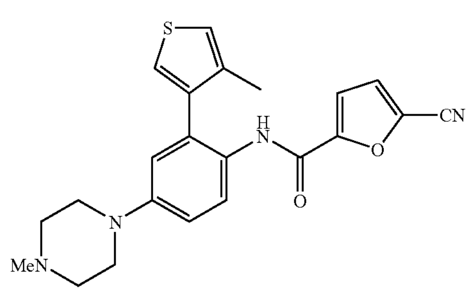 | 0.95 |

TABLE 1-continued
| Example # | Structure | c-fms IC50 (μM) |
|---|---|---|
| 6 | 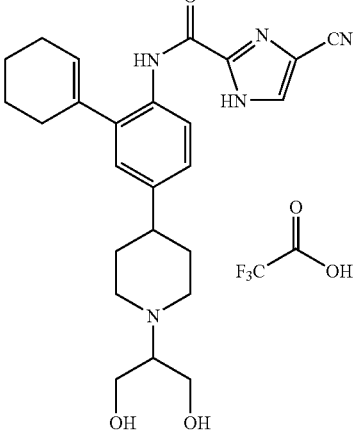 | 0.0016 |
| 7 | 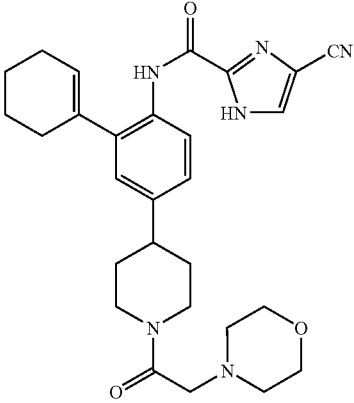 | 0.0043 |
| 8 | 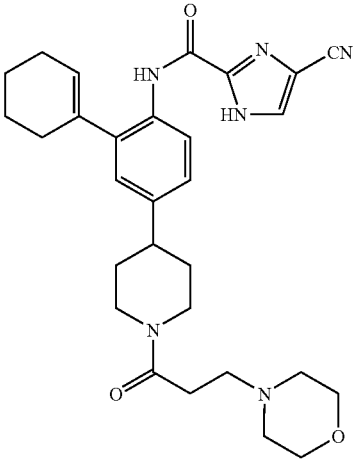 | 0.001 |

TABLE 1-continued
| Example # | Structure | c-fins IC50 (µM) |
|---|---|---|
| 9 | 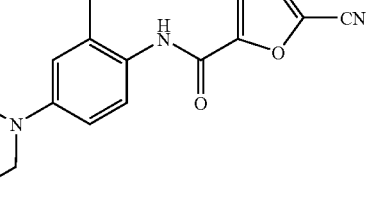 | 0.63 |
| 10 | 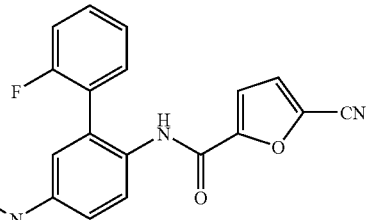 | 0.9 |
| 11 | 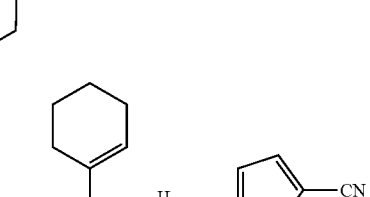 | 0.012 |
| 12 | 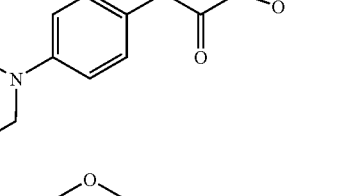 | 0.06 |
| 13 | 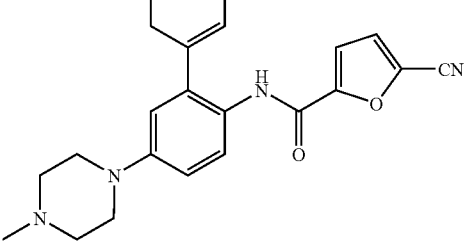 | 0.012 |

TABLE 1-continued

| Example # | Structure | c-fms IC50 (μM) |
|---|---|---|
| 14 | 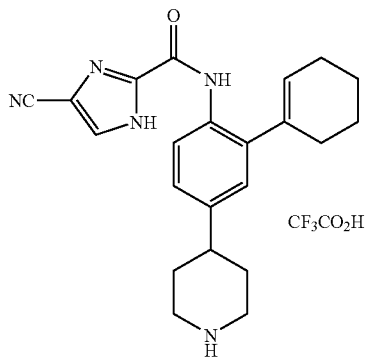 | 0.018 |
| 15 | 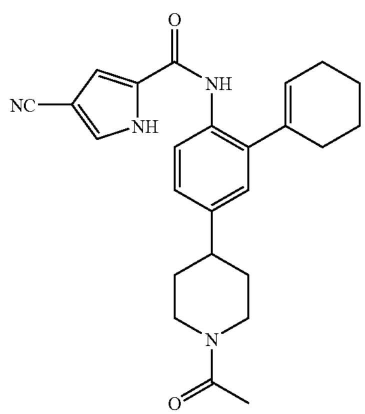 | 0.028 |
| 16 | 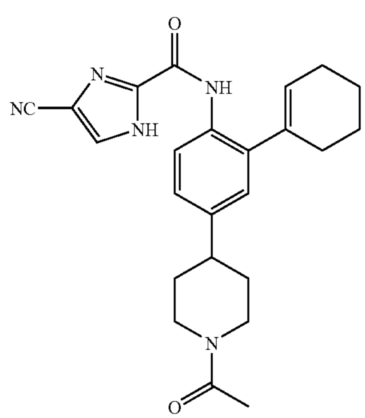 | 0.0026 |
| 17 | 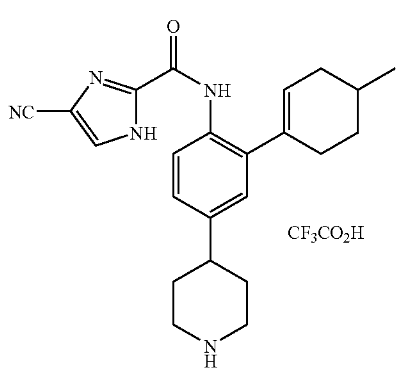 | 0.00055 |

TABLE 1-continued
| Example # | Structure | c-fms IC50 (μM) |
|---|---|---|
| 18 | 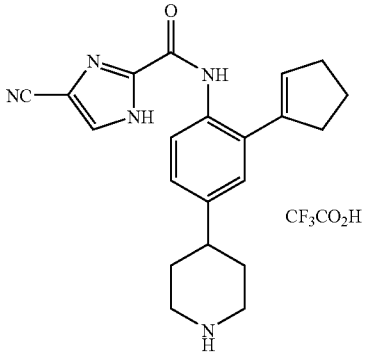 | 0.0082 |
| 20 | 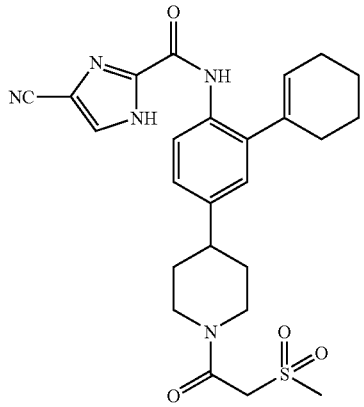 | 0.002 |
| 21 | 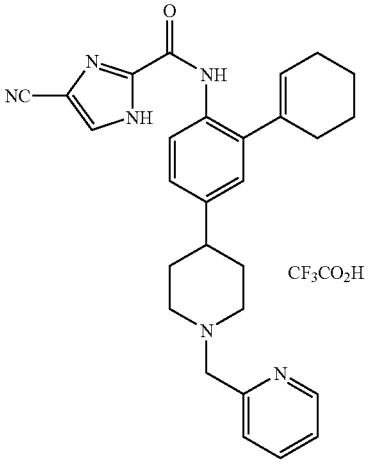 | 0.0024 |

TABLE 1-continued

| Example # | Structure | c-fms IC50 (μM) |
|---|---|---|
| 22 | 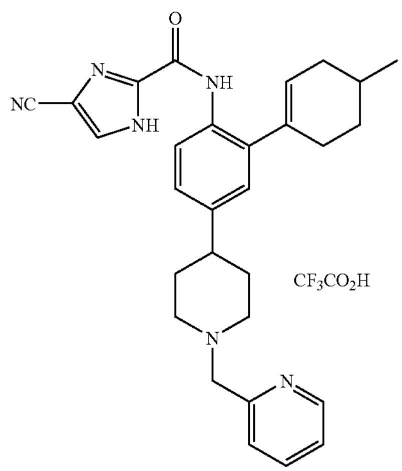 | 0.0014 |
| 23 | 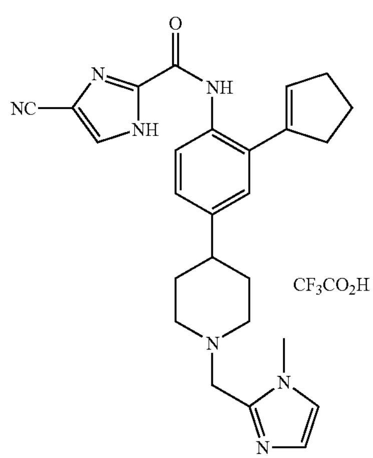 | 0.0066 |
| 24 | 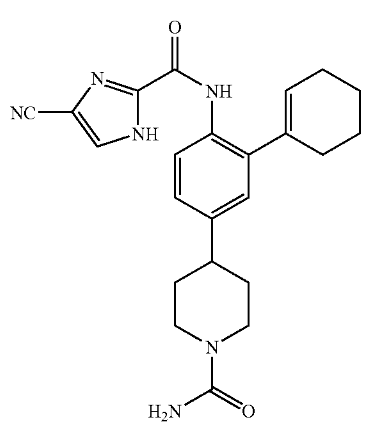 | 0.0046 |

TABLE 1-continued

| Example # | Structure | c-fms IC50 (μM) |
|---|---|---|
| 25 | 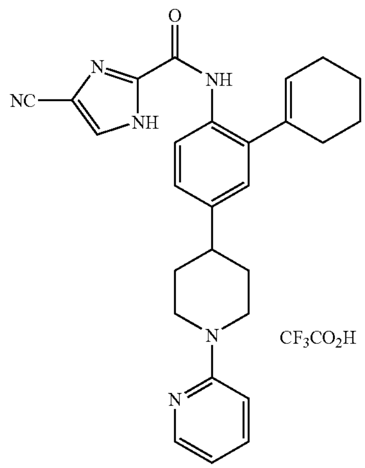 | 0.022 |
| 26 | 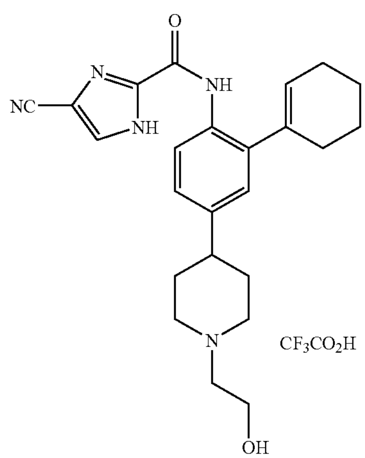 | 0.0011 |
| 27 | 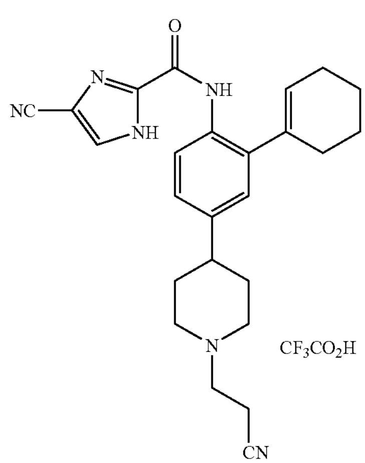 | 0.0016 |

TABLE 1-continued

| Example # | Structure | c-fms IC50 (μM) |
|---|---|---|
| 28 | 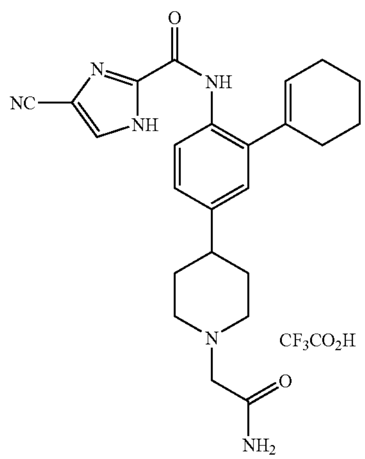 | 0.0014 |
| 29 | 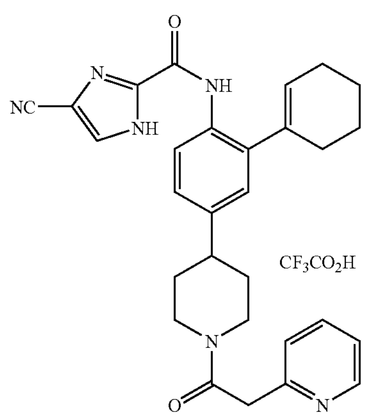 | 0.0025 |
| 30 | 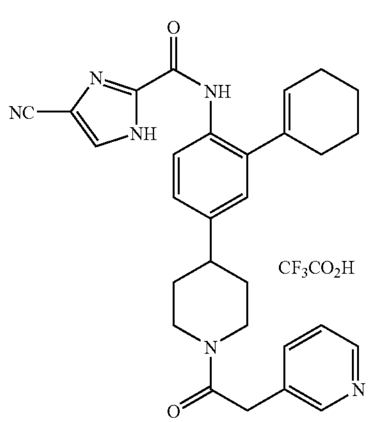 | 0.001 |

TABLE 1-continued

| Example # | Structure | c-fms IC50 (μM) |
|---|---|---|
| 31 | 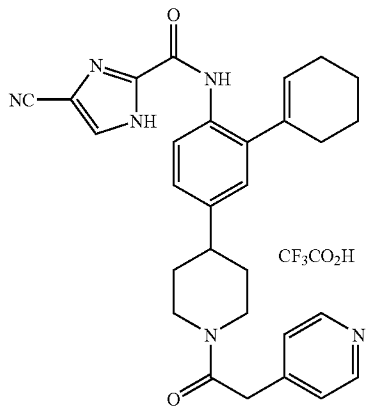 | 0.0014 |
| 32 | 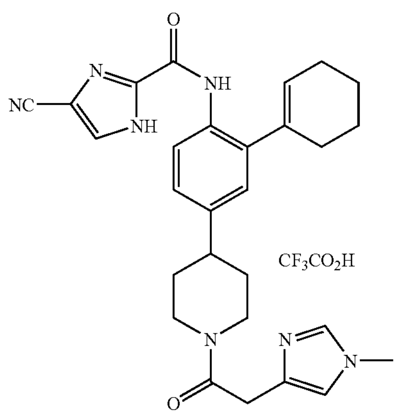 | 0.0018 |
| 33 | 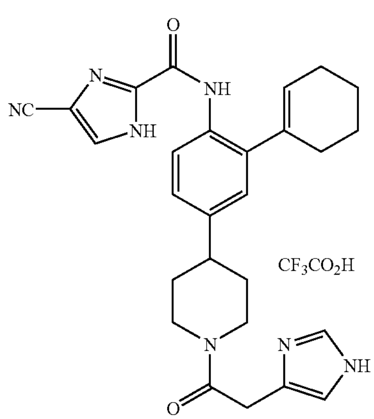 | 0.0011 |

TABLE 1-continued
| Example # | Structure | c-fms IC50 (μM) |
|---|---|---|
| 34 | 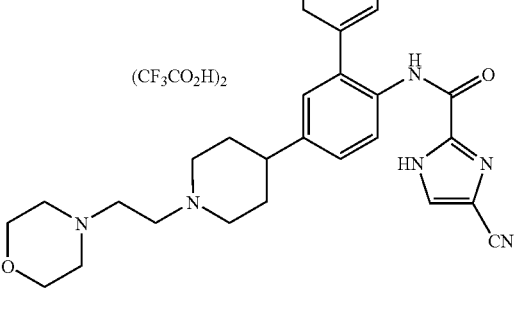 | 0.0018 |
| 35 | 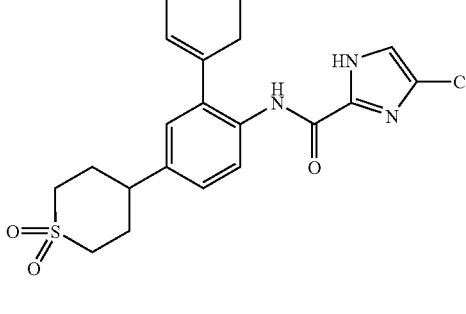 | 0.0029 |
| 36 | 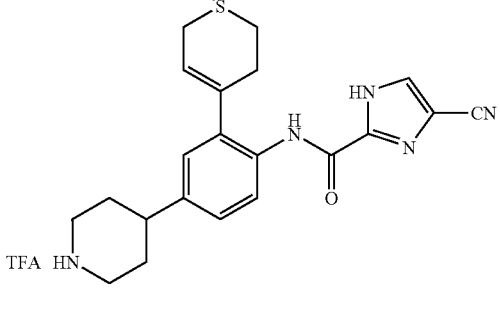 | 0.060 |
| 37 | 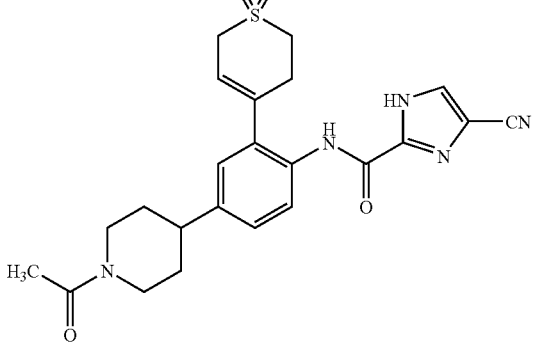 | 0.060 |

TABLE 1-continued
| Example # | Structure | c-fins IC50 (μM) |
|---|---|---|
| 38 | 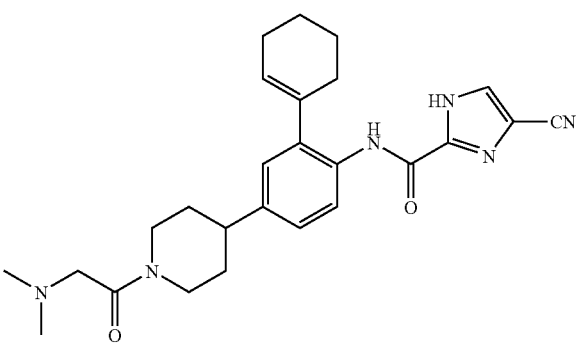 | 0.0024 |
| 38b | 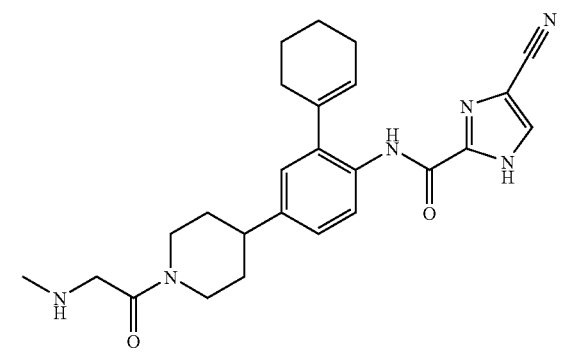 | 0.0014 |
| 39 | 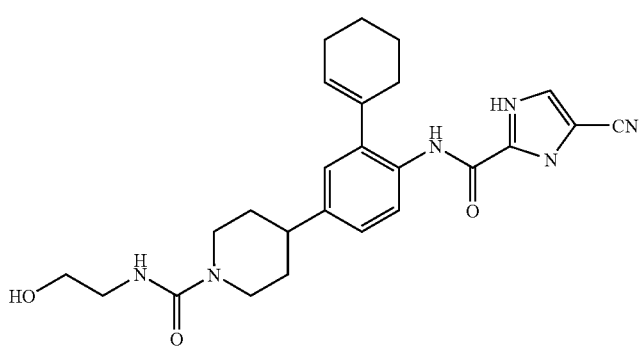 | 0.00095 |
| 40 | 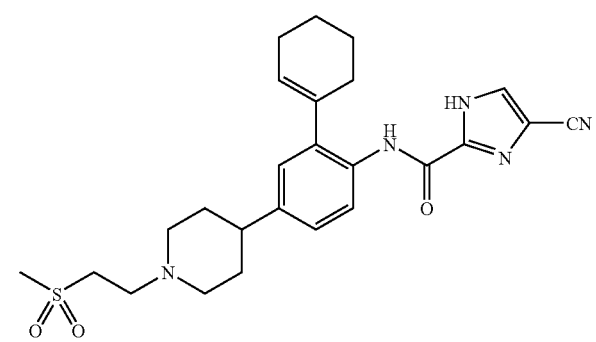 | 0.0019 |

TABLE 1-continued

| Example # | Structure | c-fins IC50 (μM) |
|---|---|---|
| 41 | 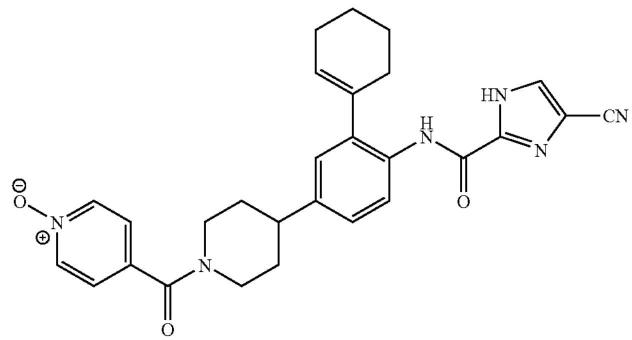 | 0.0013 |
| 42 | 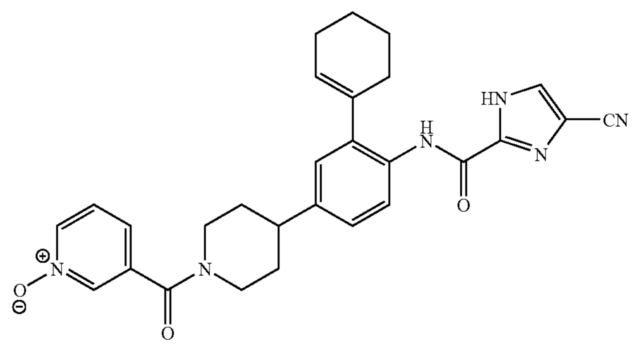 | 0.0014 |
| 43 | 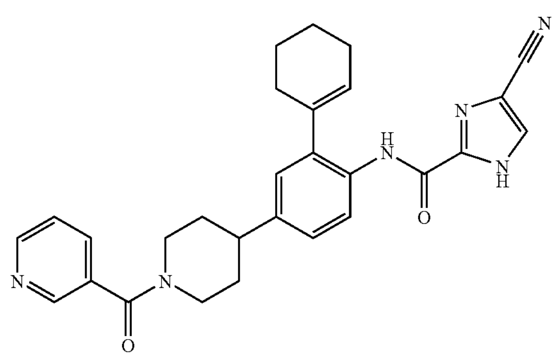 | 0.0031 |
| 44 | 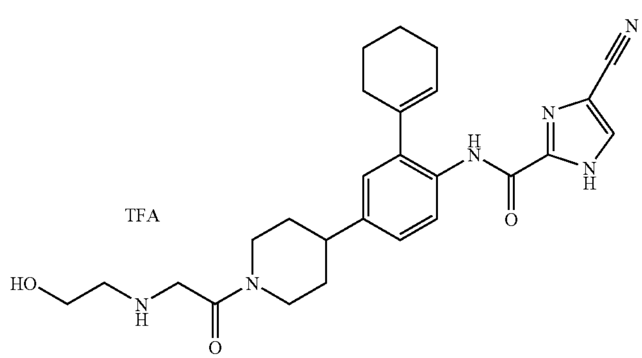 | 0.00095 |

TABLE 1-continued
| Example # | Structure | c-fins IC50 (μM) |
|---|---|---|
| 45 | 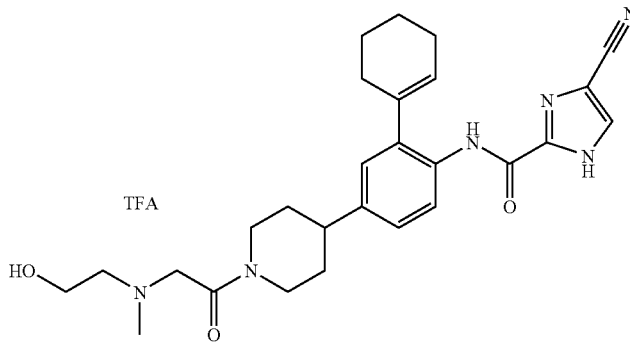 | 0.001 |
| 46 | 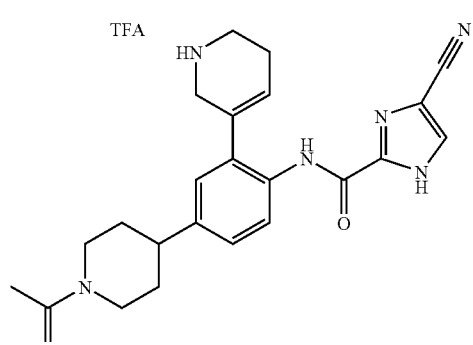 | N/A |
| 47 | 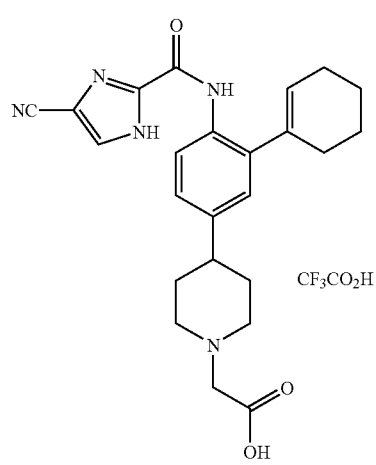 | 0.0013 |
| 48 | 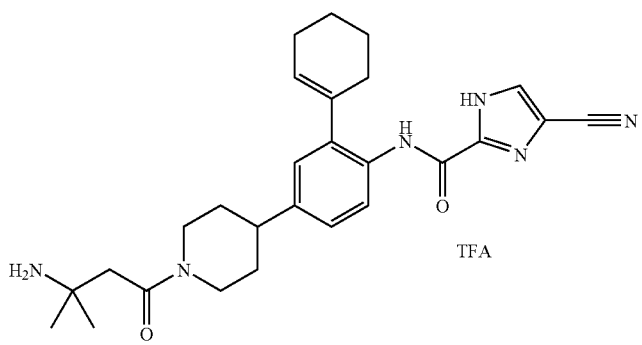 | 0.00064 |

TABLE 1-continued

| Example # | Structure | c-fms IC50 (μM) |
|---|---|---|
| 49 | 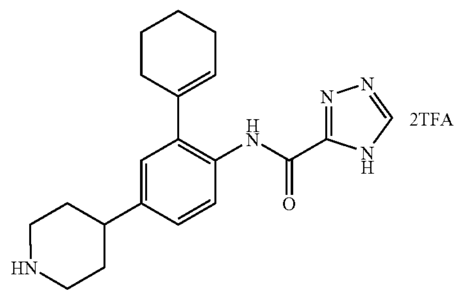 | 0.060 |
| 50 | 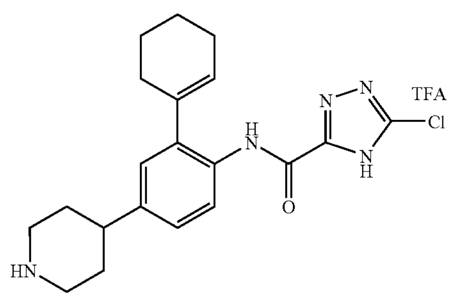 | 0.060 |
| 51a | 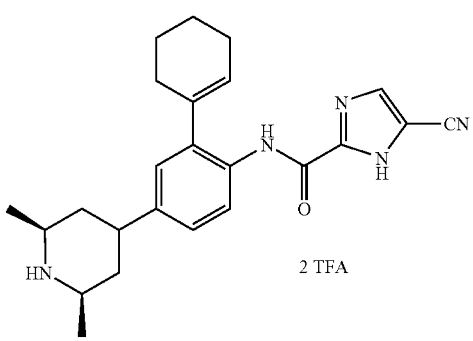 | 0.00020 |
| 51b | 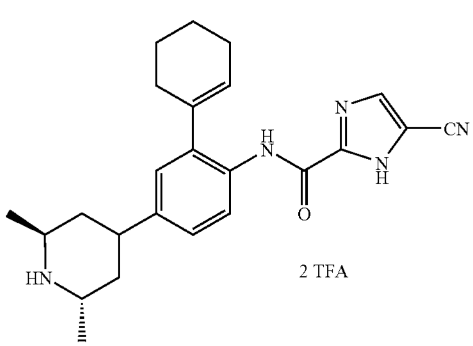 | 0.0004 |

TABLE 1-continued

| Example # | Structure | c-fms IC50 (μM) |
|---|---|---|
| 52 | 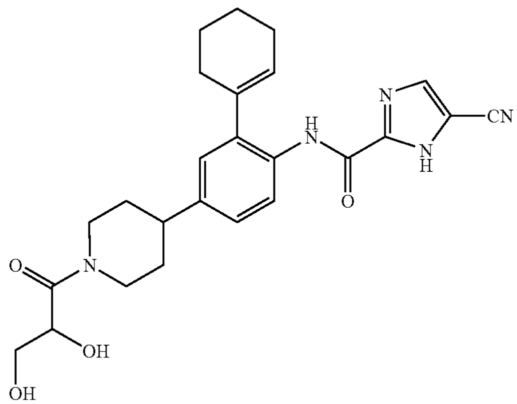 | 0.0012 |
| 53 | 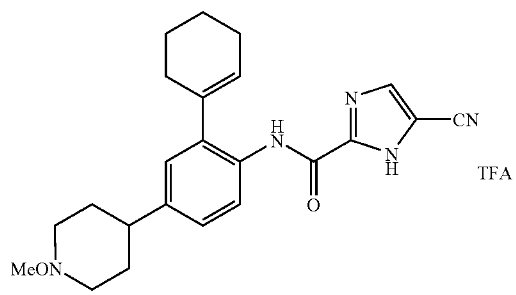 | 0.0053 (TFA) |
| 54 | 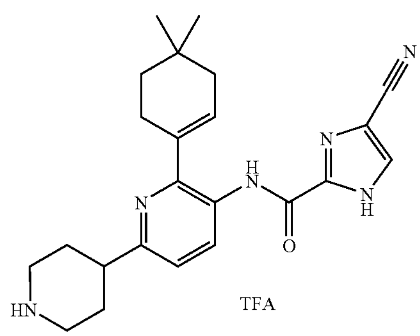 | 0.0008 (TFA) |
| 55 | 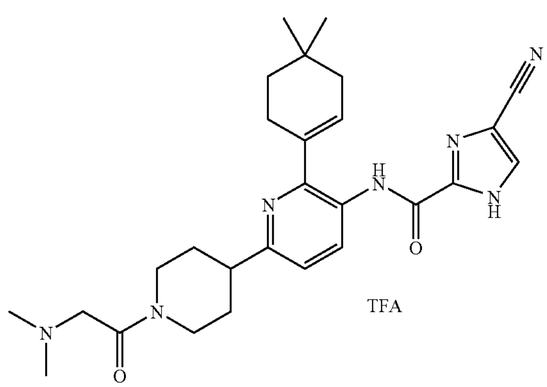 | 0.0007 (TFA) |

TABLE 1-continued

| Example # | Structure | c-fms IC50 (μM) |
|---|---|---|
| 56 | 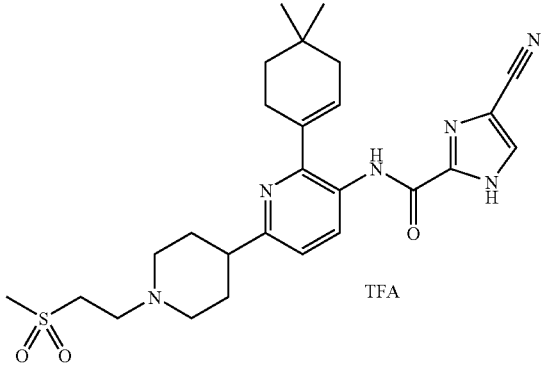 TFA | 0.001 |
| 57 | 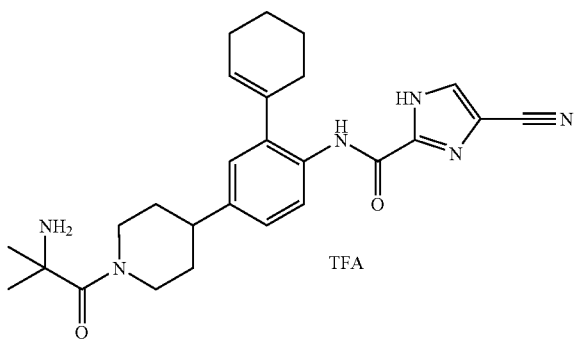 TFA | 0.0013 |
| 58 | 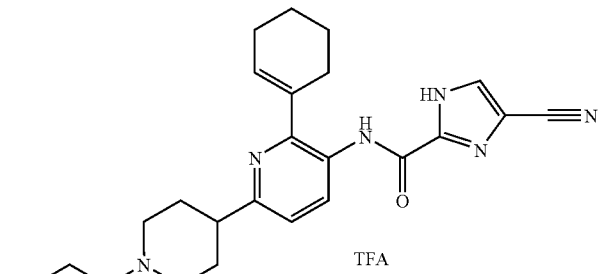 TFA | 0.0070 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The claimed invention is:

1. A compound selected from the group consisting of:

5-Cyano-1H-imidazole-2-carboxylic acid [4-(3,6-dihydro-2H-pyran-4-yl)-2-(4,4-dimethyl-cyclohex-1-enyl)-phenyl]-amide;

4-Cyano-1H-imidazole-2-carboxylic acid {2-cyclohept-1-enyl-4-[1-(2-dimethylamino-acetyl) -piperidin-4-yl]-phenyl}-amide trifluoroacetic acid salt;

4-Cyano-1H-imidazole-2-carboxylic acid [4-[1-(2-dimethylamino-acetyl)-piperidin-4-yl]-2-(4,4-dimethyl-cyclohex-1-enyl)-phenyl]-amide trifluoroacetic acid salt;

4-Cyano-1H-pyrrole-2-carboxylic acid {2-cyclohex-1-enyl-4-[1-(2-dimethylamino-acetyl) -piperidin-4-yl]-phenyl}-amide trifluoroacetic acid salt;

4-Cyano-1-imidazole-2-carboxylic acid {2-(4,4-dimethyl-cyclohex-1-enyl)-4-[1-(2-methanesulfonyl-ethyl)-piperidin-4-yl]-phenyl}-amide trifluoroacetic acid salt;

and tautomers and pharmaceutically acceptable salts thereof.

2. A compound which is:

4-cyano-1H-imidazole-2-carboxylic acid [2-cyclohex-1-enyl-4-(1-{2-[(2-hydroxy-ethyl)ethyl)-methyl-amino]-acetyl}-piperidin-4-yl)-phenyl]-amide, and tautomers and pharmaceutically acceptable salts thereof.

3. A compound which is:

4-cyano-1H-imidazole-2-carboxylic acid {2-cyclohex-1-enyl-4-[1-(2-morpholin-4-yl-acetyl)-piperidin-4-yl]-phenyl}-amide, and tautomers and pharmaceutically acceptable salts thereof.

4. A compound selected from the group consisting of:

4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt, 4H-[1,2,4]-triazole-3-carboxylic acid (2-cyclohex-1-enyl-4-piperidin-4-yl-phenyl)-amide bis trifluoroacetic acid salt, 5-Chloro-4H-[1,2,4]-triazole-3-carboxylic acid (2-cyclohex-1-enyl-4-piperidin-4-yl-phenyl)-amide trifluoroacetic acid salt, 5-Cyano-1H-imidazole-2-carboxylic acid [2-cyclohex-1-enyl-4-(cis-2,6-dimethyl-piperidin-4-yl)-phenyl]-amide bis trifluoroacetic acid salt, 5-cyano-1H-imidazole-2-carboxylic acid [2-cyclohex-1-enyl-4-(trans-2,6-dimethyl-piperidin-4-yl)-phenyl]-amide bis trifluoroacetic acid salt, 5-Cyano-1H-imidazole-2-carboxylic acid {2-cyclohex-1-enyl-4-[1-(R)-(+)-(2,3-dihydroxy-propionyl)-piperidin-4-yl]-phenyl}-amide, 5-Cyano-1H-imidazole-2-carboxylic acid [2-cyclohex-1-enyl-4-(1-methoxy-piperidin-4-yl)-phenyl]-amide trifluoroacetic acid salt, 4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt, 5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt, and 5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide, and tautomers and pharmaceutically acceptable salts thereof.

5. A pharmaceutical composition, comprising a compound of claim 1 and a pharmaceutically acceptable carrier.

6. A pharmaceutical dosage form comprising a pharmaceutically acceptable carrier and from about 0.5 mg to about 10 g of at least one compound of claim 1.

7. A dosage form according to claim 6 adapted for parenteral or oral administration.

* * * * *

UNITED STATES PATENT AND TRADEMARK OFFICE
CERTIFICATE OF CORRECTION

PATENT NO. : 7,645,755 B2 Page 1 of 1
APPLICATION NO. : 11/408096
DATED : January 12, 2010
INVENTOR(S) : Illig et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (349) days Delete the phrase "by 349 days" and insert -- by 413 days --

Signed and Sealed this

Twenty-fourth Day of August, 2010

David J. Kappos
*Director of the United States Patent and Trademark Office*